United States Patent
Aldridge et al.

(10) Patent No.: US 9,907,565 B2
(45) Date of Patent: Mar. 6, 2018

(54) ACTIVATION FEATURES FOR ULTRASONIC SURGICAL INSTRUMENT

(71) Applicant: Ethicon Endo-Surgery, Inc., Cincinnati, OH (US)

(72) Inventors: Jeffrey L. Aldridge, Lebanon, OH (US); Sean P. Conlon, Loveland, OH (US); Benjamin M. Boyd, Fairborn, OH (US); Daniel W. Price, Loveland, OH (US); James G. Lee, Cincinnati, OH (US)

(73) Assignee: Eithicon LLC, Guaynabo, PR (US)

( * ) Notice: Subject to any disclaimer, the term of this patent is extended or adjusted under 35 U.S.C. 154(b) by 11 days.

(21) Appl. No.: 14/515,129

(22) Filed: Oct. 15, 2014

(65) Prior Publication Data

US 2016/0106455 A1   Apr. 21, 2016

(51) Int. Cl.
*A61B 17/32* (2006.01)
*A61N 7/00* (2006.01)
(Continued)

(52) U.S. Cl.
CPC ........ *A61B 17/320068* (2013.01); *A61N 7/00* (2013.01); *A61B 17/320092* (2013.01);
(Continued)

(58) Field of Classification Search
CPC .. A61B 17/320068; A61B 2018/00601; A61B 2018/00589; A61B 2018/0063;
(Continued)

(56) References Cited

U.S. PATENT DOCUMENTS

| 3,746,814 A | 7/1973 | Lackey et al. |
| 5,322,055 A | 6/1994 | Davison et al. |

(Continued)

FOREIGN PATENT DOCUMENTS

| DE | 2262209 A1 | 7/1973 |
| DE | 2460481 A1 | 6/1976 |

(Continued)

OTHER PUBLICATIONS

U.S. Appl. No. 14/028,717, filed Sep. 17, 2013
(Continued)

*Primary Examiner* — Richard Louis
(74) *Attorney, Agent, or Firm* — Frost Brown Todd LLC

(57) ABSTRACT

An ultrasonic instrument comprises a handle assembly or other kind of body configured to receive an ultrasonic transducer and a shaft assembly having an acoustic waveguide and an ultrasonic blade. The ultrasonic blade is in acoustic communication with the acoustic waveguide such that the ultrasonic transducer is operable to drive the ultrasonic blade to vibrate ultrasonically via the acoustic waveguide. The ultrasonic instrument further comprises an actuation assembly disposed within the handle assembly. The actuation assembly includes a plurality of buttons disposed about the handle assembly in an angularly spaced array. Each button may be depressed independently of the rest to thereby actuate a switch assembly such that power is provided to the ultrasonic transducer, the acoustic waveguide, and the ultrasonic blade. The actuation assembly is operable to convert radial movement of the buttons into longitudinal, transverse, and/or pivotal movement that actuates the switch assembly.

20 Claims, 48 Drawing Sheets

(51) Int. Cl.
  *A61B 17/00* (2006.01)
  *A61B 18/00* (2006.01)
(52) U.S. Cl.
  CPC .............. *A61B 2017/00017* (2013.01); *A61B 2017/0042* (2013.01); *A61B 2017/00367* (2013.01); *A61B 2017/00371* (2013.01); *A61B 2017/00389* (2013.01); *A61B 2017/00407* (2013.01); *A61B 2017/00424* (2013.01); *A61B 2018/0063* (2013.01); *A61B 2018/0094* (2013.01); *A61B 2018/00589* (2013.01); *A61B 2018/00601* (2013.01); *A61B 2018/00916* (2013.01); *H01H 2221/016* (2013.01); *H01H 2221/036* (2013.01); *H01H 2300/014* (2013.01)
(58) Field of Classification Search
  CPC .......... A61B 2017/00407; A61B 2017/00389; A61B 2017/00371; A61B 17/320092; A61B 2017/00017; A61B 2017/00367; A61B 2017/00424; A61B 2018/00916; A61B 2018/0094; A61B 2017/0042; A61N 7/00; H01H 2300/014; H01H 2221/016; H01H 2221/036
  See application file for complete search history.

(56) References Cited

U.S. PATENT DOCUMENTS

| | | | |
|---|---|---|---|
| 5,324,299 A | 6/1994 | Davison et al. | |
| 5,873,873 A | 2/1999 | Smith et al. | |
| 5,980,510 A | 11/1999 | Tsonton et al. | |
| 6,283,981 B1 | 9/2001 | Beaupre | |
| 6,309,400 B2 | 10/2001 | Beaupre | |
| 6,325,811 B1 | 12/2001 | Messerly | |
| 6,423,082 B1 | 7/2002 | Houser et al. | |
| 6,773,444 B2 | 8/2004 | Messerly | |
| 6,783,524 B2 | 8/2004 | Anderson et al. | |
| 6,945,981 B2 | 9/2005 | Donofrio et al. | |
| 8,057,498 B2 | 11/2011 | Robertson | |
| 8,152,825 B2 | 4/2012 | Madan et al. | |
| 8,461,744 B2 | 6/2013 | Wiener et al. | |
| 8,591,536 B2 | 11/2013 | Robertson | |
| 8,623,027 B2 | 1/2014 | Price et al. | |
| 8,911,460 B2 | 12/2014 | Neurohr et al. | |
| 9,023,071 B2 | 5/2015 | Miller et al. | |
| 9,107,688 B2 | 9/2015 | Kimball et al. | |
| 9,241,732 B2 | 1/2016 | Craig | |
| 2006/0079874 A1 | 4/2006 | Faller et al. | |
| 2007/0191713 A1 | 8/2007 | Eichmann et al. | |
| 2007/0282333 A1 | 12/2007 | Fortson et al. | |
| 2008/0200940 A1 | 8/2008 | Eichmann et al. | |
| 2010/0069940 A1* | 3/2010 | Miller | A61B 17/320068 606/169 |
| 2011/0087212 A1 | 4/2011 | Aldridge et al. | |
| 2012/0112687 A1 | 5/2012 | Houser et al. | |
| 2012/0116265 A1 | 5/2012 | Houser et al. | |
| 2012/0116391 A1* | 5/2012 | Houser | A61B 17/320092 606/41 |
| 2014/0005701 A1 | 1/2014 | Olson et al. | |
| 2014/0114334 A1 | 4/2014 | Olson et al. | |
| 2015/0182249 A1* | 7/2015 | Conlon | A61B 17/320068 606/169 |
| 2015/0209071 A1 | 7/2015 | Miller et al. | |

FOREIGN PATENT DOCUMENTS

| | | |
|---|---|---|
| GB | 2450239 A | 12/2008 |
| NL | 1017424 C2 | 8/2002 |
| WO | WO 96/24298 A1 | 8/1996 |
| WO | WO 98/27875 A1 | 7/1998 |
| WO | WO 2008/089174 A2 | 7/2008 |
| WO | WO 2010/030850 A2 | 3/2010 |

OTHER PUBLICATIONS

U.S. Appl. No. 14/087,383, filed Nov. 22, 2013.
U.S. Appl. No. 14/337,508, filed Jul. 22, 2014.
U.S. Appl. No. 14/488,330, filed Sep. 17, 2014.
U.S. Appl. No. 61/410,603, filed Nov. 5, 2010.
International Search Report and Written Opinion dated Apr. 28, 2016 for Application No. PCT/US2015/052780, 22 pgs.

* cited by examiner

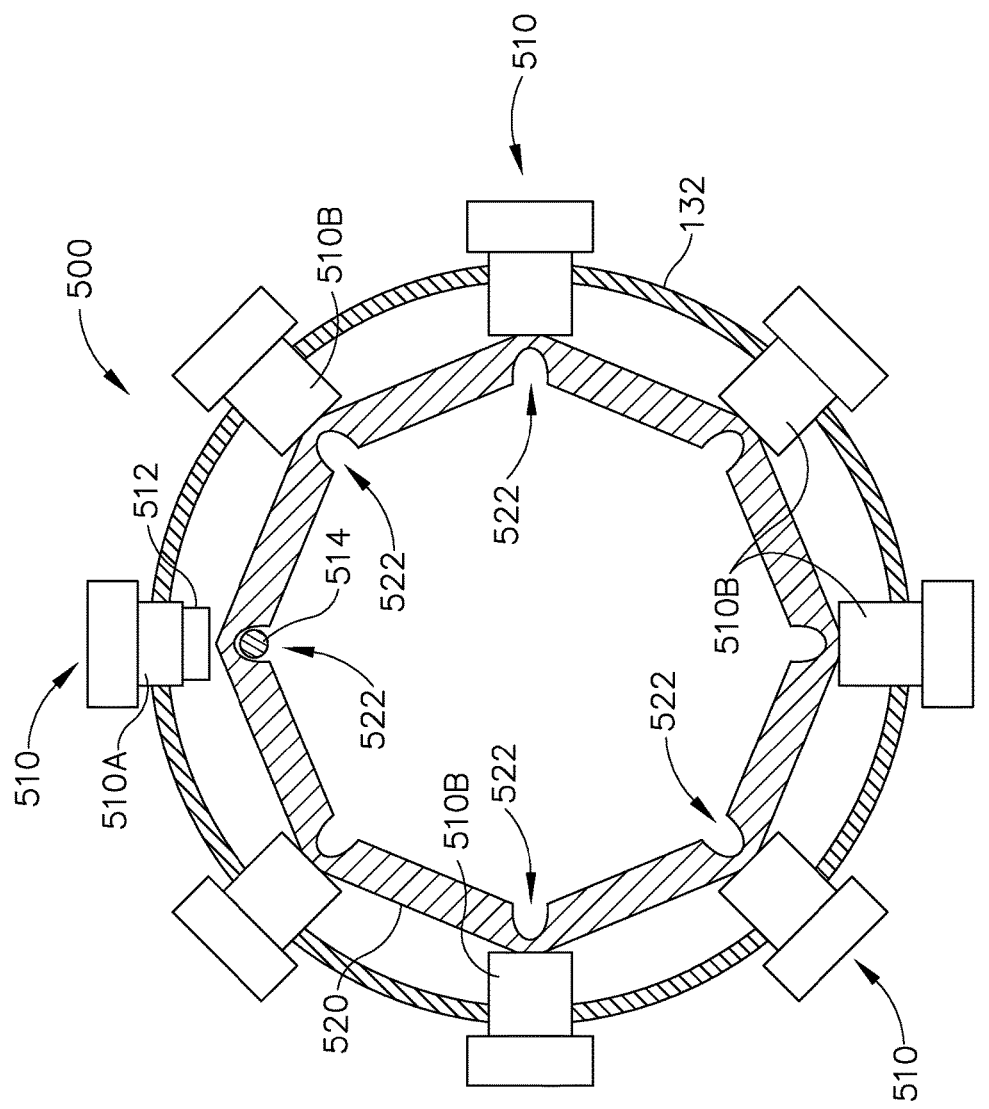

ACTIVATION FEATURES FOR ULTRASONIC SURGICAL INSTRUMENT

BACKGROUND

A variety of surgical instruments include an end effector having a blade element that vibrates at ultrasonic frequencies to cut and/or seal tissue (e.g., by denaturing proteins in tissue cells). These instruments include one or more piezoelectric elements that convert electrical power into ultrasonic vibrations, which are communicated along an acoustic waveguide to the blade element. The precision of cutting and coagulation may be controlled by the operator's technique and adjusting the power level, blade edge angle, tissue traction, and blade pressure.

Examples of ultrasonic surgical instruments include the HARMONIC ACE® Ultrasonic Shears, the HARMONIC WAVE® Ultrasonic Shears, the HARMONIC FOCUS® Ultrasonic Shears, and the HARMONIC SYNERGY® Ultrasonic Blades, all by Ethicon Endo-Surgery, Inc. of Cincinnati, Ohio. Further examples of such devices and related concepts are disclosed in U.S. Pat. No. 5,322,055, entitled "Clamp Coagulator/Cutting System for Ultrasonic Surgical Instruments," issued Jun. 21, 1994, the disclosure of which is incorporated by reference herein; U.S. Pat. No. 5,873,873, entitled "Ultrasonic Clamp Coagulator Apparatus Having Improved Clamp Mechanism," issued Feb. 23, 1999, the disclosure of which is incorporated by reference herein; U.S. Pat. No. 5,980,510, entitled "Ultrasonic Clamp Coagulator Apparatus Having Improved Clamp Arm Pivot Mount," issued Nov. 9, 1999, the disclosure of which is incorporated by reference herein; U.S. Pat. No. 6,283,981, entitled "Method of Balancing Asymmetric Ultrasonic Surgical Blades," issued Sep. 4, 2001, the disclosure of which is incorporated by reference herein; U.S. Pat. No. 6,309,400, entitled "Curved Ultrasonic Blade having a Trapezoidal Cross Section," issued Oct. 30, 2001, the disclosure of which is incorporated by reference herein; U.S. Pat. No. 6,325,811, entitled "Blades with Functional Balance Asymmetries for use with Ultrasonic Surgical Instruments," issued Dec. 4, 2001, the disclosure of which is incorporated by reference herein; U.S. Pat. No. 6,423,082, entitled "Ultrasonic Surgical Blade with Improved Cutting and Coagulation Features," issued Jul. 23, 2002, the disclosure of which is incorporated by reference herein; U.S. Pat. No. 6,773,444, entitled "Blades with Functional Balance Asymmetries for Use with Ultrasonic Surgical Instruments," issued Aug. 10, 2004, the disclosure of which is incorporated by reference herein; U.S. Pat. No. 6,783,524, entitled "Robotic Surgical Tool with Ultrasound Cauterizing and Cutting Instrument," issued Aug. 31, 2004, the disclosure of which is incorporated by reference herein; U.S. Pat. No. 8,057,498, entitled "Ultrasonic Surgical Instrument Blades," issued Nov. 15, 2011, the disclosure of which is incorporated by reference herein; U.S. Pat. No. 8,461,744, entitled "Rotating Transducer Mount for Ultrasonic Surgical Instruments," issued Jun. 11, 2013, the disclosure of which is incorporated by reference herein; U.S. Pat. No. 8,591,536, entitled "Ultrasonic Surgical Instrument Blades," issued Nov. 26, 2013, the disclosure of which is incorporated by reference herein; and U.S. Pat. No. 8,623,027, entitled "Ergonomic Surgical Instruments," issued Jan. 7, 2014, the disclosure of which is incorporated by reference herein.

Still further examples of ultrasonic surgical instruments are disclosed in U.S. Pub. No. 2006/0079874, entitled "Tissue Pad for Use with an Ultrasonic Surgical Instrument," published Apr. 13, 2006, the disclosure of which is incorporated by reference herein; U.S. Pub. No. 2007/0191713, entitled "Ultrasonic Device for Cutting and Coagulating," published Aug. 16, 2007, the disclosure of which is incorporated by reference herein; U.S. Pub. No. 2007/0282333, entitled "Ultrasonic Waveguide and Blade," published Dec. 6, 2007, the disclosure of which is incorporated by reference herein; U.S. Pub. No. 2008/0200940, entitled "Ultrasonic Device for Cutting and Coagulating," published Aug. 21, 2008, the disclosure of which is incorporated by reference herein; U.S. Pub. No. 2008/0234710, entitled "Ultrasonic Surgical Instruments," published Sep. 25, 2008, now U.S. Pat. No. 8,911,460, issued Dec. 16, 2014, the disclosure of which is incorporated by reference herein; and U.S. Pub. No. 2010/0069940, entitled "Ultrasonic Device for Fingertip Control," published Mar. 18, 2010, now U.S. Pat. No. 9,023,071, issued May 5, 2015, the disclosure of which is incorporated by reference herein.

Some ultrasonic surgical instruments may include a cordless transducer such as that disclosed in U.S. Pub. No. 2012/0112687, entitled "Recharge System for Medical Devices," published May 10, 2012, now U.S. Pat. No. 9,381,058, issued Jul. 5, 2016, the disclosure of which is incorporated by reference herein; U.S. Pub. No. 2012/0116265, entitled "Surgical Instrument with Charging Devices," published May 10, 2012, the disclosure of which is incorporated by reference herein; and/or U.S. Pat. App. No. 61/410,603, filed Nov. 5, 2010, entitled "Energy-Based Surgical Instruments," the disclosure of which is incorporated by reference herein.

Additionally, some ultrasonic surgical instruments may include an articulating shaft section. Examples of such ultrasonic surgical instruments are disclosed in U.S. Pub. No. 2014/0005701, published Jan. 2, 2014, entitled "Surgical Instruments with Articulating Shafts," now U.S. Pat. No. 9,393,037, issued Jul. 19, 2016, the disclosure of which is incorporated by reference herein; and U.S. Pub. No. 2014/0114334, published Apr. 24, 2014, entitled "Flexible Harmonic Waveguides/Blades for Surgical Instruments," now U.S. Pat. No. 9,095,367, issued Aug. 4, 2015, the disclosure of which is incorporated by reference herein.

While several surgical instruments and systems have been made and used, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 30 depicts a front cross-sectional view of yet another exemplary alternative actuation assembly that may be incorporated into the instrument of FIG. 2;

Figure 1:
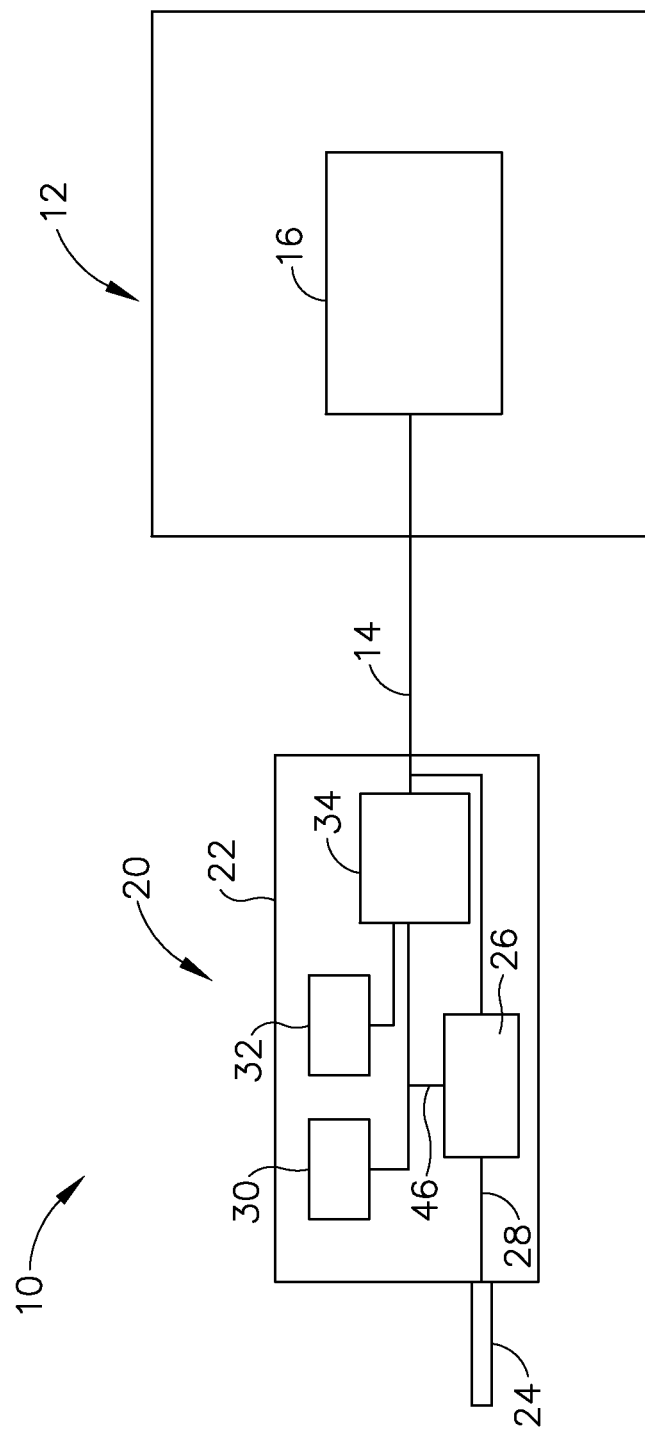
FIG. 1 depicts a block schematic view of an exemplary surgical instrument.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to an operator or other operator grasping a surgical instrument having a distal surgical end effector. The term "proximal" refers the position of an element closer to the operator or other operator and the term "distal" refers to the position of an element closer to the surgical end effector of the surgical instrument and further away from the operator or other operator.

I. Overview of Exemplary Ultrasonic Surgical System

FIG. 1 shows components of an exemplary surgical system (10) in diagrammatic block form. As shown, system (10) comprises an ultrasonic generator (12) and an ultrasonic surgical instrument (20). As will be described in greater detail below, instrument (20) is operable to cut tissue and seal or weld tissue (e.g., a blood vessel, etc.) substantially simultaneously, using ultrasonic vibrational energy. Generator (12) and instrument (20) are coupled together via cable (14). Cable (14) may comprise a plurality of wires; and may provide unidirectional electrical communication from generator (12) to instrument (20) and/or bidirectional electrical communication between generator (12) and instrument (20). By way of example only, cable (14) may comprise a "hot" wire for electrical power to surgical instrument (20), a ground wire, and a signal wire for transmitting signals from surgical instrument (20) to ultrasonic generator (12), with a shield surrounding the three wires. In some versions, separate "hot" wires are used for separate activation voltages (e.g., one "hot" wire for a first activation voltage and another "hot" wire for a second activation voltage, or a variable voltage between the wires proportional to the power requested, etc.). Of course, any other suitable number or configuration of wires may be used. It should also be understood that some versions of system (10) may incorporate generator (12) into instrument (20), such that cable (14) may simply be omitted.

By way of example only, generator (12) may comprise the GEN04, GEN11, or GEN 300 sold by Ethicon Endo-Surgery, Inc. of Cincinnati, Ohio. In addition or in the alternative, generator (12) may be constructed in accordance with at least some of the teachings of U.S. Pub. No. 2011/0087212, entitled "Surgical Generator for Ultrasonic and Electrosurgical Devices," published Apr. 14, 2011, now U.S. Pat. No. 8,986,302, issued Mar. 24, 2015, the disclosure of which is incorporated by reference herein. Alternatively, any other suitable generator (12) may be used. As will be described in greater detail below, generator (12) is operable to provide power to instrument (20) to perform ultrasonic surgical procedures.

Instrument (20) comprises a handpiece (22), which is configured to be grasped in one hand (or two hands) of an operator and manipulated by one hand (or two hands) of the operator during a surgical procedure. For instance, in some versions, handpiece (22) may be grasped like a pencil by the operator. In some other versions, handpiece (22) may include a scissor grip that may be grasped like scissors by the operator. In some other versions, handpiece (22) may include a pistol grip that may be grasped like a pistol by the operator. Of course, handpiece (22) may be configured to be gripped in any other suitable fashion. Furthermore, some versions of instrument (20) may substitute handpiece (22) with a body that is coupled to a robotic surgical system that is configured to operate instrument (e.g., via remote control, etc.). In the present example, a blade (24) extends distally from the handpiece (22). Handpiece (22) includes an ultrasonic transducer (26) and an ultrasonic waveguide (28), which couples ultrasonic transducer (26) with blade (24). Ultrasonic transducer (26) receives electrical power from generator (12) via cable (14). By virtue of its piezoelectric properties, ultrasonic transducer (26) is operable to convert such electrical power into ultrasonic vibrational energy.

Ultrasonic waveguide (28) may be flexible, semi-flexible, rigid, or have any other suitable properties. As noted above, ultrasonic transducer (26) is integrally coupled with blade (24) via ultrasonic waveguide (28). In particular, when ultrasonic transducer (26) is activated to vibrate at ultrasonic frequencies, such vibrations are communicated through ultrasonic waveguide (28) to blade (24), such that blade (24) will also vibrate at ultrasonic frequencies. When blade (24) is in an activated state (i.e., vibrating ultrasonically), blade (24) is operable to effectively cut through tissue and seal tissue. Ultrasonic transducer (26), ultrasonic waveguide (28), and blade (24) together thus form an acoustic assembly providing ultrasonic energy for surgical procedures when powered by generator (12). Handpiece (22) is configured to substantially isolate the operator from the vibrations of the acoustic assembly formed by transducer (26), ultrasonic waveguide (28), and blade (24).

In some versions, ultrasonic waveguide (28) may amplify the mechanical vibrations transmitted through ultrasonic waveguide (28) to blade (24). Ultrasonic waveguide (28) may further have features to control the gain of the longitudinal vibration along ultrasonic waveguide (28) and/or features to tune ultrasonic waveguide (28) to the resonant frequency of system (10). For instance, ultrasonic waveguide (28) may have any suitable cross-sectional dimensions/configurations, such as a substantially uniform cross-section, be tapered at various sections, be tapered along its entire length, or have any other suitable configuration. Ultrasonic waveguide (28) may, for example, have a length substantially equal to an integral number of one-half system wavelengths ($n\lambda/2$). Ultrasonic waveguide (28) and blade (24) may be fabricated from a solid core shaft constructed out of a material or combination of materials that propagates ultrasonic energy efficiently, such as titanium alloy (i.e., Ti-6Al-4V), aluminum alloys, sapphire, stainless steel, or any other acoustically compatible material or combination of materials.

In the present example, the distal end of blade (24) is located at a position corresponding to an anti-node associated with resonant ultrasonic vibrations communicated through waveguide (28) (i.e., at an acoustic anti-node), in order to tune the acoustic assembly to a preferred resonant frequency $f_o$ when the acoustic assembly is not loaded by tissue. When transducer (26) is energized, the distal end of blade (24) is configured to move longitudinally in the range of, for example, approximately 10 to 500 microns peak-to-peak, and in some instances in the range of about 20 to about 200 microns at a predetermined vibratory frequency $f_o$ of, for example, 55.5 kHz. When transducer (26) of the present example is activated, these mechanical oscillations are transmitted through waveguide (28) to reach blade (24), thereby providing oscillation of blade (24) at the resonant ultrasonic frequency. Thus, the ultrasonic oscillation of blade (24) may simultaneously sever the tissue and denature the proteins in adjacent tissue cells, thereby providing a coagulative effect with relatively little thermal spread. In some versions, an electrical current may also be provided through blade (24) to also cauterize the tissue.

By way of example only, ultrasonic waveguide (28) and blade (24) may comprise components sold under product codes SNGHK and SNGCB by Ethicon Endo-Surgery, Inc. of Cincinnati, Ohio. By way of further example only, ultrasonic waveguide (28) and/or blade (24) may be constructed and operable in accordance with the teachings of U.S. Pat. No. 6,423,082, entitled "Ultrasonic Surgical Blade with Improved Cutting and Coagulation Features," issued Jul. 23, 2002, the disclosure of which is incorporated by reference herein. As another merely illustrative example, ultrasonic waveguide (28) and/or blade (24) may be constructed and operable in accordance with the teachings of U.S. Pat. No. 5,324,299, entitled "Ultrasonic Scalpel Blade and Methods of Application," issued Jun. 28, 1994, the disclosure of which is incorporated by reference herein. Other suitable properties and configurations of ultrasonic waveguide (28) and blade (24) will be apparent to those of ordinary skill in the art in view of the teachings herein.

Handpiece (22) of the present example also includes a control selector (30) and an activation switch (32), which are each in communication with a circuit board (34). By way of example only, circuit board (34) may comprise a conventional printed circuit board, a flex circuit, a rigid-flex circuit, or may have any other suitable configuration. Control selector (30) and activation switch (32) may be in communication with circuit board (34) via one or more wires, traces formed in a circuit board or flex circuit, and/or in any other suitable fashion. Circuit board (34) is coupled with cable (14), which is in turn coupled with control circuitry (16) within generator (12). Activation switch (32) is operable to selectively activate power to ultrasonic transducer (26). In particular, when switch (32) is activated, such activation provides communication of appropriate power to ultrasonic transducer (26) via cable (14). By way of example only, activation switch (32) may be constructed in accordance with any of the teachings of the various references cited herein. Other various forms that activation switch (32) may take will be apparent to those of ordinary skill in the art in view of the teachings herein.

In the present example, surgical system (10) is operable to provide at least two different levels or types of ultrasonic energy (e.g., different frequencies and/or amplitudes, etc.) at blade (24). To that end, control selector (30) is operable to permit the operator to select a desired level/amplitude of ultrasonic energy. By way of example only, control selector (30) may be constructed in accordance with any of the teachings of the various references cited herein. Other various forms that control selector (30) may take will be apparent to those of ordinary skill in the art in view of the teachings herein. In some versions, when an operator makes a selection through control selector (30), the operator's selection is communicated back to control circuitry (16) of generator (12) via cable (14), and control circuitry (16) adjusts the power communicated from generator (12) accordingly the next time the operator actuates activation switch (32).

It should be understood that the level/amplitude of ultrasonic energy provided at blade (24) may be a function of characteristics of the electrical power communicated from generator (12) to instrument (20) via cable (14). Thus, control circuitry (16) of generator (12) may provide electrical power (via cable (14)) having characteristics associated with the ultrasonic energy level/amplitude or type selected through control selector (30). Generator (12) may thus be operable to communicate different types or degrees of electrical power to ultrasonic transducer (26), in accordance with selections made by the operator via control selector (30). In particular, and by way of example only, generator (12) may increase the voltage and/or current of the applied signal to increase the longitudinal amplitude of the acoustic assembly. As a merely illustrative example, generator (12) may provide selectability between a "level 1" and a "level 5," which may correspond with a blade (24) vibrational resonance amplitude of approximately 50 microns and approximately 90 microns, respectively. Various ways in which control circuitry (16) may be configured will be apparent to those of ordinary skill in the art in view of the teachings herein. It should also be understood that control selector (30) and activation switch (32) may be substituted with two or more activation switches (32). In some such versions, one activation switch (32) is operable to activate blade (24) at one power level/type while another activation switch (32) is operable to activate blade (24) at another power level/type, etc.

In some alternative versions, control circuitry (16) is located within handpiece (22). For instance, in some such versions, generator (12) only communicates one type of electrical power (e.g., just one voltage and/or current available) to handpiece (22), and control circuitry (16) within handpiece (22) is operable to modify the electrical power (e.g., the voltage of the electrical power), in accordance with selections made by the operator via control selector (30), before the electrical power reaches ultrasonic transducer (26). Furthermore, generator (12) may be incorporated into handpiece (22) along with all other components of surgical system (10). For instance, one or more batteries (not shown) or other portable sources of power may be provided in handpiece (22). Still other suitable ways in which the components depicted in FIG. 1 may be rearranged or otherwise configured or modified will be apparent to those of ordinary skill in the art in view of the teachings herein.

II. Overview of Exemplary Ultrasonic Surgical Instrument

The following discussion relates to various exemplary components and configurations for instrument (20). It should be understood that the various examples of instrument (20) described below may be readily incorporated into a surgical system (10) as described above. It should also be understood that the various components and operability of instrument (20) described above may be readily incorporated into the exemplary versions of instrument (20) described below. Various suitable ways in which the above and below teachings may be combined will be apparent to those of ordinary skill in the art in view of the teachings herein. It should also be understood that the below teachings may be readily combined with the various teachings of the references that are cited herein.

FIGS. 2-17B illustrate an exemplary ultrasonic surgical instrument (120). At least part of instrument (120) may be constructed and operable in accordance with at least some of the teachings of U.S. Pat. No. 5,322,055; U.S. Pat. No. 5,873,873; U.S. Pat. No. 5,980,510; U.S. Pat. No. 6,325,811; U.S. Pat. No. 6,773,444; U.S. Pat. No. 6,783,524; U.S. Pat. No. 8,461,744; U.S. Pub. No. 2009/0105750, now U.S. Pat. No. 8,623,027; U.S. Pub. No. 2006/0079874; U.S. Pub. No. 2007/0191713; U.S. Pub. No. 2007/0282333; U.S. Pub. No. 2008/0200940; U.S. Pub. No. 2010/0069940, now U.S. Pat. No. 9,023,071; U.S. Pub. No. 2012/0112687, now U.S. Pat. No. 9,381,058; U.S. Pub. No. 2012/0116265; U.S. Pub. No. 2014/0005701, now U.S. Pat. No. 9,393,037; U.S. Pat. Pub. No. 2014/0114334, now U.S. Pat. No. 9,095,367; U.S. patent application Ser. No. 14/028,717, published as U.S. Pub. No. 2015/0080924 on Mar. 19, 2015; and/or U.S. Pat. App. No. 61/410,603. The disclosures of each of the foregoing patents, publications, and applications are incorporated by reference herein. As described therein and as will be described in greater detail below, instrument (120) is operable to cut tissue and seal or weld tissue substantially simultaneously. It should also be understood that instrument (120) may have various structural and functional similarities with the HARMONIC ACE® Ultrasonic Shears, the HARMONIC WAVE® Ultrasonic Shears, the HARMONIC FOCUS® Ultrasonic Shears, and/or the HARMONIC SYNERGY® Ultrasonic Blades. Furthermore, instrument (120) may have various structural and functional similarities with the devices taught in any of the other references that are cited and incorporated by reference herein.

To the extent that there is some degree of overlap between the teachings of the references cited herein, the HARMONIC ACE® Ultrasonic Shears, the HARMONIC WAVE® Ultrasonic Shears, the HARMONIC FOCUS® Ultrasonic Shears, and/or the HARMONIC SYNERGY® Ultrasonic Blades, and the following teachings relating to instrument (120), there is no intent for any of the description herein to be presumed as admitted prior art. Several teachings herein will in fact go beyond the scope of the teachings of the references cited herein and the HARMONIC ACE® Ultrasonic Shears, the HARMONIC WAVE® Ultrasonic Shears, the HARMONIC FOCUS® Ultrasonic Shears, and the HARMONIC SYNERGY® Ultrasonic Blades.

Figure 2:
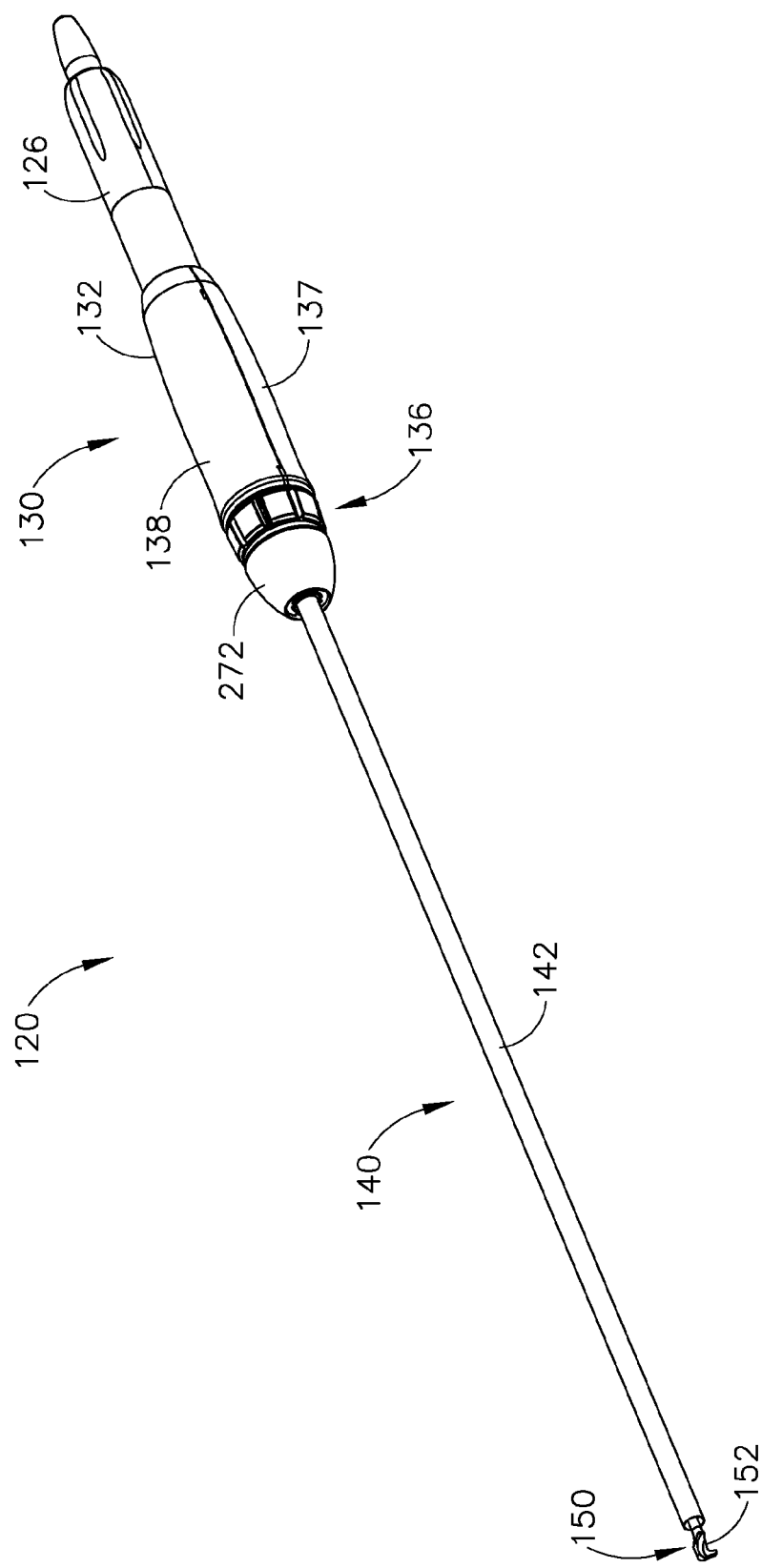
FIG. 2 depicts a perspective view of another exemplary surgical instrument.
Figure 3:
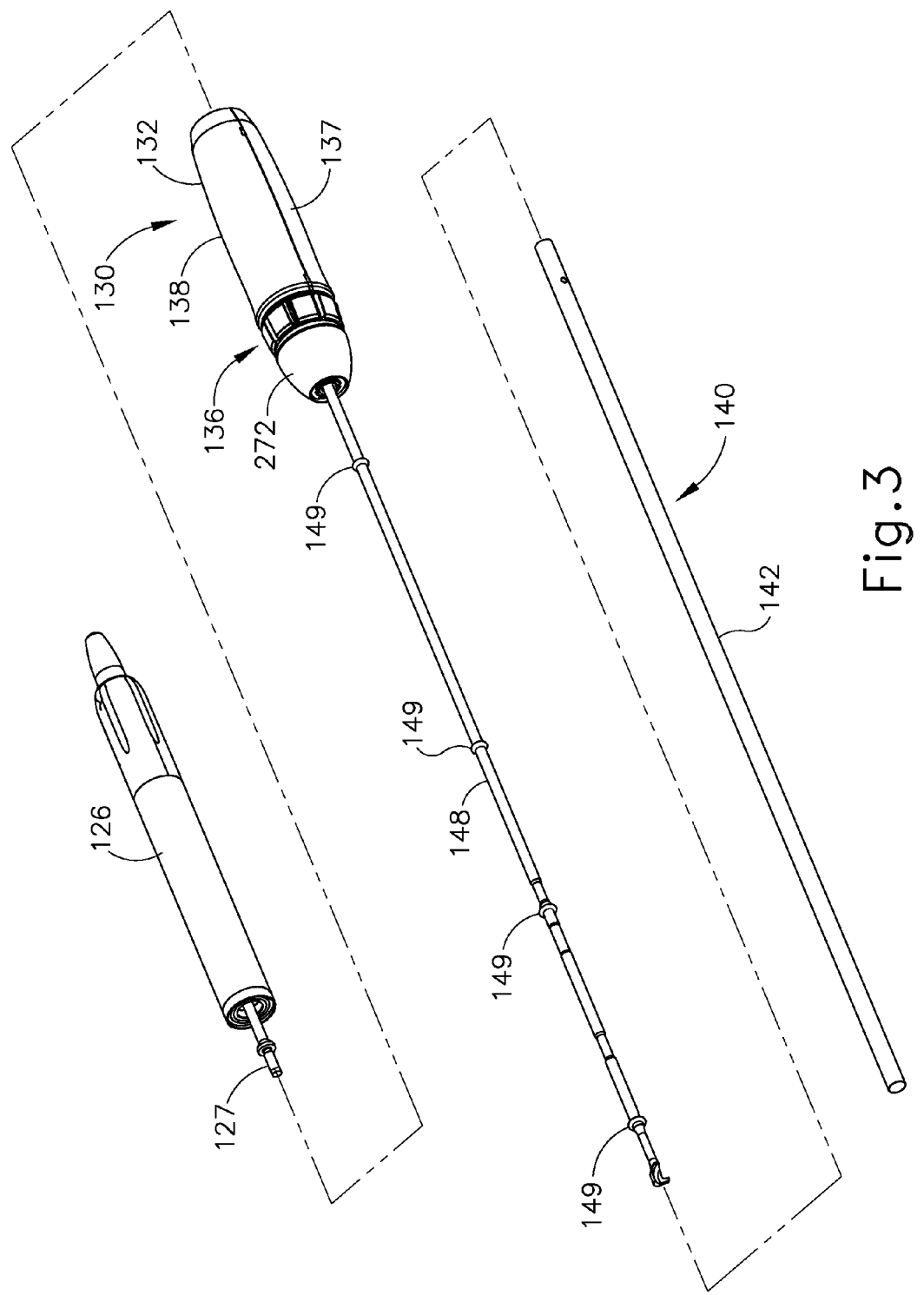
FIG. 3 depicts a partially exploded perspective view of the instrument of FIG. 2.

Instrument (120) is configured to be used as a scalpel. As shown in FIGS. 2-3, instrument (120) of this example comprises a handle assembly (130), a shaft assembly (140), and an end effector (150). In some versions, instrument (120) may be used in conjunction with ultrasonic surgical system (10), which includes ultrasonic transducer (26) coupled with ultrasonic generator (12) via cable (14). In the present example, however, the proximal end of instrument (120) receives and is fitted with an ultrasonic transducer (126) by insertion of ultrasonic transducer (126) into handle assembly (130). Handle assembly (130) is configured to receive ultrasonic transducer (126) such that ultrasonic transducer (126) may be coupled to a waveguide (148) in shaft assembly (140) by a threaded connection, though any other suitable type of coupling may be used. As shown in FIGS. 2-3, instrument (120) may be coupled with ultrasonic transducer (126) to form a single unit.

A. Exemplary Shaft Assembly and End Effector

Figure 4:
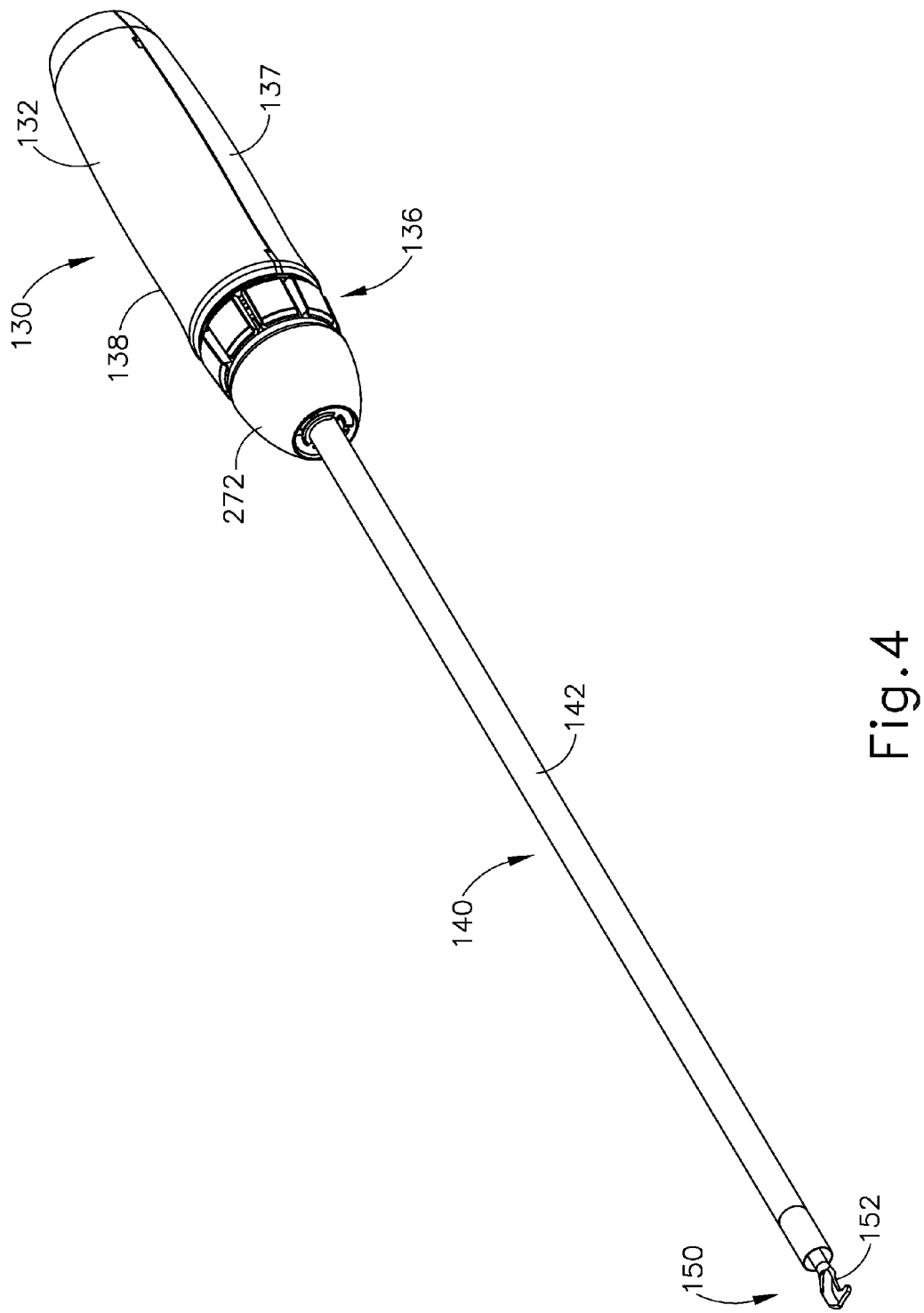
FIG. 4 depicts another perspective view of the instrument of FIG. 2, with an ultrasonic transducer of the instrument omitted.

As best seen in FIGS. 2-4, shaft assembly (140) comprises an outer sheath (142) and a waveguide (148) disposed within outer sheath (142). In some versions, outer sheath (142) and a waveguide (148) are sized to fit through a trocar or other minimally invasive access port, such that instrument (120) may be used in a minimally invasive surgical procedure. Waveguide (148) is configured to transmit ultrasonic vibrations from transducer (126) to an ultrasonic blade (152). Waveguide (148) may be flexible, semi-flexible or rigid. Waveguide (148) may also be configured to amplify the mechanical vibrations transmitted through waveguide (148) to blade (152). Waveguide (148) may further include at least one bore (not shown) extending therethrough, substantially perpendicular to the longitudinal axis of waveguide (148). The bore may be located at a longitudinal position corresponding to a node associated with ultrasonic vibrations communicated along waveguide (148). The bore may be configured to receive a connector pin (not shown) that connects ultrasonic waveguide (148) to outer sheath (142). Since the connector pin would be located at a nodal position, the pin would not transmit ultrasonic vibrations from waveguide (148) to outer sheath (142); yet the connector pin may still provide a longitudinal and rotational ground for outer sheath (142).

Blade (152) may be integral with ultrasonic waveguide (148) and formed as a single unit. In some versions, blade (152) may be connected to waveguide (148) by a threaded connection, a welded joint, and/or some other coupling feature(s). The distal end of blade (152) is disposed at or near a longitudinal position corresponding to an anti-node associated with ultrasonic vibrations communicated along waveguide (148) and blade (152) in order to tune the acoustic assembly to a preferred resonant frequency $f_o$ when the acoustic assembly is not loaded by tissue. When transducer (126) is energized, the distal end of blade (152) is configured to move substantially longitudinally (along the x axis) in the range of, for example, approximately 10 to 500 microns peak-to-peak, and perhaps in the range of about 20 to about 200 microns, at a predetermined vibrational frequency $f_o$ of, for example, 55,500 Hz. The distal end of blade (152) may also vibrate in the y-axis at about 1 to about 10 percent of the motion in the x-axis. Of course, movement of blade (152) when transducer (126) is energized may alternatively have any other suitable characteristics.

Waveguide (148) is positioned within outer sheath (142) and is held in place via a pin (not shown) as described above. The pin may be made of any compatible metal, such as stainless steel or titanium or a durable plastic, such as polycarbonate or a liquid crystal polymer. Alternatively, any other suitable material or combination of materials may be used. In some versions, the pin is partially coated with an elastomeric material, such as silicon, etc., for the portion of the pin that extends through ultrasonic waveguide (148). Elastomeric material may provide insulation from the vibrating blade throughout the length of a bore. In some settings, this may enable high efficiency operation whereby minimal overheating is generated and maximum ultrasonic output power is available at the distal end of blade (152) for cutting and coagulation, etc. Of course, such elastomeric material is merely optional. It should also be understood that waveguide (148) may include an elastomeric material at the opening where the pin is received. By way of example only, waveguide (148) may be constructed in accordance with at least some of the teachings of U.S. patent application Ser. No. 14/337,508, entitled "Ultrasonic Blade Overmold," filed Jul. 22, 2014, now U.S. Pat. No. 9,750,521, issued Sep. 5, 2017, the disclosure of which is incorporated by reference herein.

As can be seen in FIG. 3, waveguide (148) has a plurality of acoustic isolators (149) positioned along the longitudinal length of waveguide (148). Isolators (149) may provide structural support to waveguide (148); and/or acoustic isolation between waveguide (148) and other portions of shaft assembly (140). Isolators (149) generally have a circular or ovular cross-section and extend circumferentially around the diameter of waveguide (148). The inner diameter of each isolator (149) is generally sized slightly smaller than the outer diameter of waveguide (148) to create a slight interference fit, thus securing each isolator (149) to waveguide (148). In some examples, waveguide (148) may include annular recesses that are configured to receive each isolator (149) to further aid in securing each isolator (149) along the longitudinal length of waveguide (148). In the present example, each isolator (149) is positioned at or near to an acoustic node along the longitudinal length of waveguide (148) (i.e., a longitudinal position corresponding to a node associated with resonant ultrasonic vibrations communicated through waveguide (148)). Such positioning may reduce the vibrations transferred to isolators (149) (and to other components in contact with isolators (149)) via waveguide (148).

Instrument (120) lacks a clamp arm in this example, such that instrument (120) is configured for use as an ultrasonic scalpel for simultaneously slicing and cauterizing tissue. Instead, end effector (150) merely consists of ultrasonic blade (152) that may be used for simultaneously slicing and cauterizing tissue. In some alternative versions, including but not limited to those described below, end effector (150) may include a clamp arm that may be used to compress tissue against ultrasonic blade (152) to assist in grasping, sealing, and/or cutting the tissue. Such a clamp arm may be removably coupled to instrument (120). By way of example only, a removable clamp arm may be provided in accordance with at least some of the teachings of U.S. patent application Ser. No. 14/488,330, entitled "Ultrasonic Surgical Instrument with Removable Clamp Arm," filed Sep. 17, 2014, published as U.S. Pub. No. 2016/0074060 on Mar. 17, 2016, the disclosure of which is incorporated by reference herein. Alternatively, a clamp arm may be provided in any other suitable fashion.

B. Exemplary Handle Assembly

Figure 5:
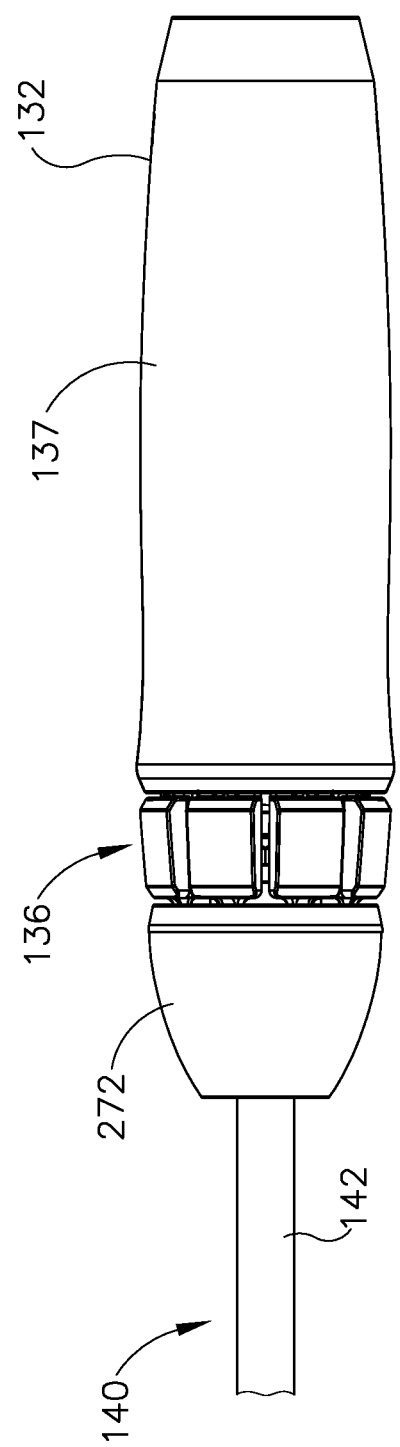
FIG. 5 depicts a side elevational view of a handle assembly of the instrument of FIG. 2.
Figure 6:
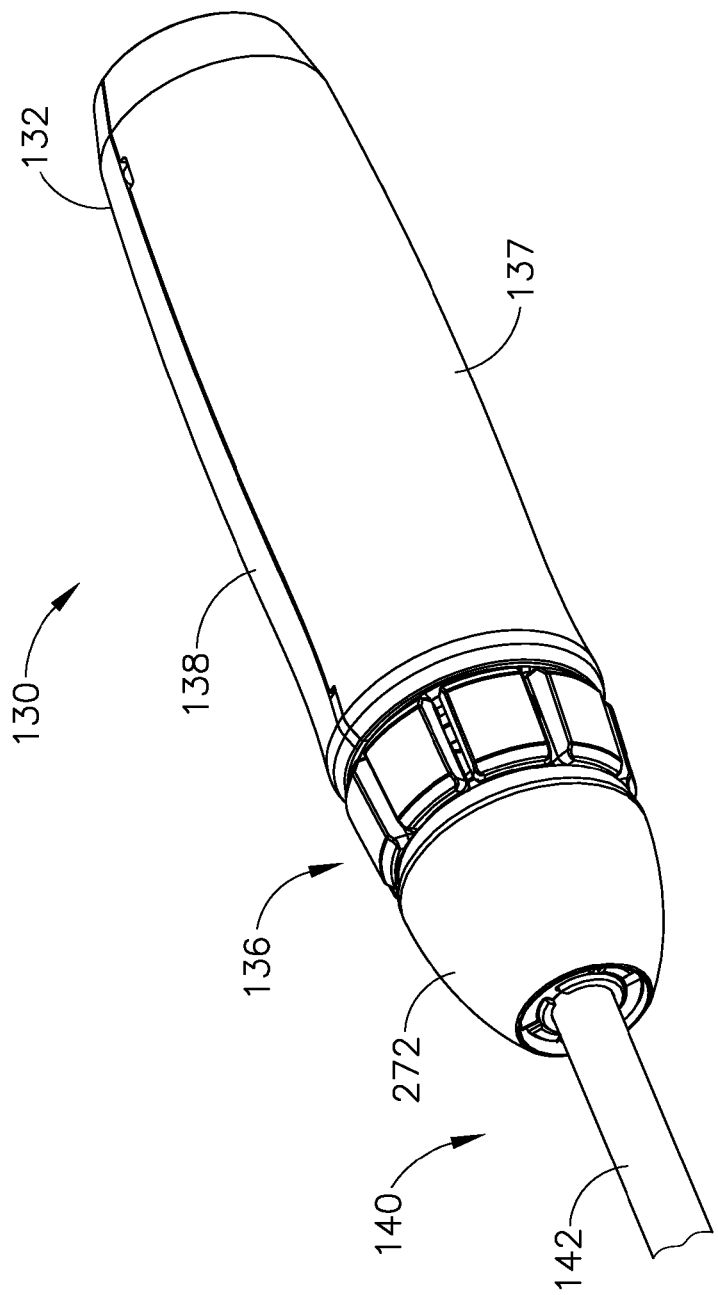
FIG. 6 depicts a perspective view of the handle assembly of FIG. 5.
Figure 7:
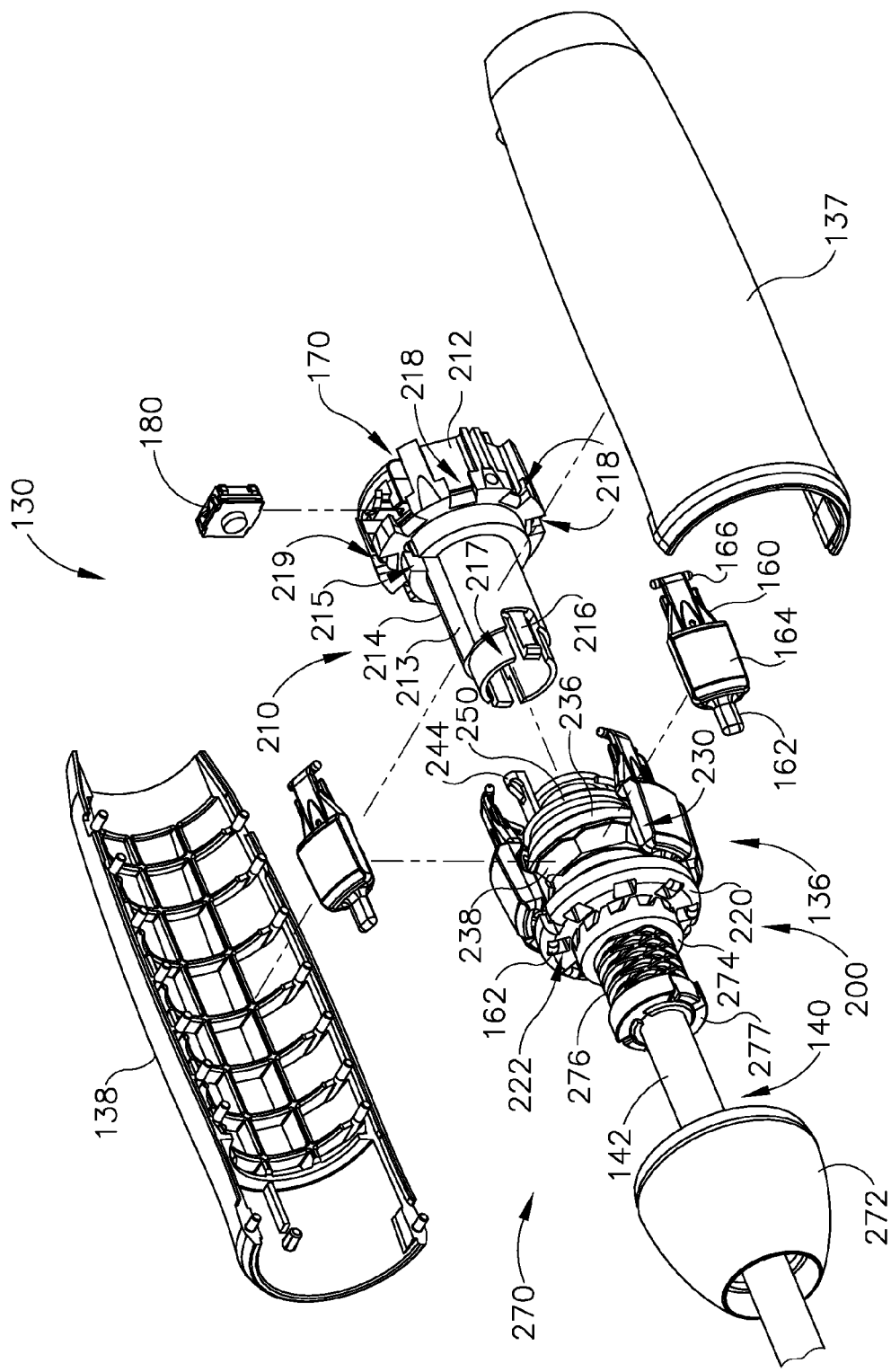
FIG. 7 depicts a partially exploded perspective view of the handle assembly of FIG. 5.

As best seen in FIGS. 5-7, handle assembly (130) comprises a tubular elongate body (132) including a plurality of buttons (136). Elongate body (132) is configured to permit a user to grip handle assembly (130) from a variety of positions. By way of example only, handle assembly (130) may be shaped to be grasped and manipulated in a pencil-grip arrangement, in a screwdriver-grip arrangement, and/or in any other suitable fashion. Handle assembly (130) of the present example comprises mating housing portions (137) and (138), though it should be understood that handle assembly (130) may alternatively comprise just a single housing component. Housing portions (137, 138) may be constructed from a durable plastic, such as polycarbonate or a liquid crystal polymer. It is also contemplated that housing portions (137, 138) may alternatively be made from a variety of materials or combinations of materials, including but not limited to other plastics, ceramics, and/or metals, etc.

In the present example, body (132) of handle assembly (130) includes a proximal end, a distal end, and a cavity (139) extending longitudinally therein. Cavity (139) is configured to accept a switch assembly (170), an actuation assembly (200), and at least a portion of ultrasonic transducer assembly (126). In the present example, the distal end of transducer (126) threadably attaches to the proximal end of waveguide (148), though any other suitable type of coupling may be used. Electrical contacts of transducer (126) also interface with switch assembly (170) to provide the operator with finger-activated controls on surgical instrument (120). Transducer (126) of the present example includes two conductive rings (not shown) that are securely disposed within the body of transducer (126). By way of example only, such conductive rings and/or other features of transducer (126) may be provided in accordance with at least some of the teachings of U.S. Pat. No. 8,152,825, entitled "Medical Ultrasound System and Handpiece and Methods for Making and Tuning," issued Apr. 10, 2012, the disclosure of which is incorporated by reference herein.

Switch assembly (170) provides an electro-mechanical interface between buttons (136) of handle assembly (130) and generator (12) via transducer (126). Switch assembly (170) of the present example comprises a contact switch (180) and a switch housing (182). Actuation assembly (200) is supported within handle assembly (130) by way of corresponding supporting mounts on actuation assembly (200) and body (132). As will be discussed in more detail below, switch housing (182) is supported within actuation assembly (200). Contact switch (180) comprises an electrical contact switch in this example, that when contact switch (180) is depressed, contact switch (180) provides an electrical signal to generator (12) and/or closes a circuit between generator (12) and transducer (126). By way of example only, various components of switch assembly (170) may interface with transducer (126) via ring conductors of transducer (126), which are in turn connected to conductors in cable (14) that connects to generator (12). Thus, when contact switch (180) is actuated, generator (12) activates transducer (126) to generate ultrasonic vibrations.

1. Exemplary Actuation Assembly

Figure 11:
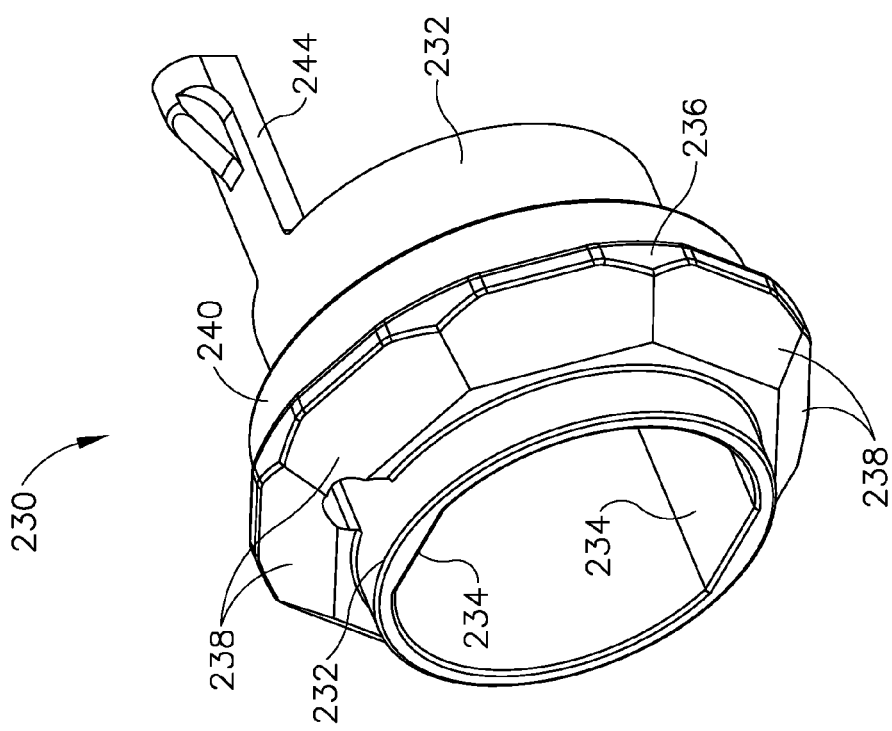
FIG. 11 depicts a perspective view of an actuation sled of the handle assembly of FIG. 5.
Figure 12:
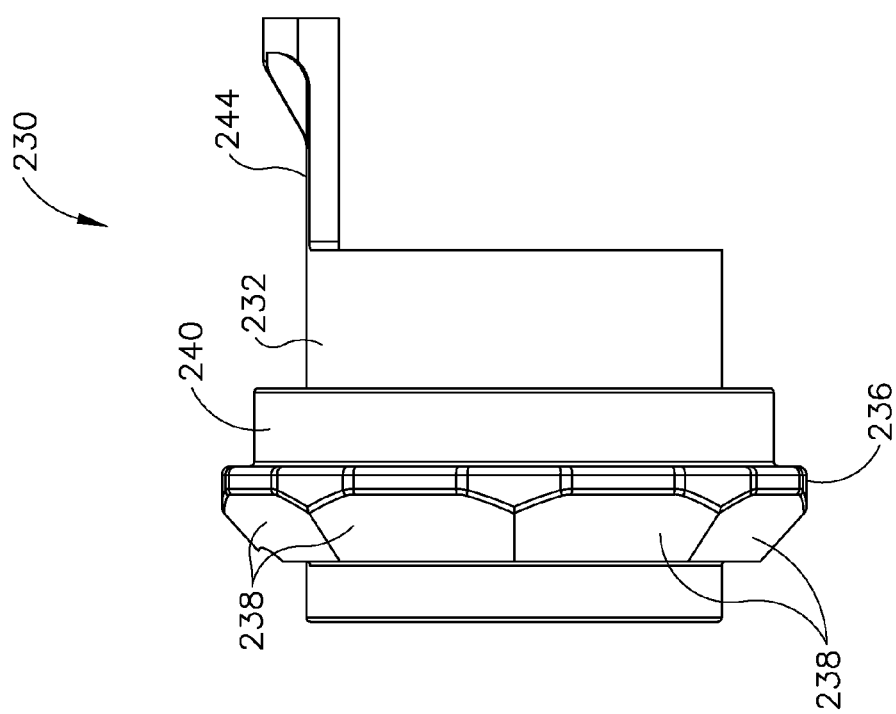
FIG. 12 depicts a side elevational view of the actuation sled of FIG. 11.
Figure 13:
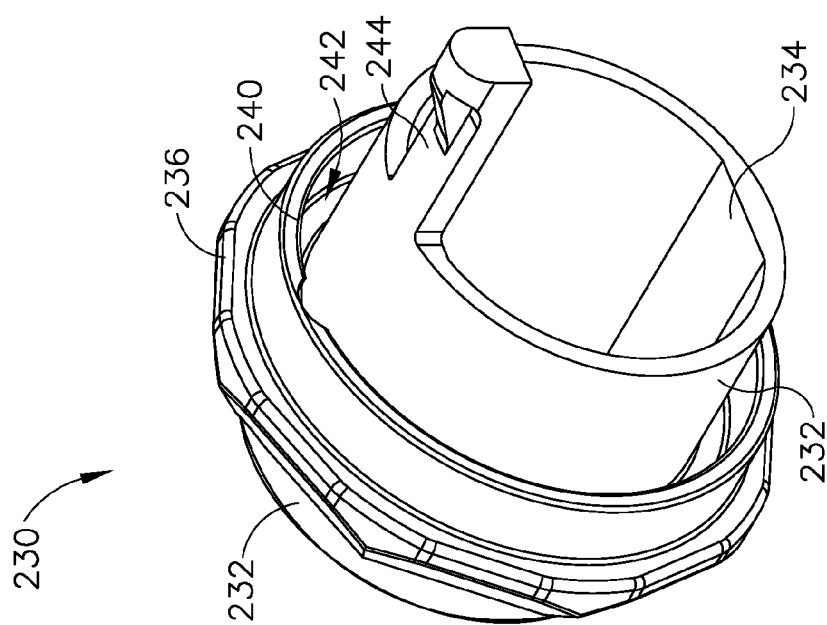
FIG. 13 depicts another perspective view of the actuation sled of FIG. 11.

As best seen in FIGS. 7 and 16A-17B, actuation assembly (200) of the present example comprises a proximal elongate rack (210), a distal annular rack (220), a sled (230), and plurality of buttons (136). As best seen in FIGS. 11-13, sled (230) comprises a hollow cylindrical body (232). A pair of flat surfaces (234) are formed in opposing surfaces (e.g. a top surface and a bottom surface) of an interior of body (232). As will be discussed in more detail below, flat surfaces (234) are configured to prevent rotation of sled (230) within handle assembly (130). Sled (230) further comprises an annular projection (236) extending outwardly from an exterior surface of body (232). A plurality of angled camming surfaces (238) are formed within a distal surface of annular projection (236). Camming surfaces (238) are disposed about annular projection (238) in an angularly spaced array. As will be discussed in more detail below, buttons (136) are configured to engage camming surfaces (238) to thereby cause proximal longitudinal translation of sled (230) within handle assembly (130). A cylindrical projection (240) extends proximally from a proximal surface of annular projection (236). A cylindrical gap (242) is defined between an interior surface of cylindrical projection (240) and the exterior surface of body (232). Cylindrical gap (242) is configured to receive a spring (250), which is configured to bias sled (230) distally. Sled (230) further comprises an elongate arm (244) extending proximally from a proximal end of body (232). As will be discussed in more detail below, a proximal end of arm (244) is configured to engage contact switch (180) upon proximal longitudinal translation of sled (230).

As shown in FIGS. 7 and 16A-17B, elongate rack (210) comprises annular base (212) and a hollow cylindrical portion (214) extending distally therefrom. Hollow cylindrical portion (214) is configured to slidably receive sled (230) such that sled (230) is operable to translate longitudinally between a proximal position and a distal position along hollow cylindrical portion (214). A pair of flat surfaces (213) are formed in opposing regions (e.g. a top surface and a bottom surface) of an exterior surface of hollow cylindrical portion (214). Flat surfaces (213) of hollow cylindrical portion (214) are configured to engage flat surfaces (234) of sled (230) to thereby prevent rotation of sled (230) about hollow cylindrical portion (214). A distal portion of hollow cylindrical portion (214) comprises a circular recess (217) with a pair of resilient tabs (216) formed therein. Ring shaped-rack (220) is configured to be received by hollow cylindrical portion (214) about recess (217) and held in place by engagement with resilient tabs (216) such that annular rack (220) is translatably and rotatably secured to elongate rack (210). Thus, it should be appreciated that sled (230) is operable to translate longitudinally along hollow cylindrical portion (214) between annular base (212) and annular rack (220). Spring (250) is disposed about hollow cylindrical portion (214) between annular base (212) and sled (230). A distal portion of spring (250) is disposed within cylindrical gap (242) of sled (230) and bears upon sled (230) so as to urge sled (230) distally. A proximal end of spring (250) is grounded against annular base (212).

As shown in FIG. 7, annular base (212) is configured to receive and serve as a housing for switch assembly (170), including contact switch (180). Annular base (212) defines an opening (215). Sled (230) is oriented such that arm (244) of sled (230) is aligned with opening (215). Thus, as sled (230) translates longitudinally along hollow cylindrical portion (214), arm (244) passes into and through opening (215) as will be discussed in more detail below. Also as will be discussed in more detail below, contact switch (180) is positioned adjacent to opening (215) such that as arm (244) passes into and through opening (215), a proximal end of arm (244) engages contact switch (180) to thereby provide an electrical signal to generator (12) and/or to close a circuit between generator (12) and transducer (126).

Figure 14:
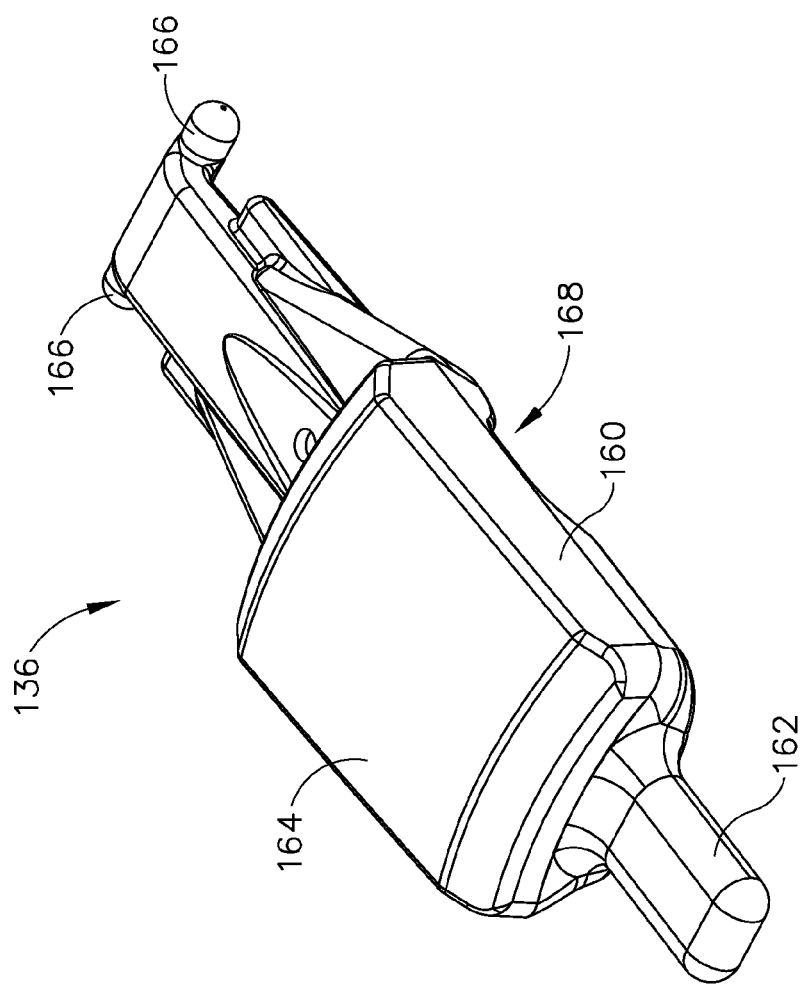
FIG. 14 depicts a perspective view of a button of the handle assembly of FIG. 5.
Figure 15:
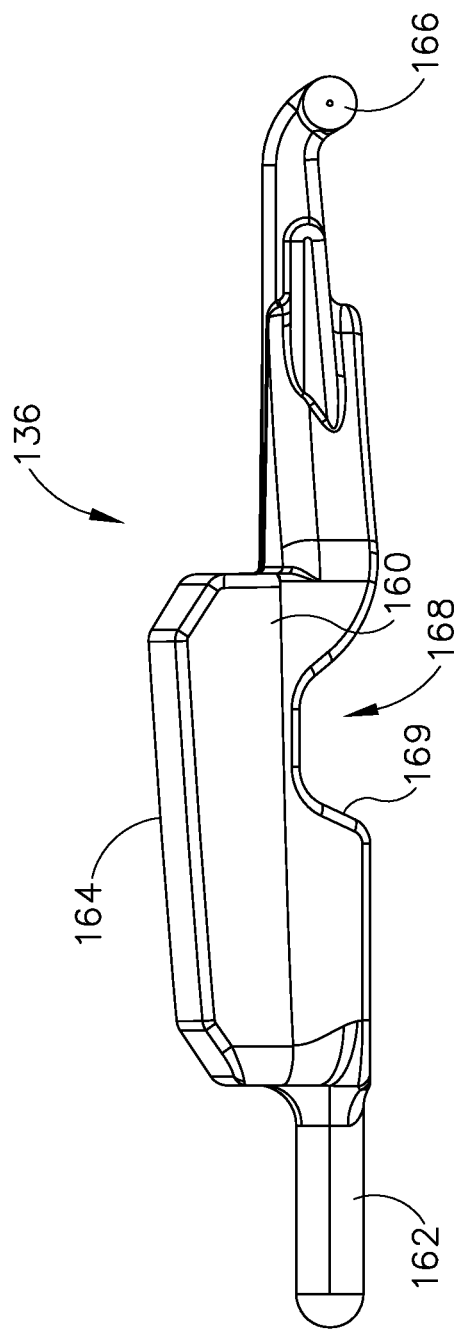
FIG. 15 depicts a side elevational view of the button of FIG. 14.

As best seen in FIGS. 14-15, each button (136) comprises an elongate body (160) having an arm (162) extending distally from a distal end of body (160), a finger/thumb pad (164) formed in a top surface of body (160), and a pair of cylindrical projections (166) extending transversely from a proximal end of body (160). Body (160) further comprises a recess (168) formed in a bottom surface of body (160). Recess (168) comprises an angular camming surface (169). As will be discussed in more detail below, radially inwardly movement of button (136) causes camming surface (169) to engage camming surface (238) of sled (230), thereby driving sled (230) proximally.

Referring back to FIG. 7, annular base (212) of elongate rack (210) comprises a plurality of slots (218), which are disposed about annular base (212) in an angularly spaced array. Each slot (218) comprises a pair of recesses (219) formed in opposing side surfaces of slots (218). Recesses (219) are configured to rotatably receive cylindrical projections (166) of buttons (136) such that button (136) is pivotable about cylindrical projections (166) within slots (218) toward and away from a center of actuation assembly (200). In other words, projections (166) serve as pivot pins for each button (136). As best seen in FIGS. 7-8 and 10A-10B, annular rack (220) comprises a plurality of openings (222) disposed about annular rack (220) in an angular array substantially similar to that of slots (218). Openings (222) are configured to slidably receive arms (162) of buttons (136) such that each arm (162) is radially translatable within a respective opening (222). It should be appreciated that inner surfaces of openings (222) will restrict the radial range through which buttons (136) are able to travel within slots (218). The angular arrangement of slots (218) and openings (222) is sufficiently similar to the angular arrangement of camming surfaces (238) of sled (230) such that each button (136) is configured to align with a respective camming surface (238) of sled (230).

Figure 16A:
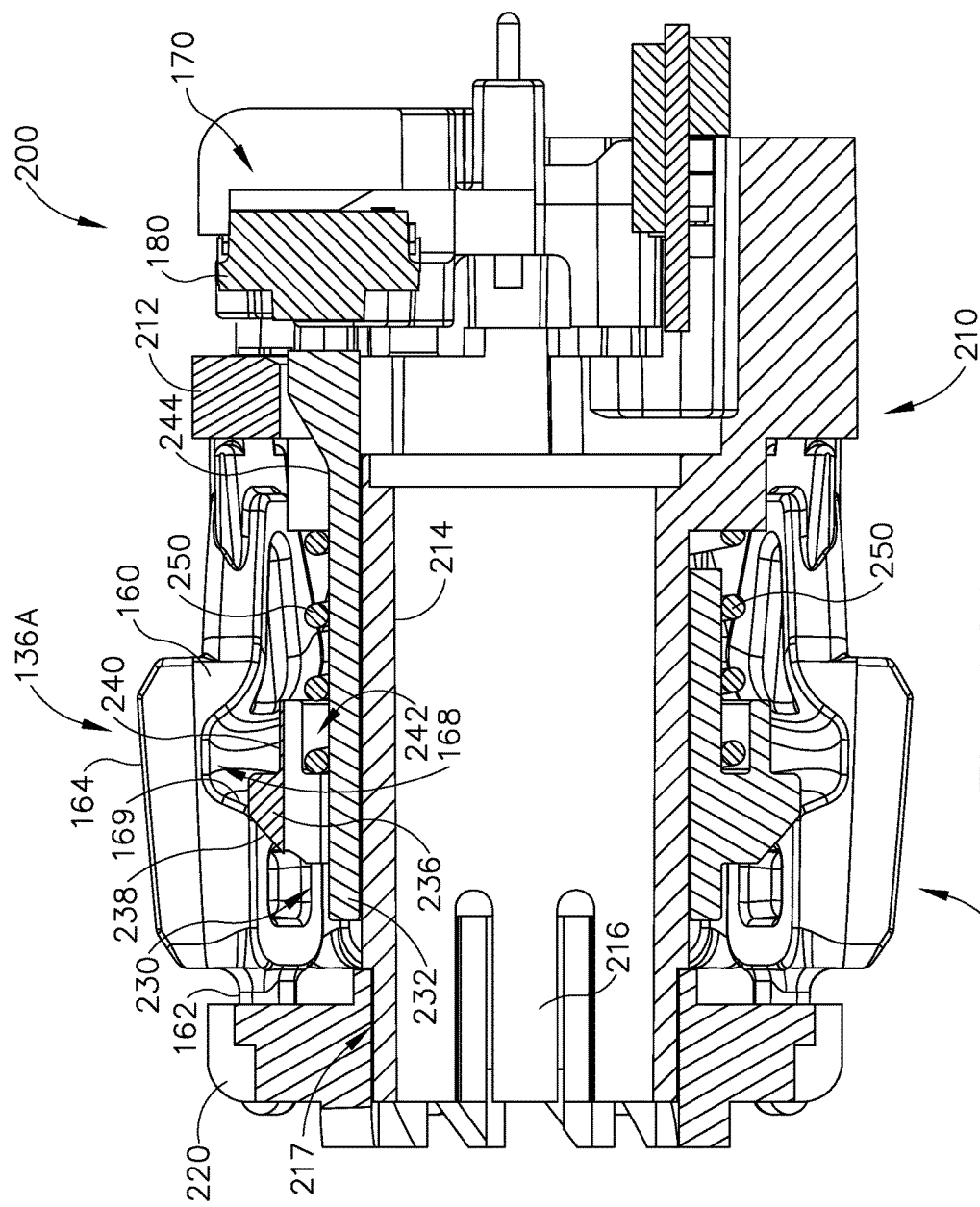
FIG. 16A depicts a cross-sectional side view of an actuation assembly of the handle assembly of FIG. 5, with the button of FIG. 14 in a first radial position, and with the actuation sled of FIG. 11 in a first longitudinal position.

FIGS. 16A-17B show the operation of actuation assembly (200). As shown in FIGS. 16A and 17A, in an initial state, a button (136A) of buttons (136) is in a substantially horizontal position. Button (136A) is arbitrarily selected in this example. It should be understood that each button (136) will operate just like button (136A) as described in this example. In the substantially horizontal position of the initial state shown in FIGS. 16A and 17A, camming surface (169) of button (136A) rests upon camming surface (238) of sled (230). Sled (230), however, is held in a distal position by the distal bias of spring (250). Also in this state, while the proximal end of arm (244) is within opening (215) of annular base (212), the proximal end of arm (244) is not in contact with contact switch (180). In fact, a slight gap exists between arm (244) and contact switch (180) in this position. Thus, contact switch (180) is not actuated, such that transducer (126) and ultrasonic blade (152) are in a non-activated state.

Figure 16B:
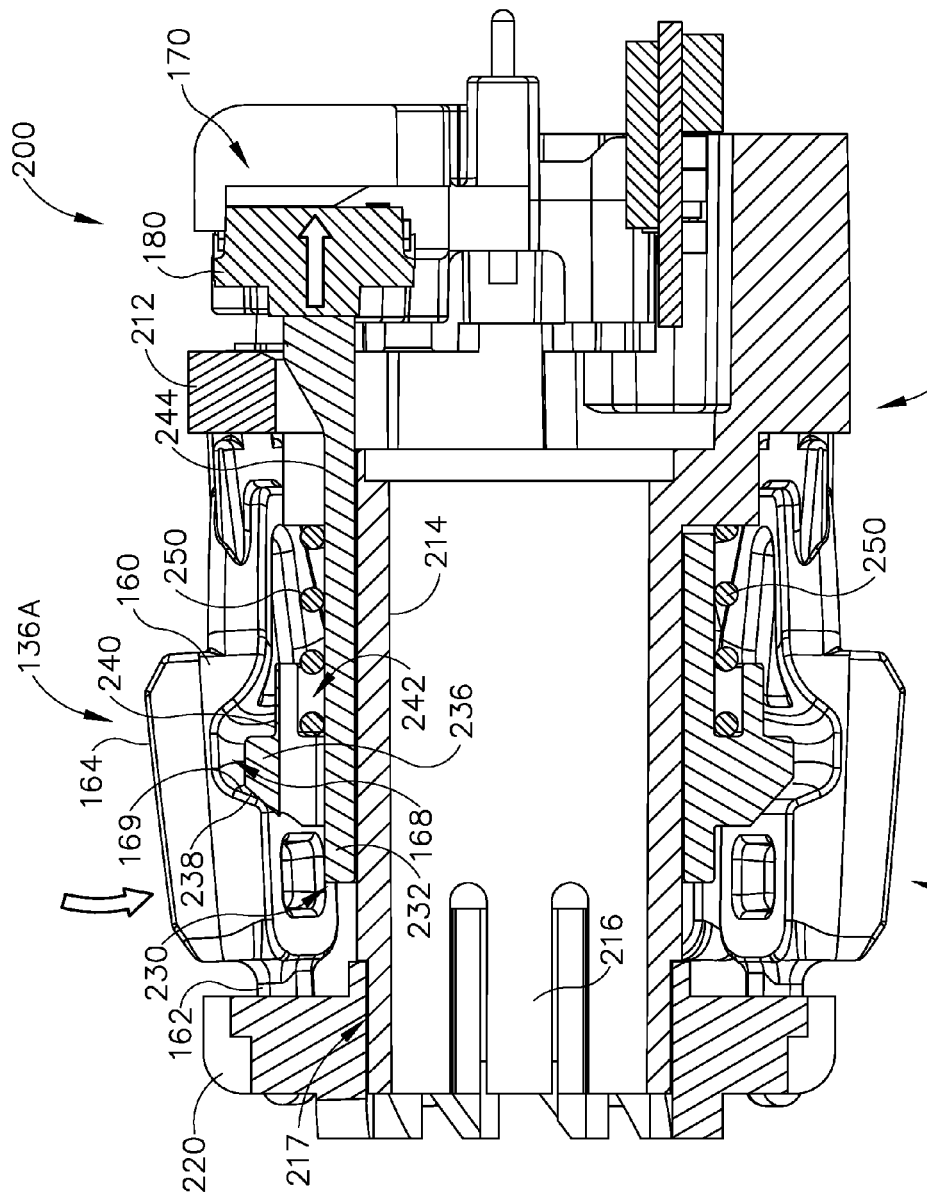
FIG. 16B depicts a cross-sectional side view the actuation assembly of FIG. 16A, with the actuation sled of FIG. 11 moved into a second longitudinal position by movement of the button of FIG. 14 into a second radial position to thereby actuate the instrument of FIG. 2.
Figure 17A:
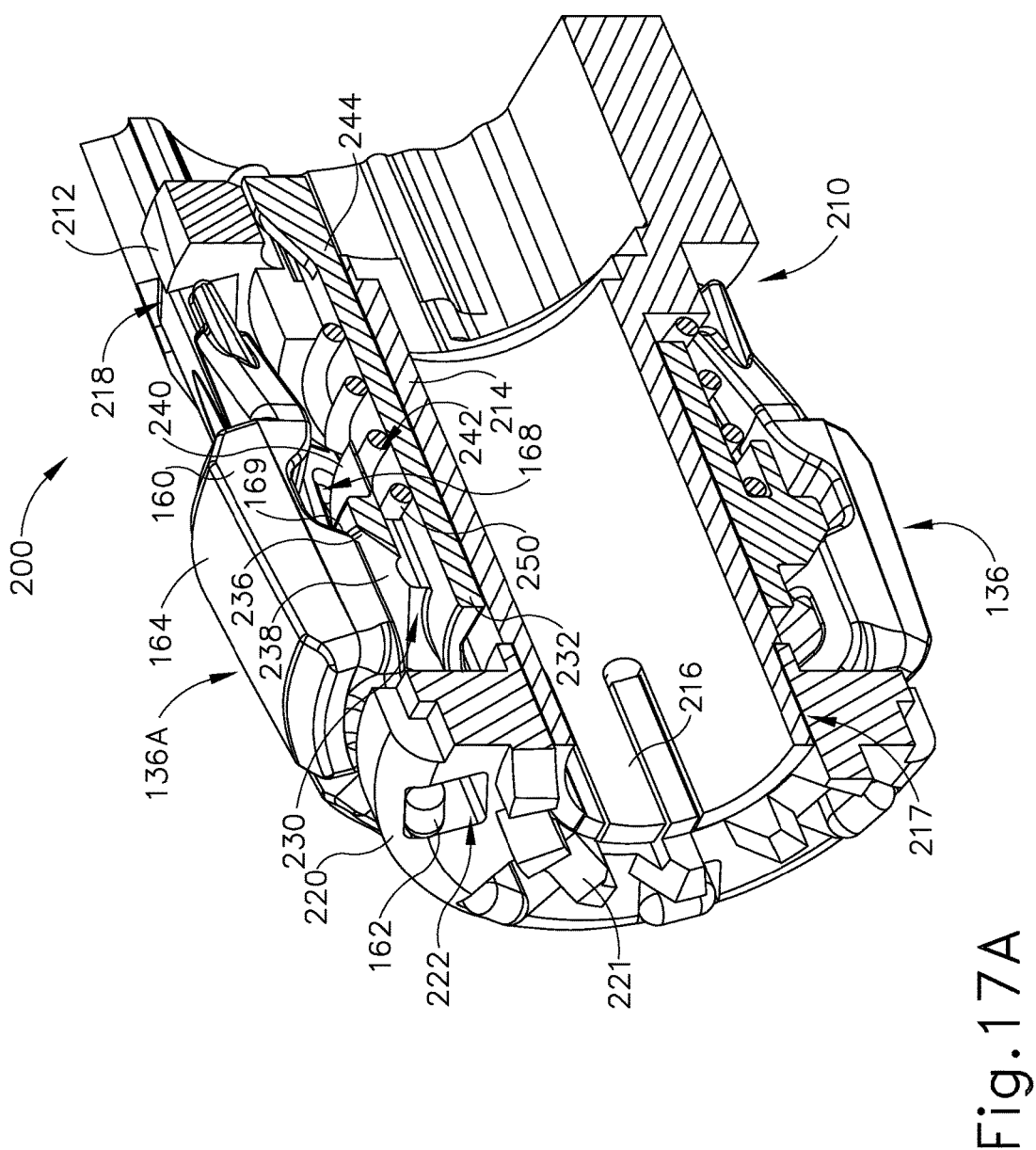
FIG. 17A depicts a cross-sectional perspective view of the actuation assembly of FIG. 16A, with the button of FIG. 14 in a first radial position, with the actuation sled of FIG. 11 in a first longitudinal position, and with a switch assembly removed for clarity.
Figure 17B:
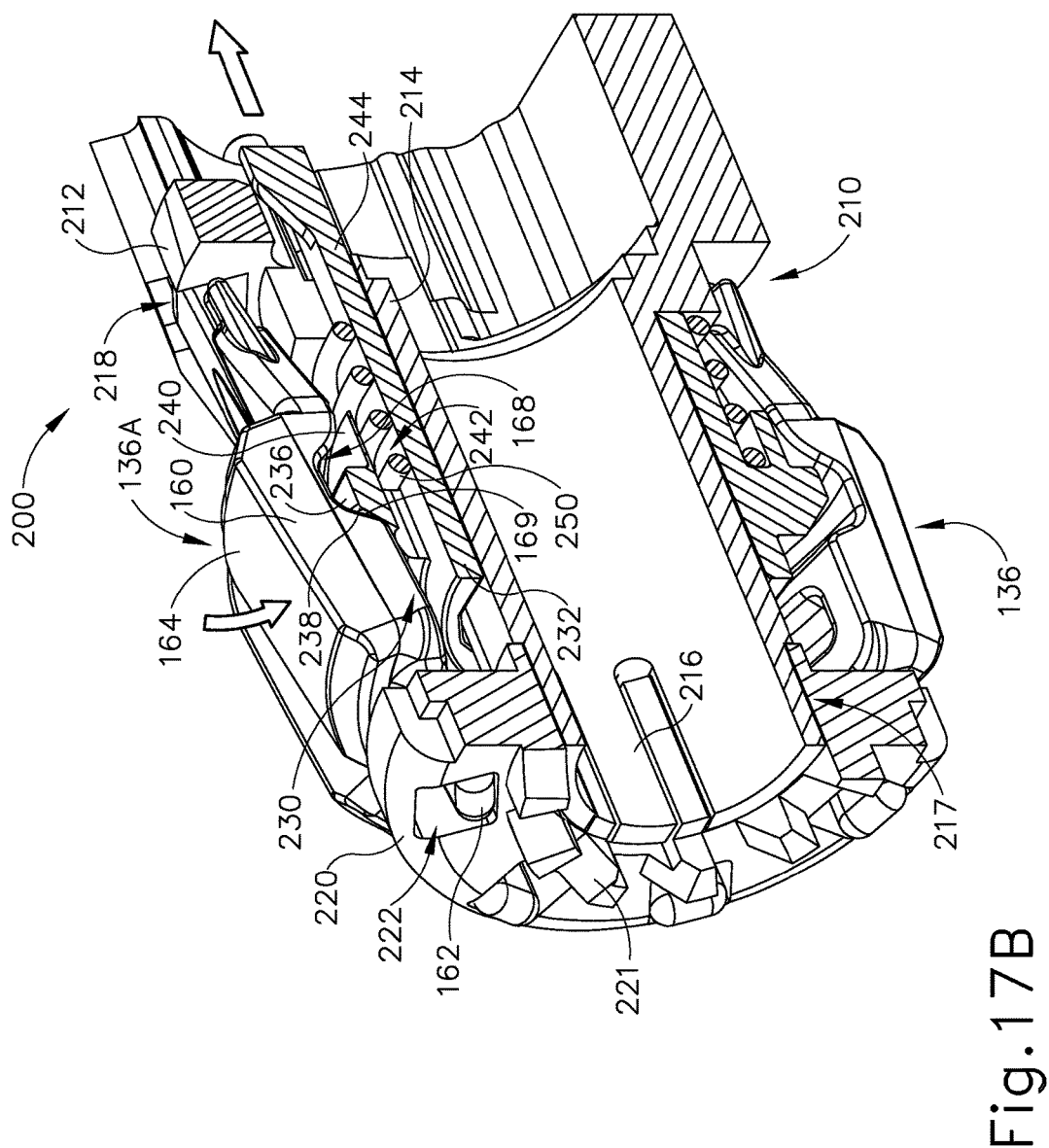
FIG. 17B depicts a cross-sectional perspective view the actuation assembly of FIG. 16A, with the actuation sled of FIG. 11 moved into a second longitudinal position by movement of the button of FIG. 14 into a second radial position to thereby actuate the instrument of FIG. 2, and with the switch assembly removed for clarity.

As shown in FIGS. 16B and 17B, as an operator drives button (136A) radially inwardly (i.e., by depressing button (136A)), button (136A) pivots about cylindrical projections (166) within slots (218) into the position shown. As button (136A) is driven radially inwardly, camming surface (169) of button (136A) bears upon camming surface (238) of sled (230) to thereby drive sled longitudinally proximally along hollow cylindrical portion (214) by overcoming the distal bias of spring (250). As sled (230) is driven longitudinally proximally, the distal end of arm (244) engages and depresses contact switch (180). This actuation of contact switch (180) provides activation of transducer (126) by generator (12), thereby activating ultrasonic blade (152). The operator may hold button (136A) in a depressed state to maintain activation of transducer (126) and ultrasonic blade (152). When the operator releases button (136A), the distal bias of spring (250) with drive sled (230) longitudinally distally to thereby drive button (136A) back the substantially horizontal position shown in FIGS. 16A and 17A via contact between camming surface (169) of button (136A) and camming surface (238) of sled (230). It should be appreciated that because each button (136) is aligned with a respective camming surface (238) of sled (230), the operator may use any button (136) of the plurality of buttons (136) to actuate contact switch (180).

2. Exemplary Torque Assembly

As mentioned above, ultrasonic transducer (126) is threadably coupled with waveguide (148) of shaft assembly (140) in this example. As best seen in FIGS. 7-10B, the proximal end of shaft assembly (140) comprises a torquing mechanism (270) that is configured to permit coupling of waveguide (148) with transducer (126); while at the same time limiting the amount of torque that can be applied to shaft assembly (140) and/or transducer (126). Torquing mechanism (270) comprises a rotation knob (272), an annular rack (274), and a wave spring (276). Rotation knob (272) is rotatably disposed about shaft assembly (140) such that rotation knob (272) may be rotated about shaft assembly (140). As best seen in FIG. 9, rotation knob (272) comprises a pair of elongate projections (273) extending inwardly from opposing interior surfaces (e.g. a top surface and a bottom surface) of rotation knob (272).

Figure 8:
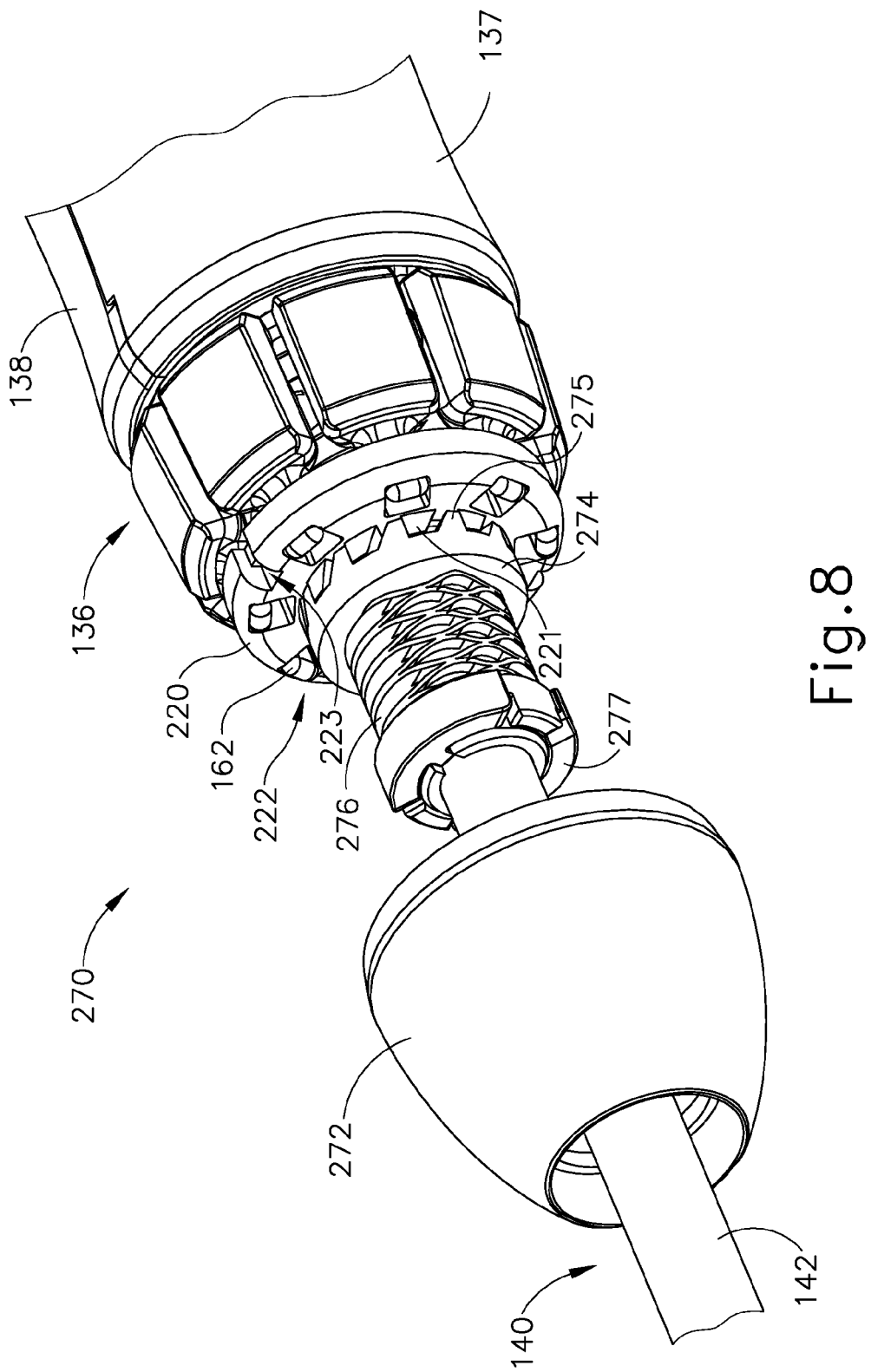
FIG. 8 depicts a partially exploded perspective view of a distal end of the handle assembly of FIG. 5.
Figure 9:
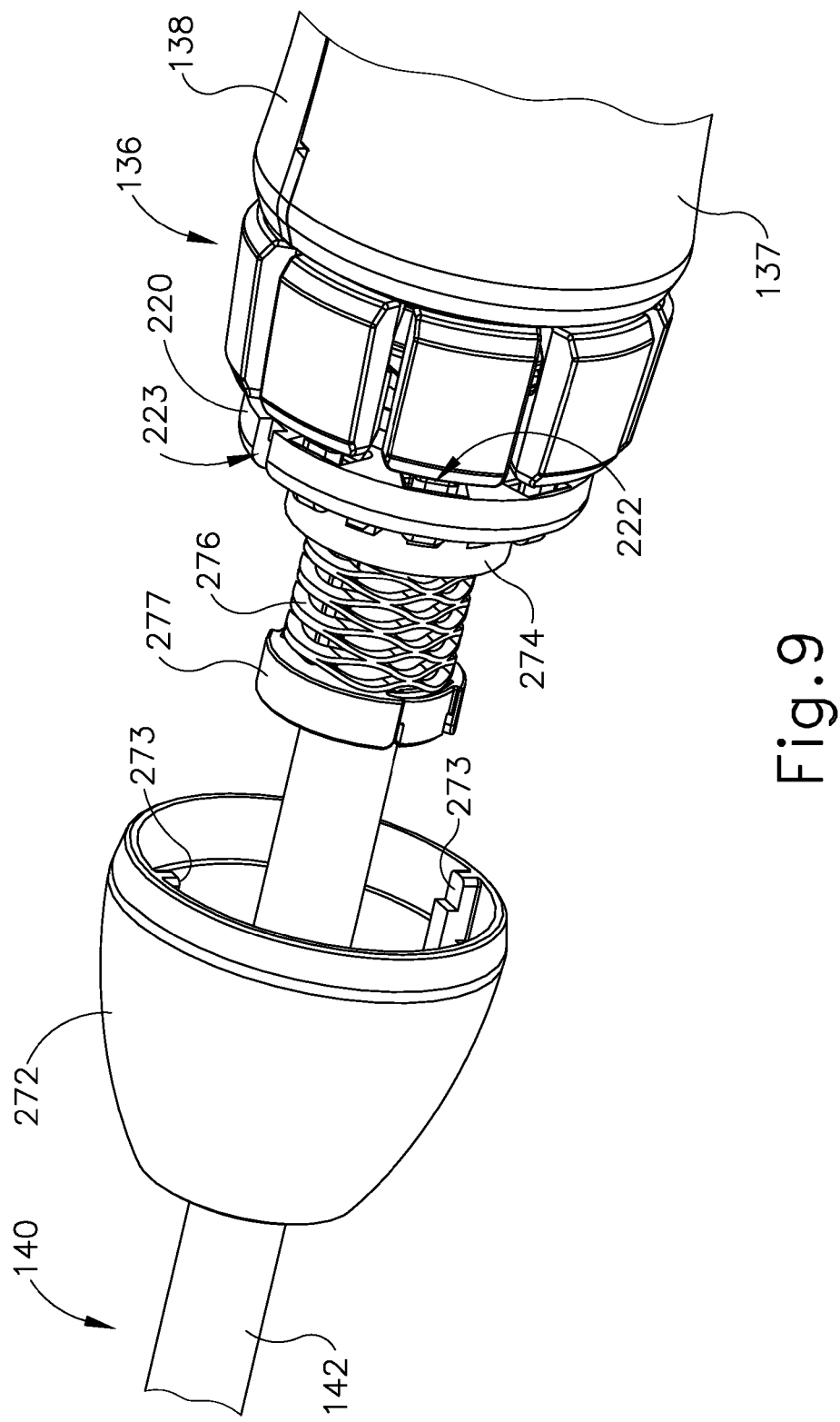
FIG. 9 depicts another partially exploded perspective view of the distal end of the handle assembly of FIG. 5.

As best seen in FIG. 8, annular rack (220) of actuation assembly (200) comprises a pair of slots (223) formed in opposing exterior surfaces (e.g. a top surface and a bottom surface) of annular rack (220). Slots (223) of annular rack (220) are configured to receive projections (273) of rotation knob (272) in a key-keyway relationship, such that rotation of rotation knob (272) causes concurrent rotation of annular rack (220). Because of the engagement between annular rack (220) and the remainder of actuation assembly (200), rotation of annular rack (220) causes concurrent rotation of actuation assembly (200). Further, because of the engagement between actuation assembly (200) and handle assembly (130), rotation of actuation assembly (200) causes concurrent rotation of handle assembly (130). Thus, rotation knob (272), annular rack (220), and handle assembly (130) rotate together unitarily in this example.

Figure 10A:
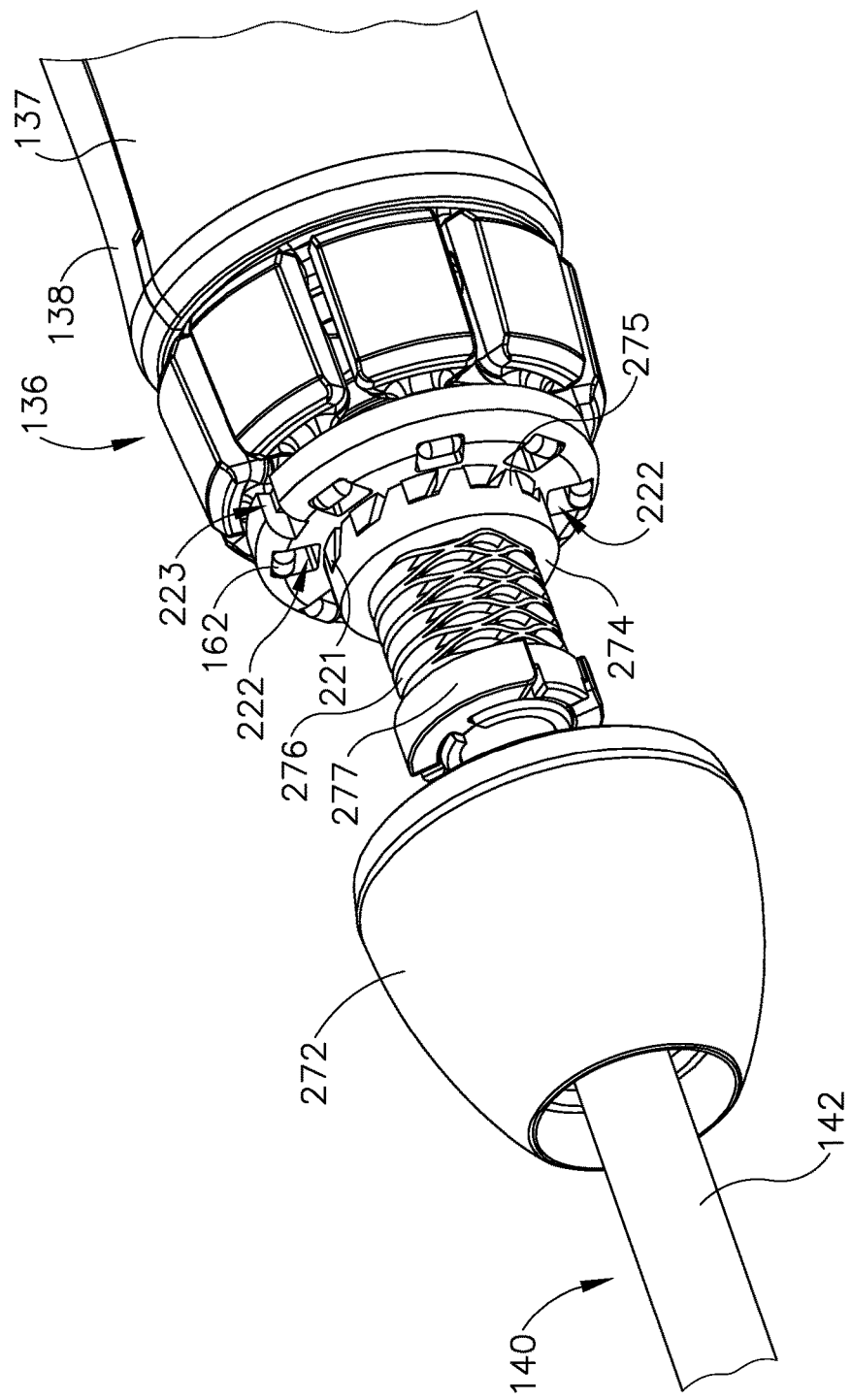
FIG. 10A depicts a partially exploded perspective view of the distal end of the handle assembly of FIG. 5, with a torquing mechanism in a non-slip position.
Figure 10B:
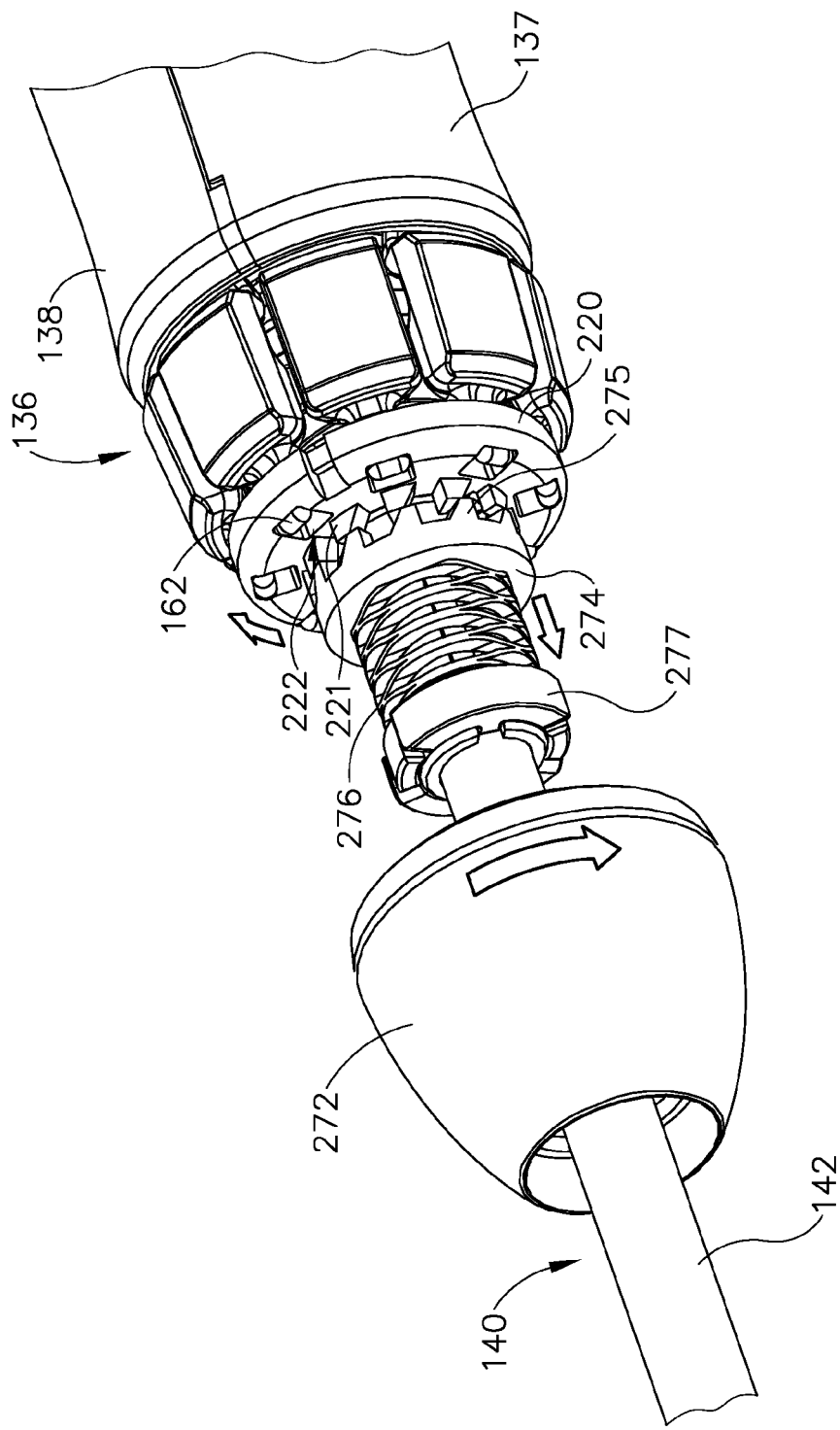
FIG. 10B depicts a partially exploded perspective view of the distal end of the handle assembly of FIG. 5, with the torquing mechanism of FIG. 10A in a slipping position.

Annular rack (274) of torquing mechanism (270) is slidably disposed about shaft assembly (140) such that annular rack (274) may be longitudinally translated relative to shaft assembly (140). However, annular rack (274) is coupled with shaft assembly (140) such that rotation of annular rack (274) causes concurrent rotation of shaft assembly (140). In particular, annular rack (274) comprises a pair of elongate projections (not shown) that are engaged within a pair of complementary elongate slots (not shown) of shaft assembly (140) such that annular rack (274) may translate longitudinally relative to shaft assembly (140); and such that rotation of annular rack (274) causes concurrent rotation of shaft assembly (140). Annular rack (274) comprises a plurality of teeth (275) arranged in a circular pattern and projecting proximally from a proximal face of annular rack (274). As best seen in FIGS. 8 and 10A-10B (in which rotation knob (272) is shown in a distal position to reveal internal components of torquing assembly (270)), annular rack (220) of actuation assembly (200) also comprises a plurality of teeth (221), which are arranged in a circular pattern and project distally from a distal face of annular rack (220). Teeth (275) of annular rack (274) are configured to engage teeth (221) of annular rack (220). In particular, as shown in FIGS. 10A-10B, teeth (221) and teeth (275) each comprise angled camming surfaces that engage one another. Engagement between these camming surfaces causes concurrent rotation of annular rack (274) with annular rack (220), at least to a certain degree as described below with reference to FIGS. 10A-10B.

Wave spring (276) is positioned between annular rack (274) and a distal ring (277). Distal ring (277) is configured to slide longitudinally relative to annular rack (274) and shaft assembly (140). Distal ring (277) is also configured to engage an interior portion of rotation knob (272). When rotation knob (272) is secured to annular rack (220), wave spring (276) is slightly compressed between distal ring (277) and annular rack (274), such that wave spring (276) resiliently biases annular rack (274) and shaft assembly (140) proximally relative to rotation knob (272). Shaft assembly (140) is thus resiliently biased proximally relative to handle assembly (130). This proximal bias of shaft assembly (140) ensures an initial contact between a threaded stud (127) at the distal end of transducer (126) and a complementary threaded recess (not shown) at the proximal end of waveguide (148) as transducer (126) is inserted into handle assembly (130).

During an initial stage of assembly of instrument (120), an operator may first align transducer (126) along the longitudinal axis shared by handle assembly (130) and shaft assembly (140), then insert transducer (126) into the proximal end of handle assembly (130). As noted above, wave spring (276) will ensure initial contact between threaded stud (127) at the distal end of transducer (126) and the complementary threaded recess at the proximal end of waveguide (148) as transducer (126) is inserted into handle assembly (130). The operator may then grasp transducer (126) with one hand and grasp either handle assembly (130) or rotation knob (272) with the other hand. Once these components are firmly grasped, the operator may rotate handle assembly (130) or rotation knob (272) relative to transducer (126) about the longitudinal axis. As noted above and as shown in FIG. 10A, teeth (275) of annular rack (274) engage teeth (221) of annular rack (220) at this stage, such that handle assembly (130), rotation knob (272), and shaft assembly (140) will all rotate together concurrently relative to transducer (126).

As handle assembly (130) and shaft assembly (140) rotate relative to transducer (126), waveguide (148) is threaded onto stud (127) of transducer (126). As noted above, teeth (221) engage teeth (275) through angled camming surfaces. These angled camming surfaces are configured such that annular rack (220) may transfer torque to annular rack (274), and thereby screw threaded stud (127) of transducer (126) into the threaded recess of waveguide (148), until annular rack (274) encounters a predetermined resistance to further rotation. Such resistance to further rotation is caused by threaded stud (127) of transducer (126) being screwed into the threaded recess of waveguide (148) at a predetermined torque level. When annular rack (274) experiences the predetermined amount of resistance, the angled camming surfaces causes annular rack (274) to translate longitudinally distally by overcoming the proximal bias of wave spring (276). When annular rack (274) translates distally as shown in FIG. 10B, teeth (221) disengage from teeth (275), such that rotation of rotation knob (272) and handle assembly (130) no longer causes rotation of shaft assembly (140). Thus, it should be understood that torquing assembly (270) restricts the amount of torque by which waveguide (148) may be coupled with transducer (126) by acting as a slipping clutch. The maximum torque level may be pre-set by selecting particular angles of the camming surfaces of teeth (221, 275) and/or by adjusting other structural characteristics of torquing assembly (270). Various suitable levels of torque that may be effectively established by torquing assembly (270) will be apparent to those of ordinary skill in the art in view of the teachings herein.

It should be understood that the above described example of torquing mechanism (270) is merely illustrative. Torquing mechanism (270) may be constructed and operable in any other suitable fashion. By way of example only, torquing mechanism (270) may be constructed and operable in accordance with at least some of the teachings of U.S. patent application Ser. No. 14/087,383, entitled "Features for Coupling Surgical Instrument Shaft Assembly with Instrument Body," filed on Nov. 22, 2013, published as U.S. Pub. No. 2015/0148830 on May 28, 2015, the disclosure of which is incorporated by reference herein. Other suitable ways in which torquing mechanism (270) may be constructed and operable will be apparent to those of ordinary skill in the art in view of the teachings herein.

Instrument (120) may further be configured and operable in accordance with the teachings of U.S. Pub. No. 2008/0200940, entitled "Ultrasonic Energy Device for Cutting and Coagulating," published Aug. 21, 2008, the disclosure of which is incorporated by reference herein. Alternatively, instrument (120) may be provided with a variety of other components, configurations, and/or types of operability as will be apparent to those of ordinary skill in the art in view of the teachings herein.

In addition to or in lieu of being constructed in accordance with the above teachings, at least part of instrument (120) may be constructed and operable in accordance with at least some of the teachings of U.S. Pat. No. 5,322,055; U.S. Pat. No. 5,873,873; U.S. Pat. No. 5,980,510; U.S. Pat. No. 6,283,981; U.S. Pat. No. 6,309,400; U.S. Pat. No. 6,325,811; U.S. Pat. No. 6,423,082; U.S. Pat. No. 6,783,524; U.S. Pat. No. 8,057,498; U.S. Pat. No. 8,461,744; U.S. Pub. No. 2006/0079874; U.S. Pub. No. 2007/0191713; U.S. Pub. No. 2007/0282333; U.S. Pub. No. 2008/0200940; U.S. Pub. No. 2008/0234710, now U.S. Pat. No. 8,911,460; U.S. Pub. No. 2010/0069940, now U.S. Pat. No. 9,023,071; U.S. Pub. No. 2012/0112687, now U.S. Pat. No. 9,381,058; U.S. Pub. No. 2012/0116265; U.S. Pub. No. 2014/0005701, now U.S. Pat. No. 9,393,037; U.S. Pub. No. 2014/0114334, now U.S. Pat. No. 9,095,367; and/or U.S. Pat. App. No. 61/410,603. The disclosures of each of the foregoing patents, publications, and applications are incorporated by reference herein. Additional merely illustrative variations for instrument (120) will be apparent to those of ordinary skill in the art in view of the teachings herein. It should be understood that the below described variations may be readily applied to instrument (120) described above and any of the instruments referred to in any of the references that are cited herein, among others.

C. Exemplary Alternative Actuation Assemblies

In some instances, it may be desirable to provide a version of instrument (120) with an alternative form of actuation assembly (200). In particular, it may be desirable to provide a version of instrument (120) with an actuation assembly that utilizes radially inward movement of buttons (136) to directly actuate contact switch (180) via transverse movement and/or pivotal movement. Various examples of alternative actuation assemblies are described in greater detail below; while further examples will be apparent to those of ordinary skill in the art in view of the teachings herein. It should be understood that the various actuation assemblies described below may be readily incorporated into instrument (120) in place of actuation assembly (200).

Figure 18:
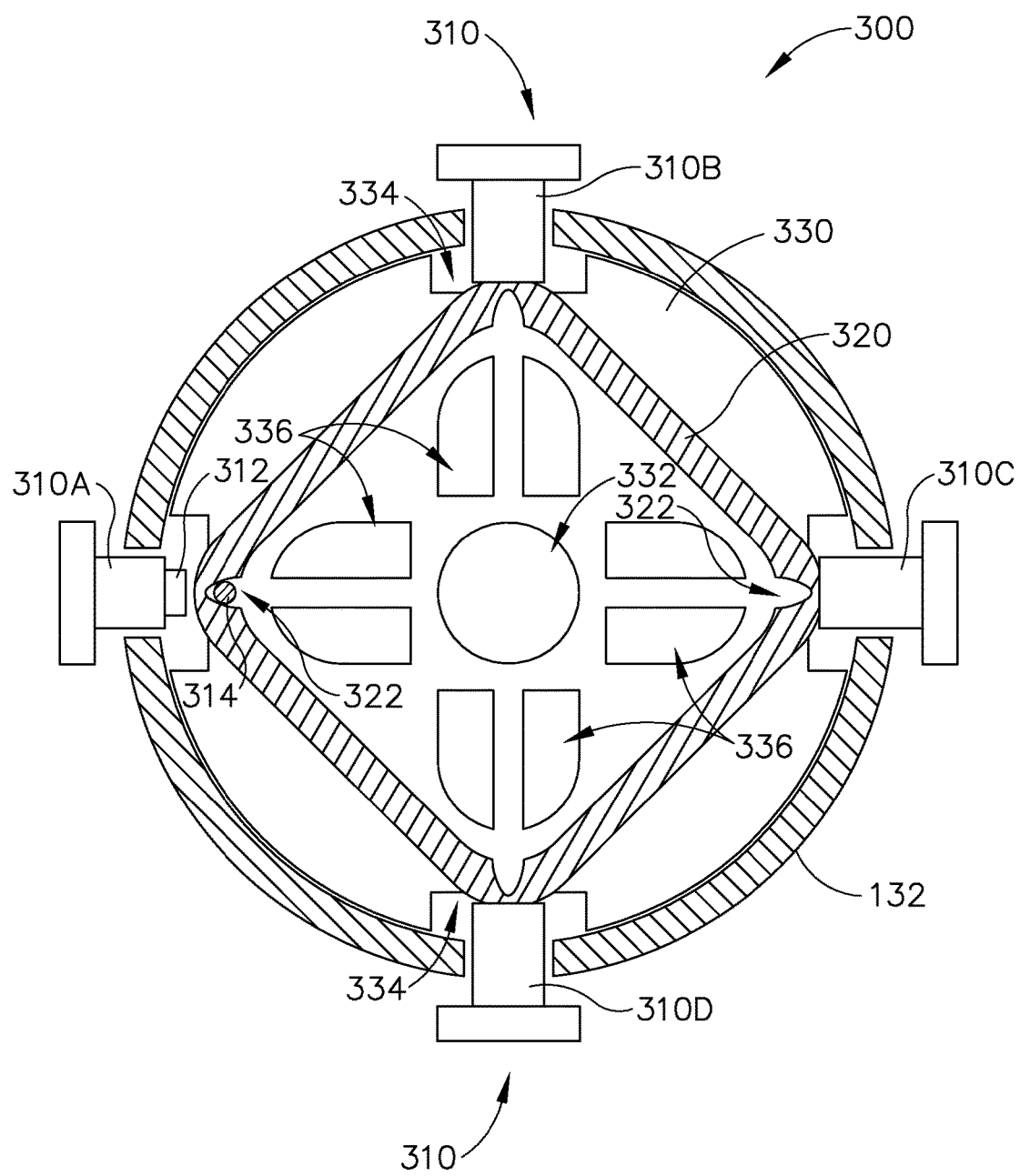
FIG. 18 depicts a front cross-sectional view of an alternative actuation assembly that may be incorporated into the instrument of FIG. 2.

1. Exemplary Alternative Actuation Assembly with Actuation Band and Elastomer Washer FIGS. 18-24B show one merely illustrative example of an alternative actuation assembly (300). Actuation assembly (300) of this example is configured to operate substantially similar to actuation assembly (200) discussed above except for the differences discussed below. Actuation assembly (300) may be readily incorporated into instrument (120) in place of actuation assembly (200). As best seen in FIG. 18, actuation assembly (300) comprises a plurality of buttons (310), a square-shaped band (320) having rounded corners, and an elastomer washer (330). Buttons (310) comprise four buttons (310A, 310B, 310C, 310D) in this example, though it should be understood that any other suitable number of buttons may be provided. Each button (310) is slidably disposed within body (132) of instrument (120) and is pivotably coupled thereto such that buttons (310) may be translated radially inwardly or outwardly relative to body (132). As shown in FIGS. 23A-23B, each button (310B, 310C, 310D) includes an integral pin (313) providing a pivotal coupling between button (310B, 310C, 310D) and body (132). While button (310A) is not shown in FIGS. 23A-23B, it should be understood that button (310A) may have the same kind of integral pin (313) and associated pivotal relationship with body (132).

A main button (310A) of buttons (310) includes an integral contact switch (312) positioned within an interior of button (310A) and extending inwardly from an inner surface of main button (310A). Of course, those of ordinary skill in the art will immediately recognize that contact switch (312) may be positioned at various other suitable locations. Furthermore, contact switch (312) may be substituted or supplemented with various other kinds of switches or actuation members, etc. As will be discussed in more detail below, radially inward movement of each button (310) causes transverse movement of band (320) and/or actuates contact switch (312) to thereby provide an electrical signal to generator (12) and/or to close a circuit between generator (12) and transducer (126).

As shown in FIGS. 23A-24B, buttons (310B, 310C, 310D) each comprise a slot (311) formed in an inner surface of buttons (310B, 310C, 310D). A corner of band (320) is disposed within each of these slots (311) such that band (320) is held in place (i.e., restrained along an axial dimension and a radial dimension) by contact between band (320) and buttons (310B, 310C, 310D). In addition, due to the contact between band (320) and buttons (310B, 310C, 310D), radially inward translation of each button (310B, 310C, 310D) will be communicated to band (320) as described below. Band (320) further comprises a plurality of slots (322) formed in an interior surface of each corner of band (320). Slots (322) are configured to enable band (320) to flex at the corners of band (320), as will be described in greater detail below.

Main button (310A) comprises a pin (314) that is slidably disposed within a particular slot (322). In an initial position, pin (314) engages interior surfaces of slot (322) to thereby align band (320) to thereby hold band (320) in place through contact between pin (314) and slot (322). Thus, it should be appreciated that in an initial position, band (322) maintains four points of contact with buttons (310) as shown in FIG. 18.

Figure 19:
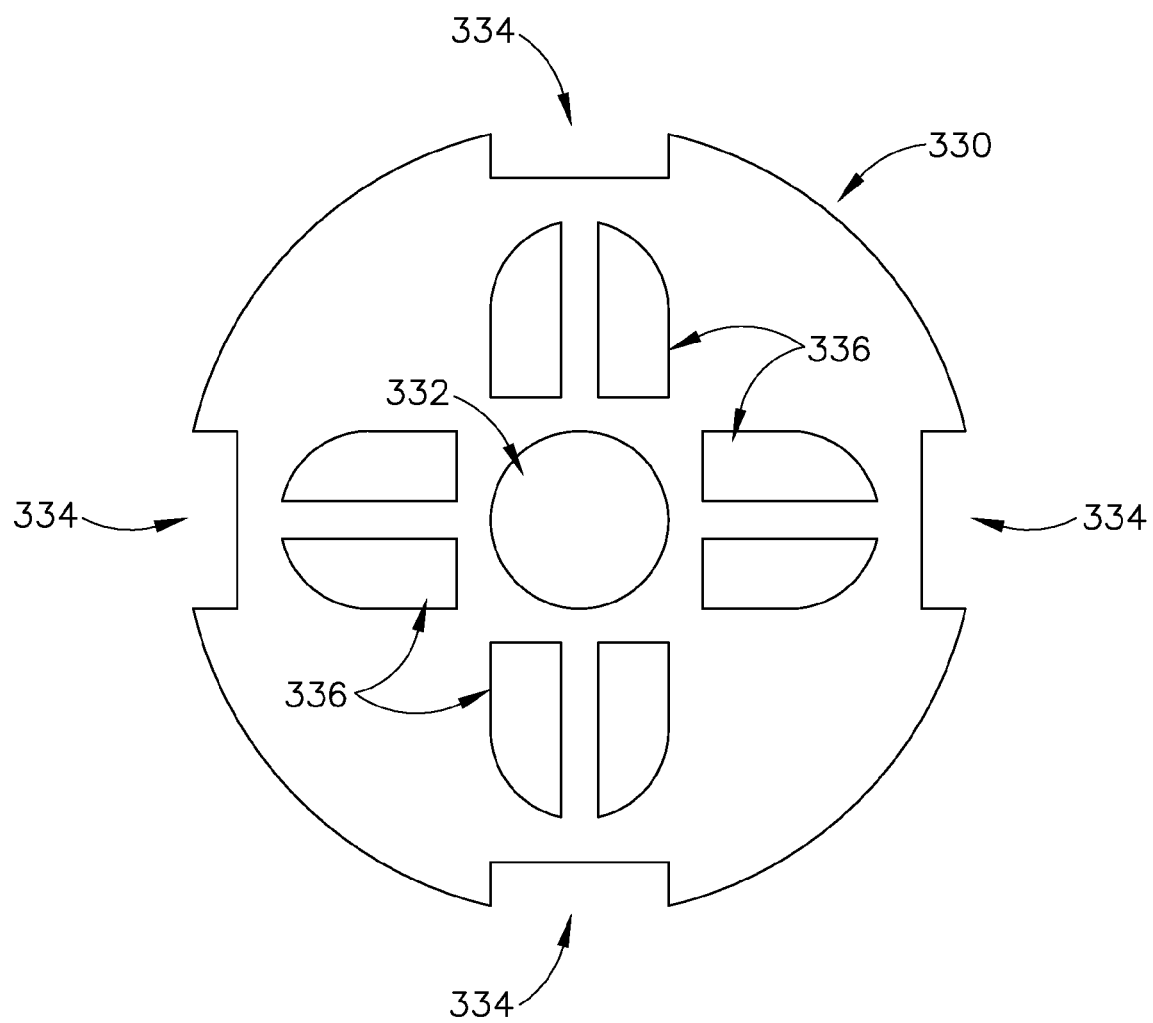
FIG. 19 depicts a front view of a resilient washer of the actuation assembly of FIG. 18.

As shown in FIG. 19, elastomer washer (330) defines a circular opening (332) that is sized to accommodate waveguide (148) without contacting waveguide (148). Elastomer washer (330) also defines a plurality of rectangular recesses (334) and a plurality of openings (336). Of course, recesses (334) and openings (336) are merely optional and may be substituted, supplemented, or omitted as desired. Openings (336) are configured to increase the flexibility of elastomer washer (330). In some versions, openings (336) promote buckling of elastomer washer (330) when elastomer washer (330) is compressed. As shown in FIGS. 23A-24B, each button (310B, 310C, 310D) of buttons (310) comprises a slot (316) formed in a bottom surface of buttons (310). A flat surface of each rectangular recess (334) of elastomer washer (330) is disposed within each of these slots (316) such that elastomer washer (330) is configured to resiliently bias buttons (310) outwardly into the positions shown in FIG. 18. While button (310A) is not shown in FIGS. 23A-24B, it should be understood that button (310A) may have the same kind of slot (316) and associated relationship with elastomer washer (330). While elastomer washer (330) resiliently biases each button (310) radially outwardly, elastomer washer (330) nevertheless deforms to accommodate inward deflection of buttons (310) when an operator depresses buttons (310), as shown in FIGS. 20-22, 23B, and 24B.

Figure 20:
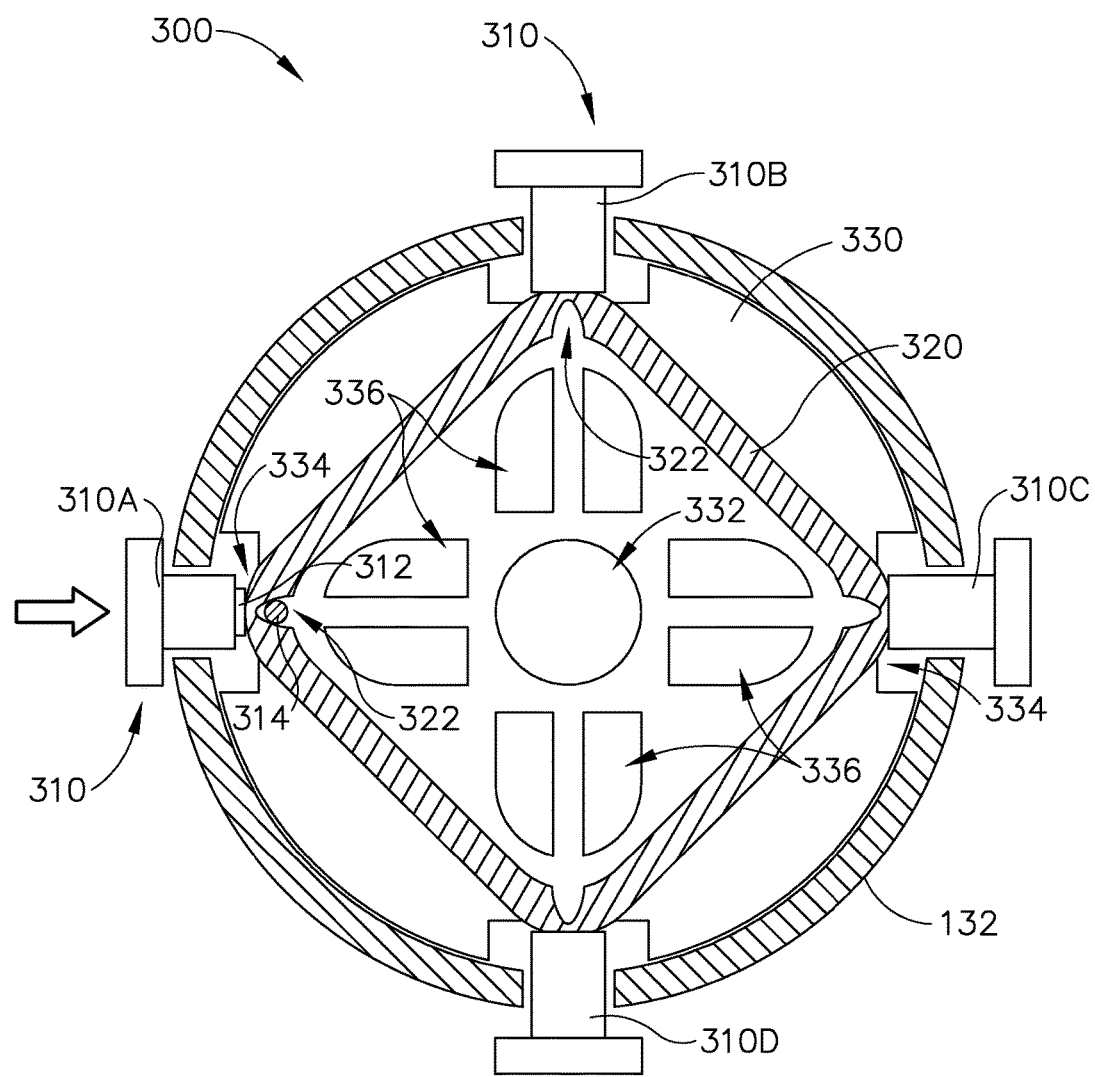
FIG. 20 depicts a front cross-sectional view of the actuation assembly of FIG. 18, with a first button depressed to thereby actuate the instrument of FIG. 2.
Figure 23A:
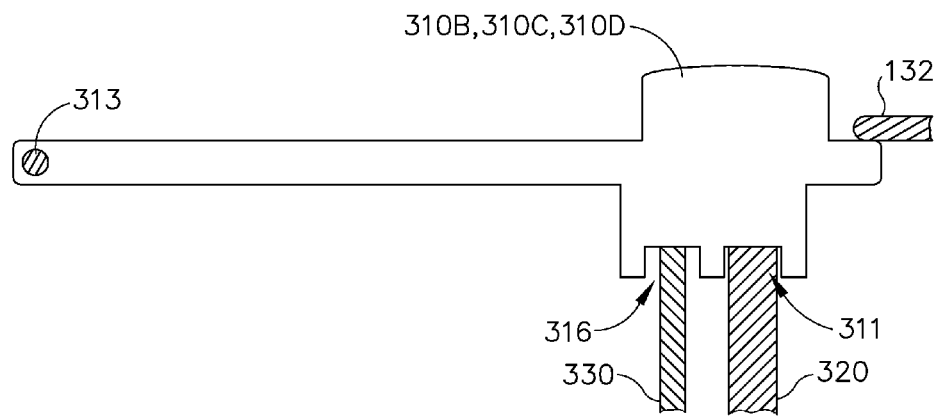
FIG. 23A depicts a side cross-sectional view of a button of the actuation assembly of FIG. 18, with the button in a first pivotal position.
Figure 23B:
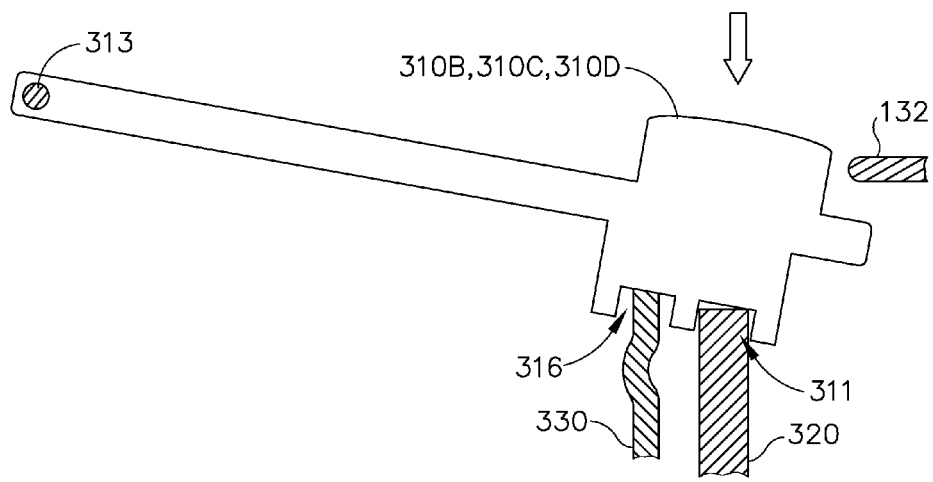
FIG. 23B depicts a side cross-sectional view of the button of FIG. 23A, with the button moved into a second pivotal position.
Figure 24A:
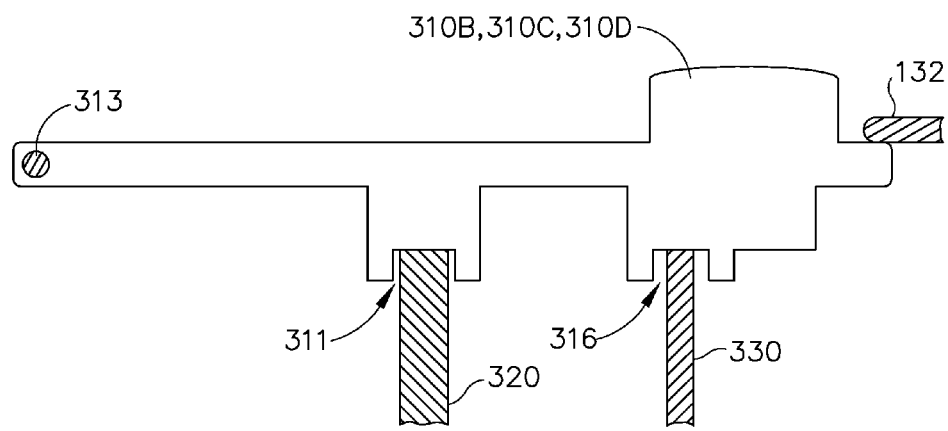
FIG. 24A depicts a side cross-sectional view of an exemplary alternative button of the actuation assembly of FIG. 18, with the button in a first pivotal position.
Figure 24B:
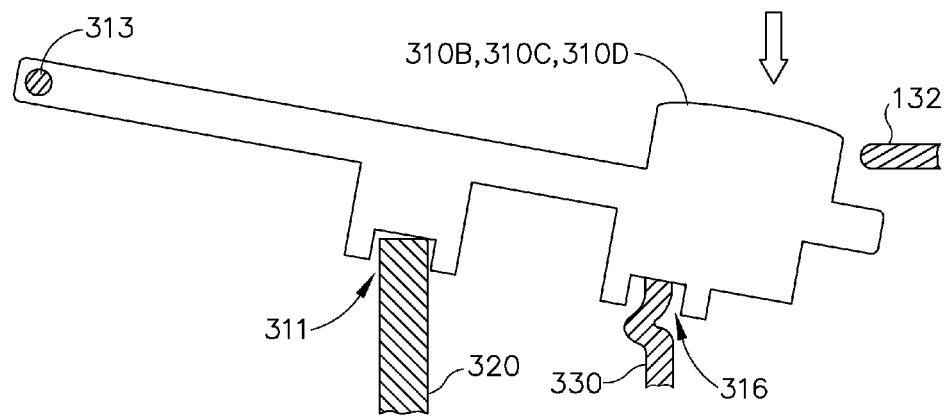
FIG. 24B depicts a side cross-sectional view of the button of FIG. 24A, with the button moved into a second pivotal position.

As shown in FIG. 20, when an operator depresses main button (310A), band (320) provides a mechanical ground against contact switch (312). Buttons (310B, 310C, 310D) prevent band (320) from flexing or otherwise moving along a radial/transverse plane. Contact switch (312) thus engages a corner of band (320) so as to actuate contact switch (312) to thereby provide an electrical signal to generator (12) and/or to close a circuit between generator (12) and transducer (126). As main button (310A) is depressed, main button (310A) also compresses elastomer washer (330) via slot (316) as shown in FIGS. 23B and 24B. As the operator releases main button (310A), elastomer washer (330) drives main button (310A) back to the position shown in FIG. 18.

Figure 21:
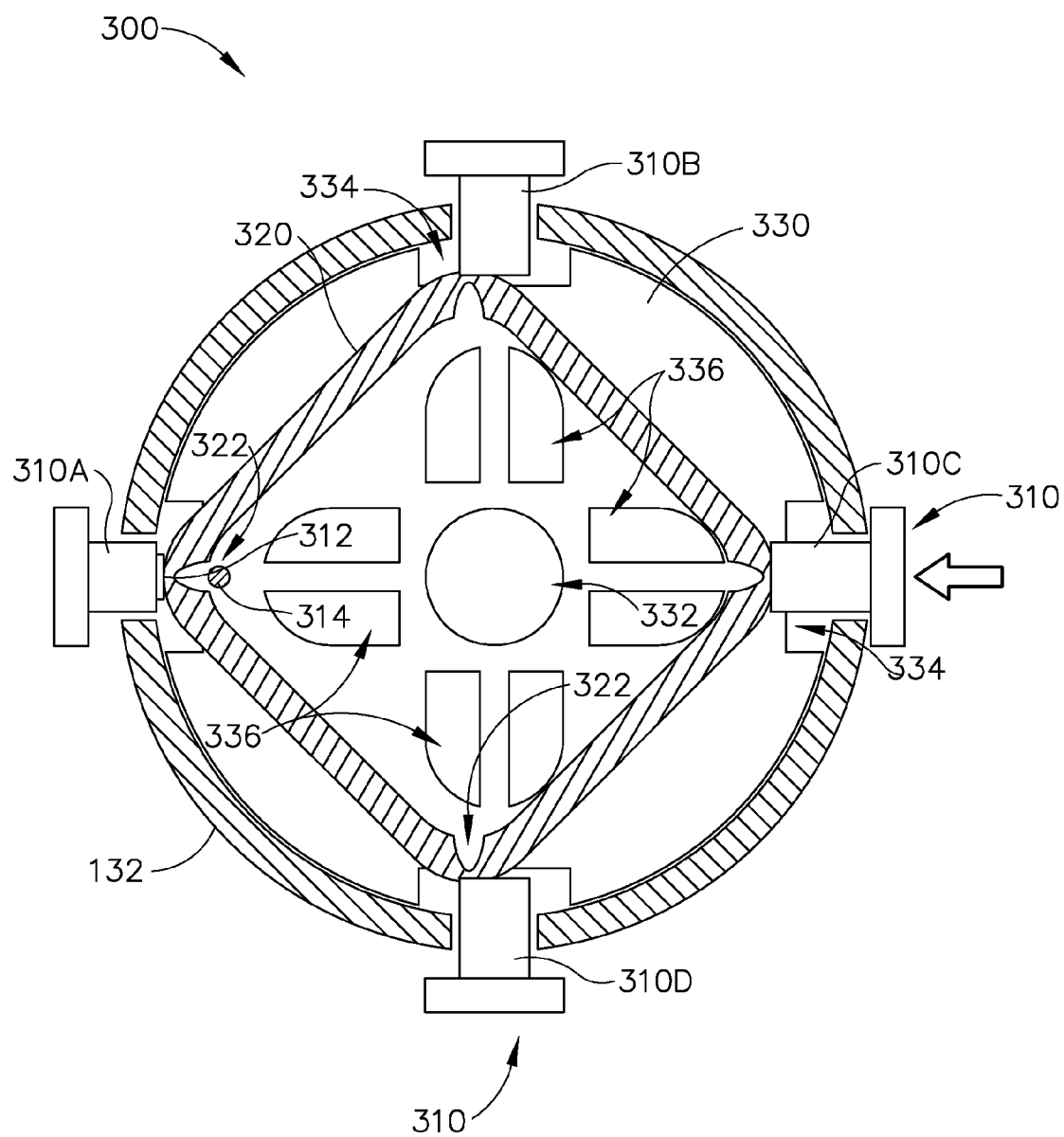
FIG. 21 depicts a front cross-sectional view of the actuation assembly of FIG. 18, with a second button depressed to thereby actuate the instrument of FIG. 2.

As shown in FIG. 21, as button (310C) (opposite of main button (310A)) is depressed, contact between band (320) and button (310C) within slot (311) drives band (320) transversely into contact with contact switch (312) so as to actuate contact switch (312) to thereby provide an electrical signal to generator (12) and/or to close a circuit between generator (12) and transducer (126). Buttons (310B, 310D) allow band (320) to slide along the transverse/radial plane to communicate the transverse motion of button (310C) to contact switch (312). As button (310C) is depressed, button (310B) compresses elastomer washer (330) via slot (316) as shown in FIGS. 23B and 24B. As the operator releases button (310C), elastomer washer (330) drives button (310C) back to the position shown in FIG. 18.

Figure 22:
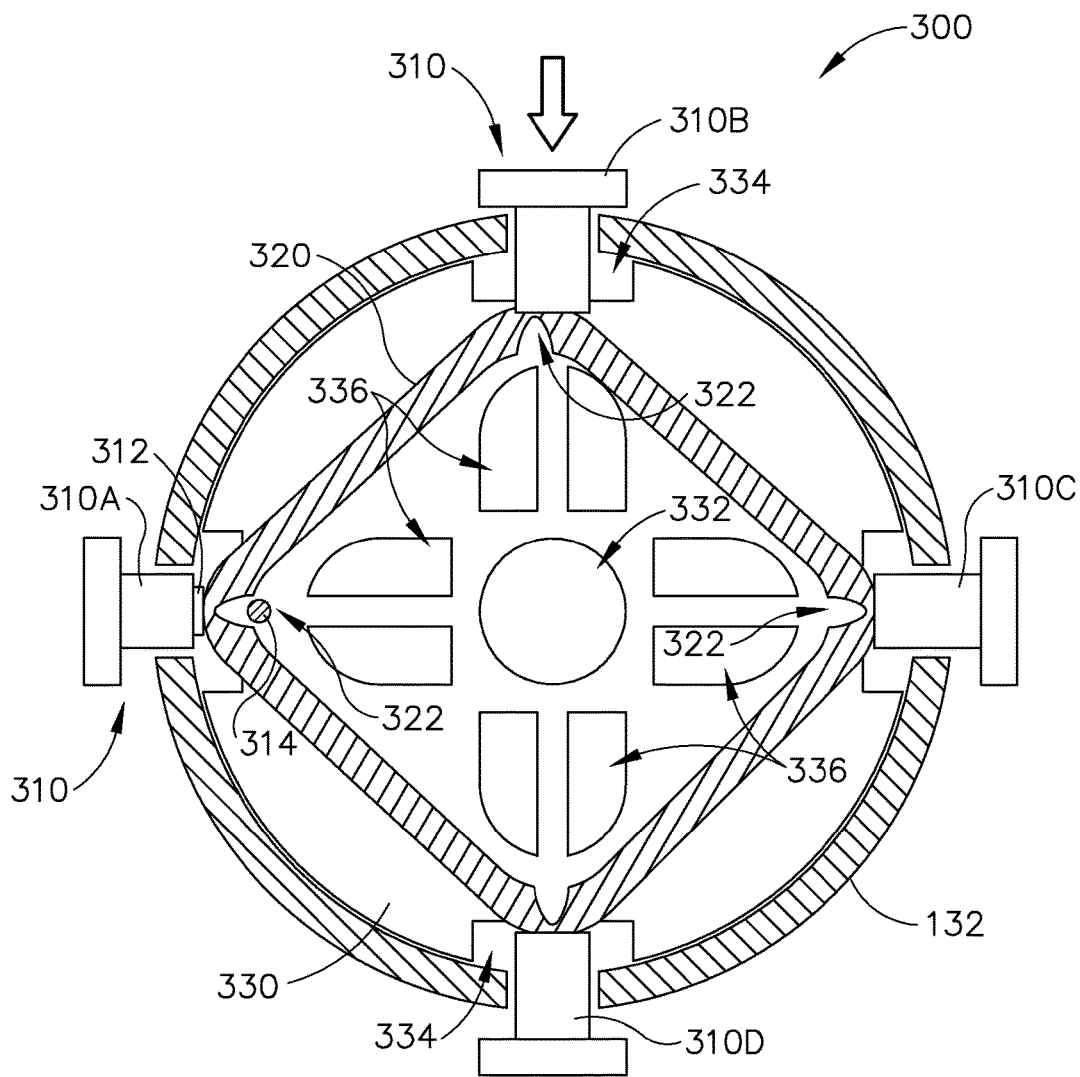
FIG. 22 depicts a front cross-sectional view of the actuation assembly of FIG. 18, with a third button depressed to thereby actuate the instrument of FIG. 2.

As shown in FIG. 22, as button (310B) (adjacent to main button (310A)) is depressed, contact between band (320) and button (310B) within slot (311) urges band (320) transversely toward the other button (310D) adjacent to main button (310A), thereby translating band (320). As band (320) translates, since band (320) grounds out against buttons (310C, 310D), band (320) flexes outwardly into contact with contact switch (312) so as to actuate contact switch (312) to thereby provide an electrical signal to generator (12) and/or to close a circuit between generator (12) and transducer (126). As button (310B) is depressed, button (310B) compresses elastomer washer (330) via slot (316) as shown in FIGS. 23B and 24B. As the operator releases button (310B), elastomer washer (330) drives button (310B) back to the position shown in FIG. 18. It should be understood that a similar sequence will occur when the operator depresses button (310D). In particular, when the operator depresses button (310D), band (320) will translate and flex in substantially the same manner as when the operator depresses button (310B).

As shown in FIGS. 23A-24B, a position of band (320) can be changed so as to manipulate the ability and ease by which buttons (310) can be depressed. In particular, in the example shown in FIGS. 24A-24B, the location of band (320) is closer to pins (313) than the location of band (320) in the example shown in FIGS. 23A-24B. Locating band (320) closer to pins (313) may provide greater resistance to actuation of buttons (310). Other suitable ways in which the operability of buttons (310) may be manipulated will be apparent to those of ordinary skill in the art in view of the teachings herein.

2. Exemplary Alternative Actuation Assembly with Actuation Band and Plate

Figure 25:
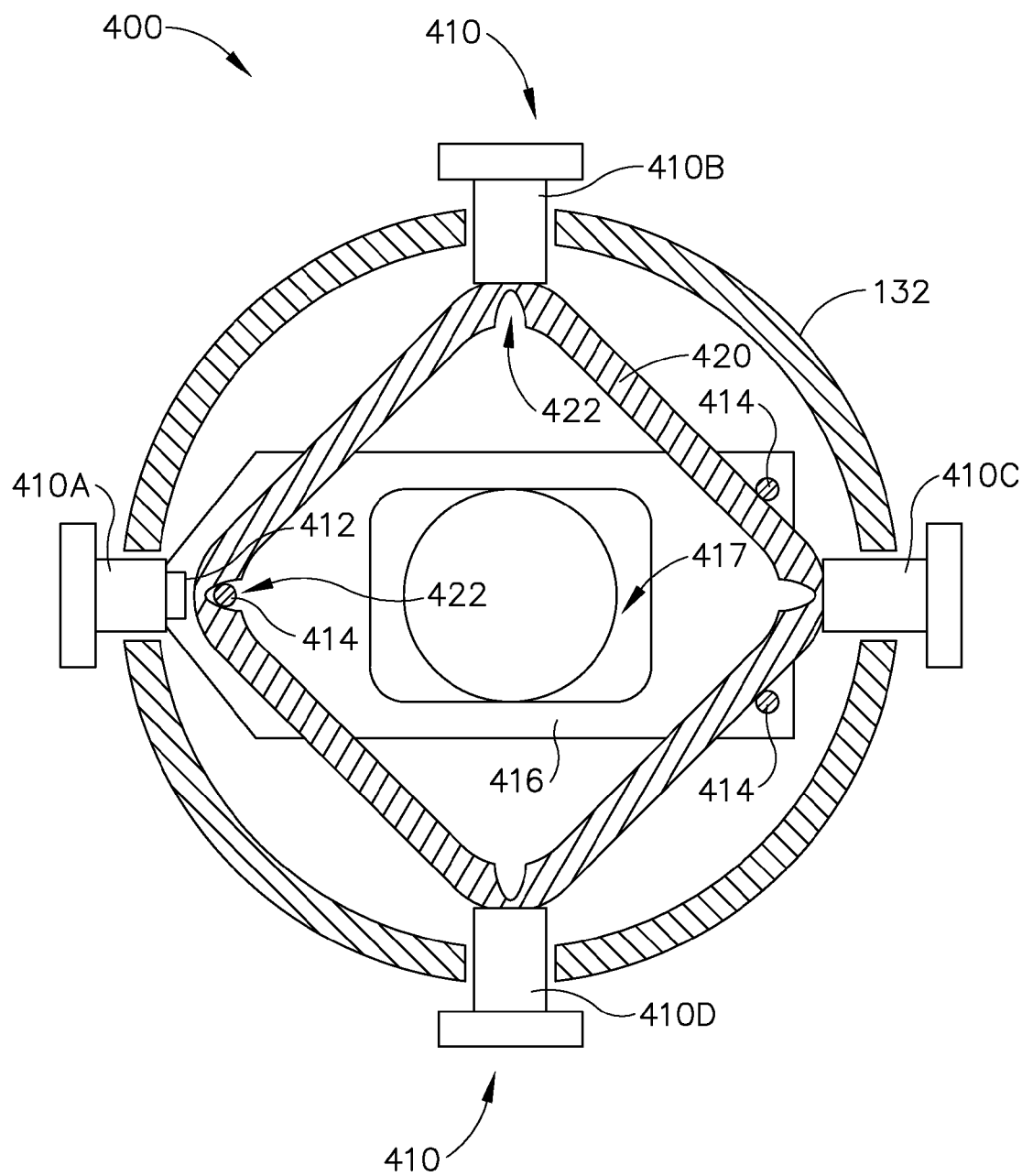
FIG. 25 depicts a front cross-sectional view of another exemplary alternative actuation assembly that may be incorporated into the instrument of FIG. 2.
Figure 27:
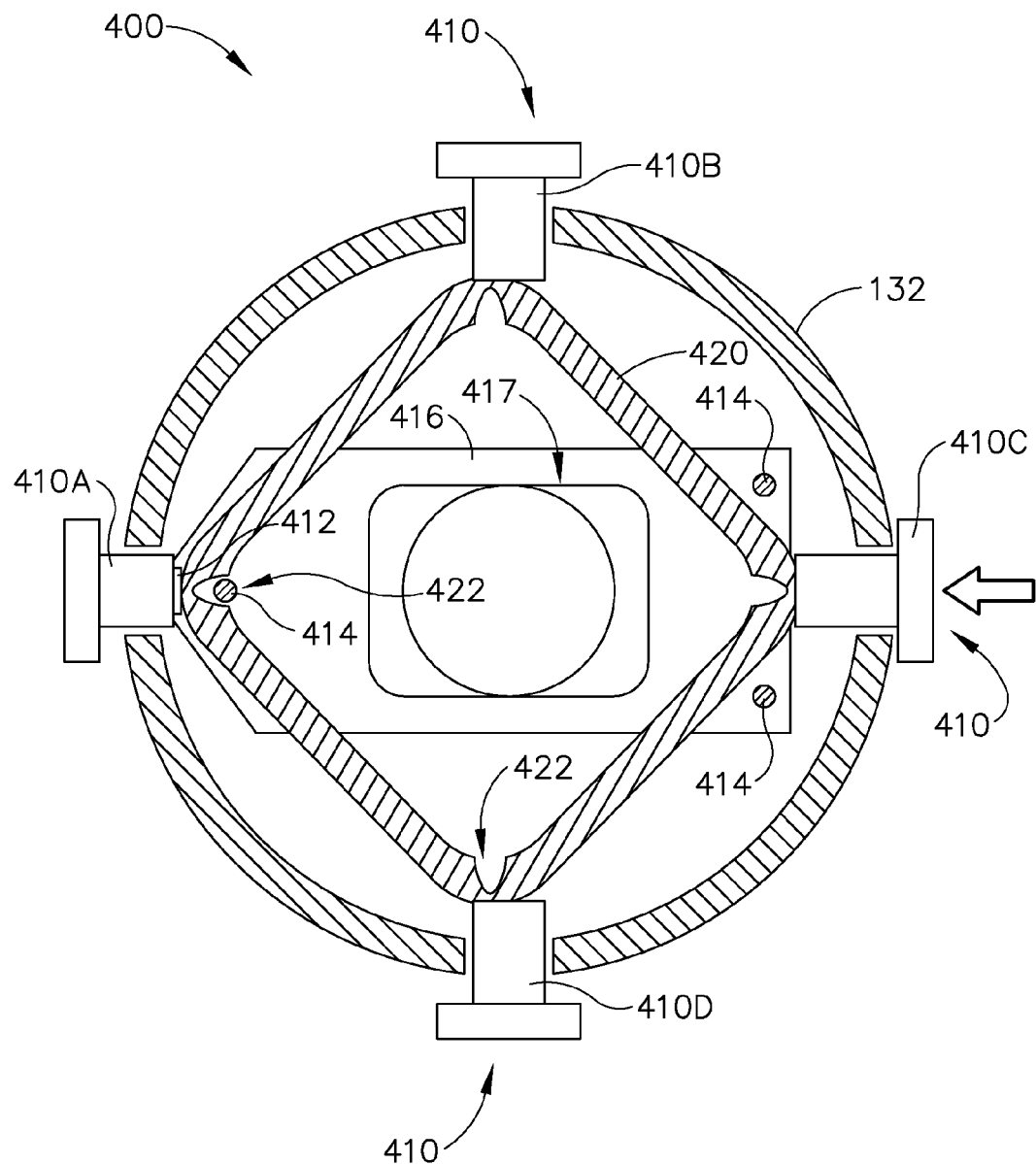
FIG. 27 depicts a front cross-sectional view of the actuation assembly of FIG. 25, with a second button depressed to thereby actuate the instrument of FIG. 2.
Figure 28:
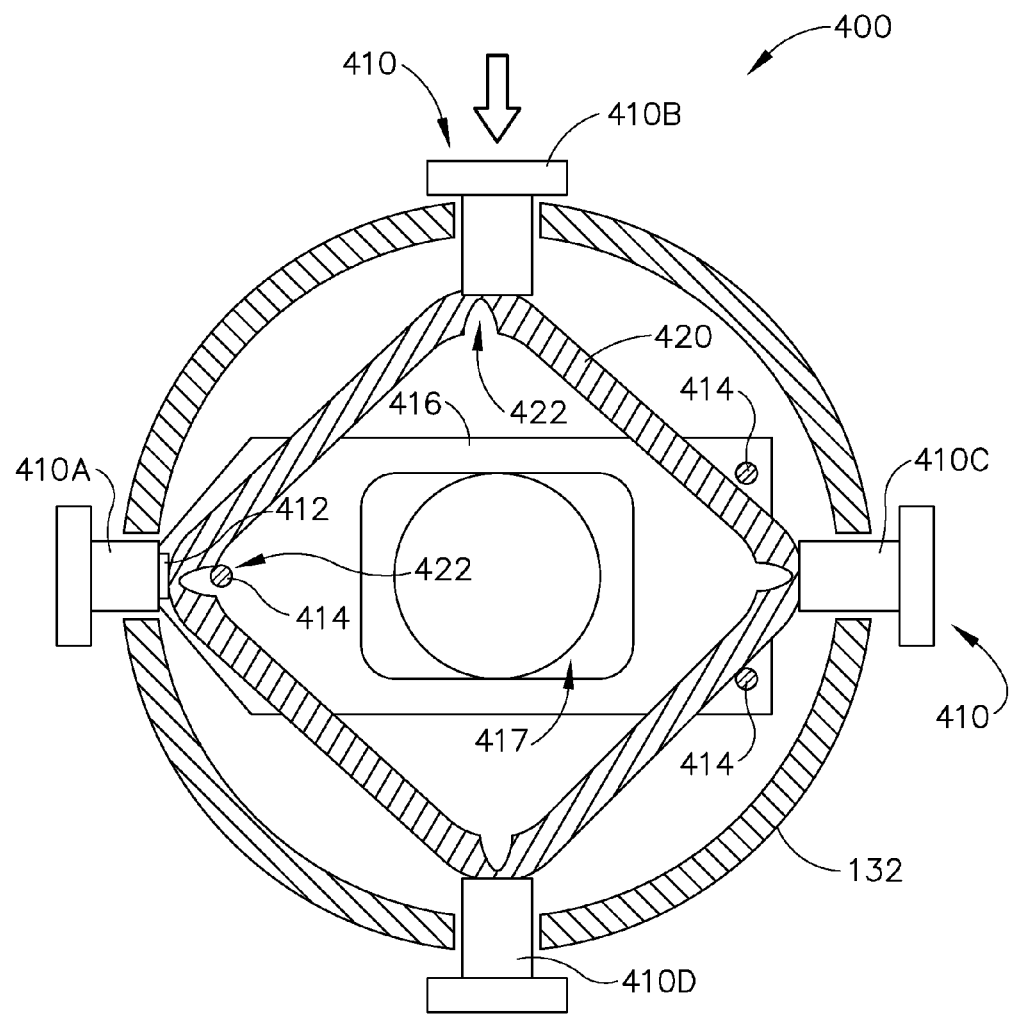
FIG. 28 depicts a front cross-sectional view of the actuation assembly of FIG. 25, with a third button depressed to thereby actuate the instrument of FIG. 2.
Figure 29A:
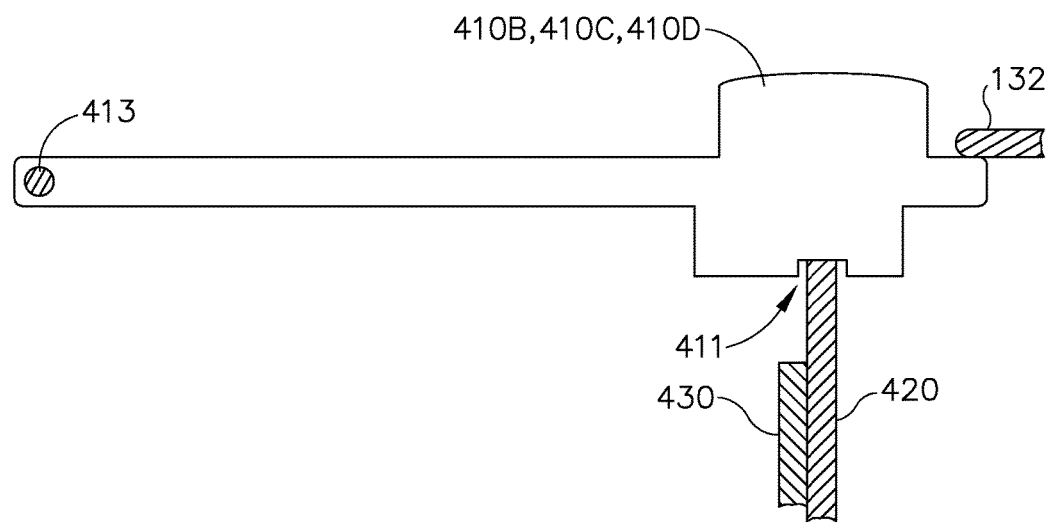
FIG. 29A depicts a side cross-sectional view of a button of the actuation assembly of FIG. 25, with the button in a first pivotal position.
Figure 29B:
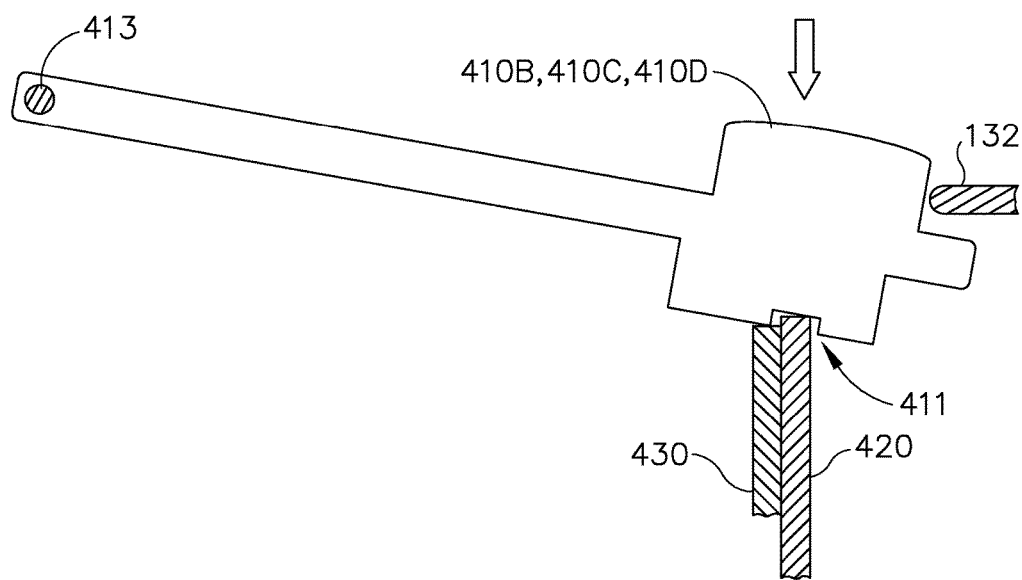
FIG. 29B depicts a side cross-sectional view of the button of FIG. 29A, with the button moved into a second pivotal position.

FIGS. 25-29B show another exemplary alternative actuation assembly (400). Actuation assembly (400) of this example is configured to operate substantially similar to actuation assembly (300) discussed above except for the differences discussed below. It should be understood that actuation assembly (400) may be readily incorporated into instrument (120) in place of actuation assembly (200). As best seen in FIG. 25, actuation assembly (400) comprises a plurality of buttons (410) and a square-shaped band (420) having rounded corners. Buttons (410) comprise four buttons (410A, 410B, 410C, 410D) in this example, though it should be understood that any other suitable number of buttons may be provided. Each button (410) is slidably disposed within body (132) of instrument (120) and pivotably coupled thereto such that buttons (410) may be translated radially inwardly or outwardly relative to body (132). As shown in FIGS. 293A-29B, each button (410B, 410C, 410D) includes an integral pin (413) providing a pivotal coupling between button (410B, 410C, 410D) and body (132). While button (3410A) is not shown in FIGS. 29A-29B, it should be understood that button (410A) may have the same kind of integral pin (413) and associated pivotal relationship with body (132).

A main button (410A) of buttons (410) includes an integral contact switch (412) positioned within an interior of button (410A) and extending inwardly from an inner surface of main button (410A). As will be discussed in more detail below, radially inward movement of each button (410) causes transverse movement of band (420) and/or actuates contact switch (412) to thereby provide an electrical signal to generator (12) and/or to close a circuit between generator (12) and transducer (126).

As shown in FIGS. 29A-29B, buttons (410B, 410C, 410D) each comprise a slot (411) formed in an inner surface of buttons (410B, 410C, 410D). A corner of band (420) is disposed within each of these slots (411) such that band (420) is held in place (i.e., restrained along an axial dimension and a radial dimension) by contact between band (420) and buttons (410B, 410C, 410D). In addition, due to the contact between band (420) and buttons (410B, 410C, 410D), radially inward translation of each button (310B, 310C, 310D) will be communicated to band (420) as described below. Band (420) further comprises a plurality of slots (422) formed in an interior surface of each corner of band (420). Slots (422) are configured to enable band (420) to flex at the corners of band (420), as will be described in greater detail below.

Main button (410A) is coupled with an elongate plate (416). Elongate plate (416) comprises a rectangular opening (417) that is sized to accommodate waveguide (148) without contacting waveguide (148). Elongate plate (416) further comprises a plurality of pins (414), a first of which is slidably disposed within a particular slot (422) and two others of which engage an opposite portion of band (420). In an initial position, as shown in FIG. 25, pins (414) engage interior surfaces of slot (422) and the opposite portion of band (420) so as to align band (420) and so as to hold band (422) in place by contact between pin (414) and slot (422). Thus, it should be appreciated that in an initial position, band (422) maintains six points of contact with buttons (410).

Figure 26:
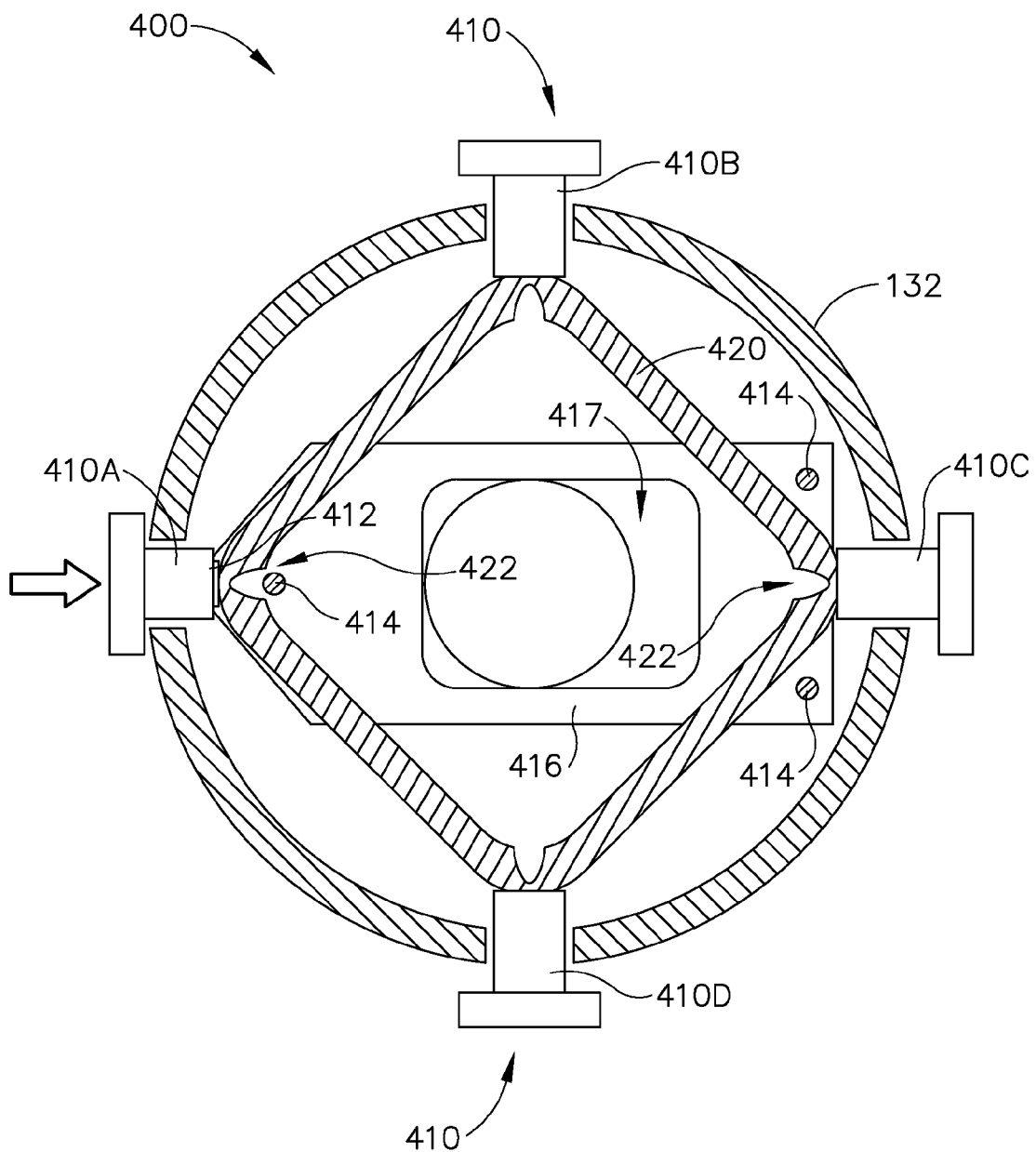
FIG. 26 depicts a front cross-sectional view of the actuation assembly of FIG. 25, with a first button depressed to thereby actuate the instrument of FIG. 2.

As shown in FIG. 26, when an operator depresses main button (410A), band (420) provides a mechanical ground against contact switch (412). Buttons (410B, 410C, 410D) prevent band (420) from flexing or otherwise moving along a radial/transverse plane. Contact switch (412) thus engages a corner of band (420) so as to actuate contact switch (412) to thereby provide an electrical signal to generator (12) and/or to close a circuit between generator (12) and transducer (126). In the present example, main button (410A) is resiliently biased to return to the position shown in FIG. 25 when the operator releases main button (410A). Contact switch (412) thus disengages band (420) when the operator releases main button (410A). Various suitable ways in which main button (410A) may be resiliently biased to return to the position shown in FIG. 25 will be apparent to those of ordinary skill in the art in view of the teachings herein.

As shown in FIG. 27, as button (410C) (opposite of main button (410A)) is depressed, contact between band (420) and button (410C) within slot (411) drives band (420) transversely into contact with contact switch (412) so as to actuate contact switch (412) to thereby provide an electrical signal to generator (12) and/or to close a circuit between generator (12) and transducer (126). Buttons (410B, 410D) allow band (320) to slide along the transverse/radial plane to communicate the transverse motion of button (410C) to contact switch (412). In the present example, button (410C) is resiliently biased to return to the position shown in FIG. 25 when the operator releases button (410C). Contact switch (412) thus disengages band (420) when the operator releases button (410C). Various suitable ways in which button (410C) may be resiliently biased to return to the position shown in FIG. 25 will be apparent to those of ordinary skill in the art in view of the teachings herein.

As shown in FIG. 28, as button (410B) (adjacent to main button (410A)) is depressed, contact between band (420) and button (410B) within slot (411) drives band (420) transversely toward the other button (410D) adjacent to main button (410A), thereby causing band (420) to flex. As band (420) is translated, since band (420) grounds out against buttons (410C, 410D) and the outer pins (414), band (420) flexes outwardly into contact with contact switch (412) so as to actuate contact switch (412) to thereby provide an electrical signal to generator (12) and/or to close a circuit between generator (12) and transducer (126). As with buttons (410A, 410C) described above, button (410B) may be resiliently biased to return to the position shown in FIG. 25 when the operator releases button (410B). It should be understood that a similar sequence will occur when the operator depresses button (410D). In particular, when the operator depresses button (410D), band (420) will flex in substantially the same manner as when the operator depresses button (410B).

As shown in FIGS. 29A-29B, a fixed stop (430) may be positioned to restrict inward radial movement of buttons (410). In addition, body (132) may be configured to restrict outward radial movement of buttons (410). Thus the angular range through which buttons (410) may pivot is dictated by the positioning and configuration of stop (430) and body (132). It should also be understood that the same structures and principles may apply to buttons (310) described above. Although not depicted, some versions actuation assembly (400) may incorporate elastomer washer (330), like actuation assembly (300), to resiliently bias buttons (410) toward the positions shown in FIG. 25.

3. Exemplary Alternative Actuation Assembly with Actuation Band and Large Plurality of Buttons FIG. 30 shows another exemplary alternative actuation assembly (500). Actuation assembly (500) of this example is configured to operate substantially similar to actuation assembly (300) discussed above except for the differences discussed below. It should be understood that actuation assembly (50) may be readily incorporated into instrument (120) in place of actuation assembly (200). Actuation assembly (500) comprises a plurality of buttons (510) and an octagonal-shaped band (520). While eight buttons (510) are shown, it should be understood that any other suitable number of buttons may be provided. Each button (510) is slidably disposed within body (132) of instrument (120) and is pivotably coupled thereto such that buttons (510) may be translated radially inwardly or outwardly relative to body (132). A main button (510A), of buttons (510) includes a contact switch (512) positioned within an interior of button (510A) and extending inwardly from an inner surface of main button (510A).

As with actuation assemblies (300, 400) discussed above, radially inward movement of main button (510A) directly actuates contact switch (512) to thereby provide an electrical signal to generator (12) and/or to close a circuit between generator (12) and transducer (126). Also as with actuation assemblies (300, 400) discussed above, radially inward movement of the other buttons (510B) causes transverse movement of band (520) and/or flexing of band (520) such that band (520) actuates contact switch (512) to thereby provide an electrical signal to generator (12) and/or to close a circuit between generator (12) and transducer (126). Band (520) comprises a plurality of slots (522) formed in an interior surface of each corner of band (522). Slots (522) are configured to enable band (520) to flex at the corners of band (520). Main button (510A) comprises a pin (514), which is slidably disposed within a particular slot (522). In an initial position, pin (514) engages interior surfaces of slot (522) so as to align band (520) and so as to hold band (520) in place by contact between pin (514) and slot (522). It should therefore be appreciated that, in an initial position, band (522) maintains eight points of contact with buttons (510).

Figure 31:
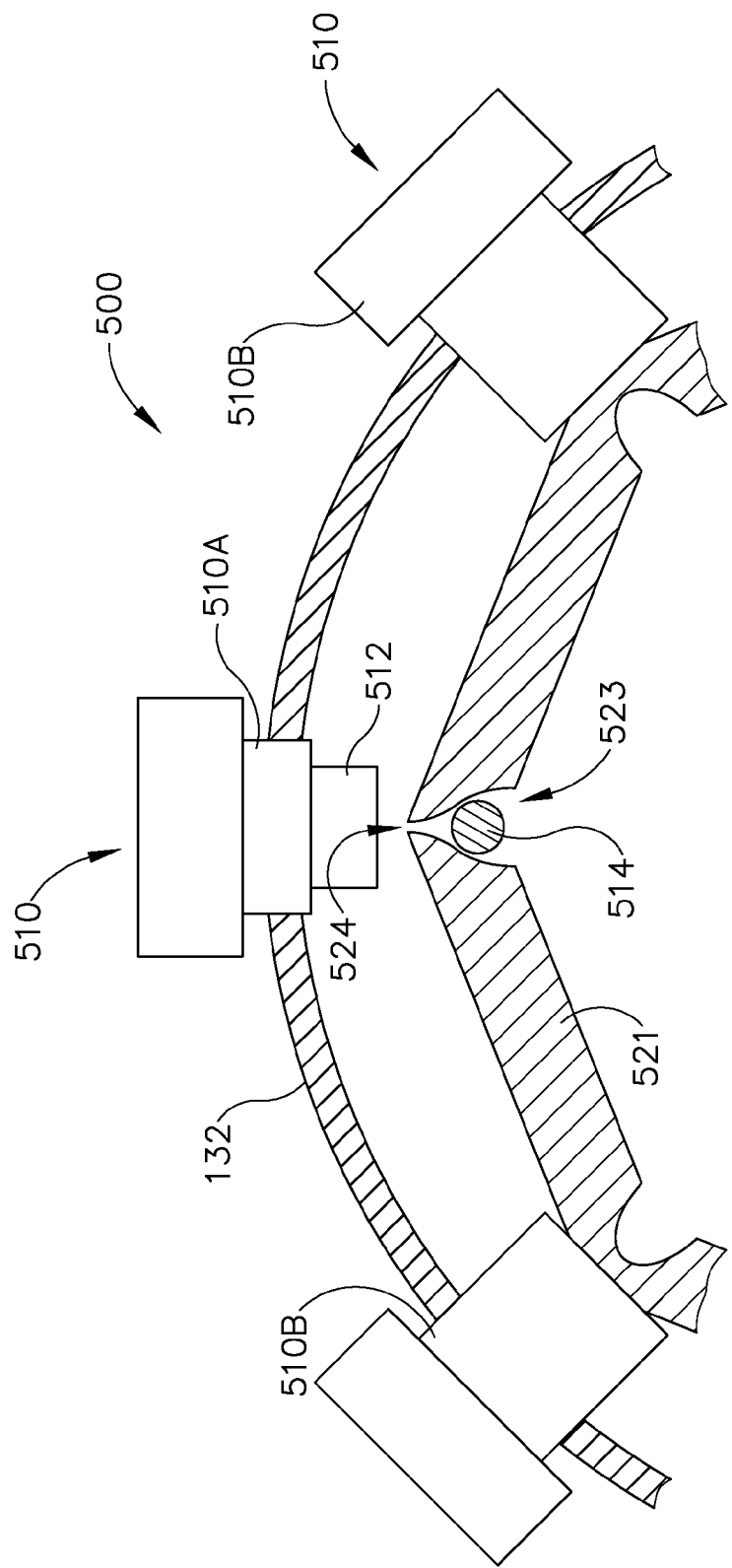
FIG. 31 depicts a detailed front cross-sectional view of yet another exemplary alternative actuation assembly that may be incorporated into the instrument of FIG. 2.

FIG. 31 shows an exemplary alternative band (521), which is an alternative version of band (520). Band (520) may be readily substituted with band (521). Band (521) of this present example comprises a break (524) formed between an exterior surface of band (521) and an interior surface of slot (523) at main button (510A) such that band (521) is effectively split at main button (510A). Slot (524) increases the flexibility of band (521) such that band (520) may be more easily compressed. Furthermore, band (521) may be resiliently biased such that band (521) clamps pin (514) within slot (522) to thereby improve alignment of band (521) within instrument (132).

Figure 32:
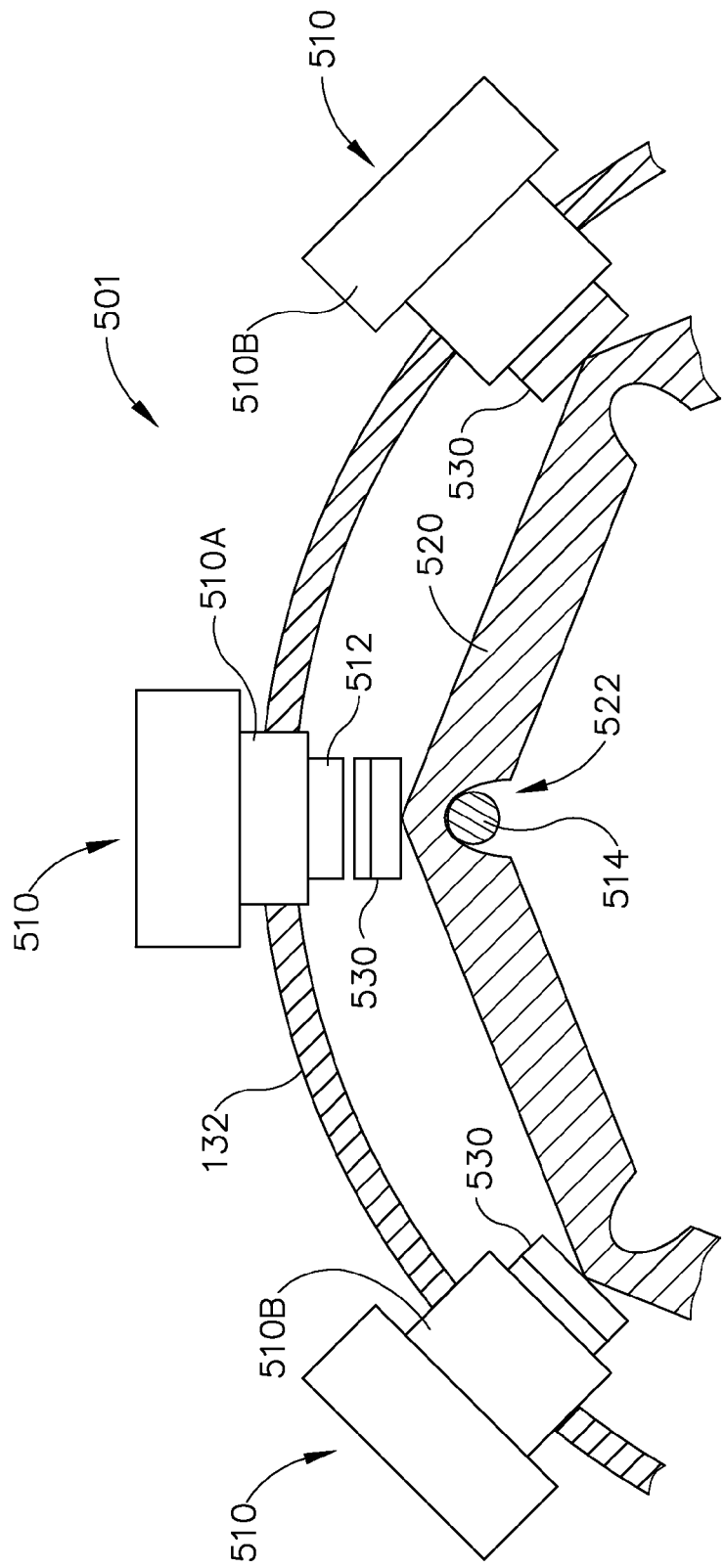
FIG. 32 depicts a detailed front cross-sectional view of yet another exemplary alternative actuation assembly that may be incorporated into the instrument of FIG. 2.

FIG. 32 shows an exemplary alternative version of actuation assembly (500). Actuation assembly (501) of this example comprises a plurality of elastomer members (530) disposed between band (520) and buttons (510). Elastomer members (530) each comprise two layers in this example, each layer of which may have unique elasticity characteristics. In some other versions, elastomer members (530) each have just a single layer or more than two layers. As with elastomer washer (330) discussed above, elastomer members (530) are configured to bias buttons (510) outwardly toward the positions shown in FIG. 32. Furthermore, elastomer members (530) may deaden any tactile feedback an operator may perceive from motion of buttons (510) so as to improve the operator experience using instrument (132). In addition or in the alternative, elastomer members (530) may take up slack or free motion that might otherwise occur with buttons (510), thereby preventing rattling or other "lost motion" effects in buttons (510).

While elastomer members (530) are shown as being positioned at each button (510), some variations may provide an elastomer member (530) only at main button (510A), without having elastomer members (530) at secondary buttons (510B). Thus, some versions of actuation assembly (500) may have just one elastomer member (530). Additionally or alternatively, and although not depicted, it should be understood that actuation assembly (501) may incorporate a variation of elastomer washer (330) discussed above to thereby bias buttons (510) into the positions shown in FIG. 30. Actuation assembly (501) may otherwise be configured and operable like actuation assembly (500).

Figure 33:
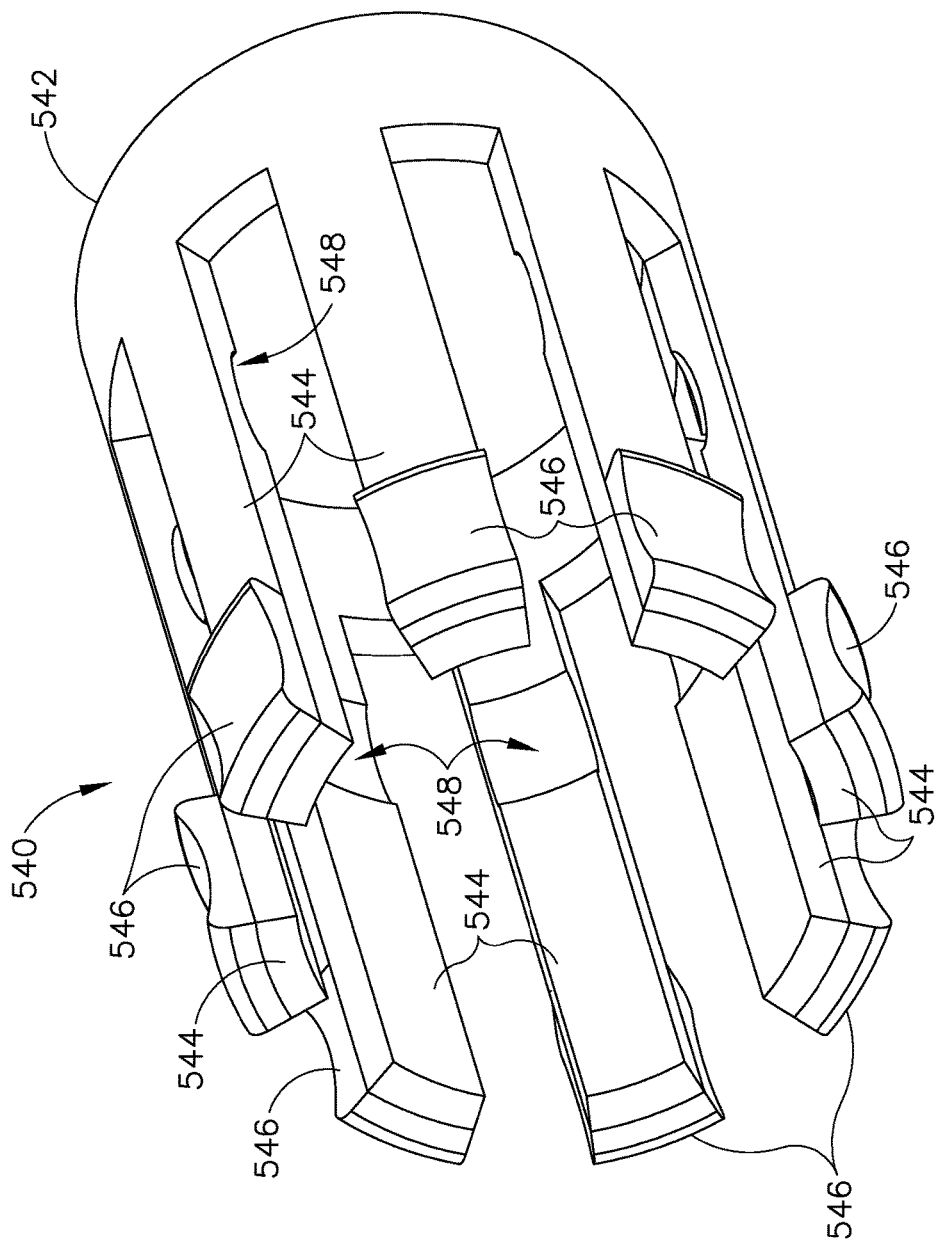
FIG. 33 depicts a perspective view of a button assembly that may be incorporated into the actuation assemblies of FIGS. 30, 31, and 32.
Figure 34:
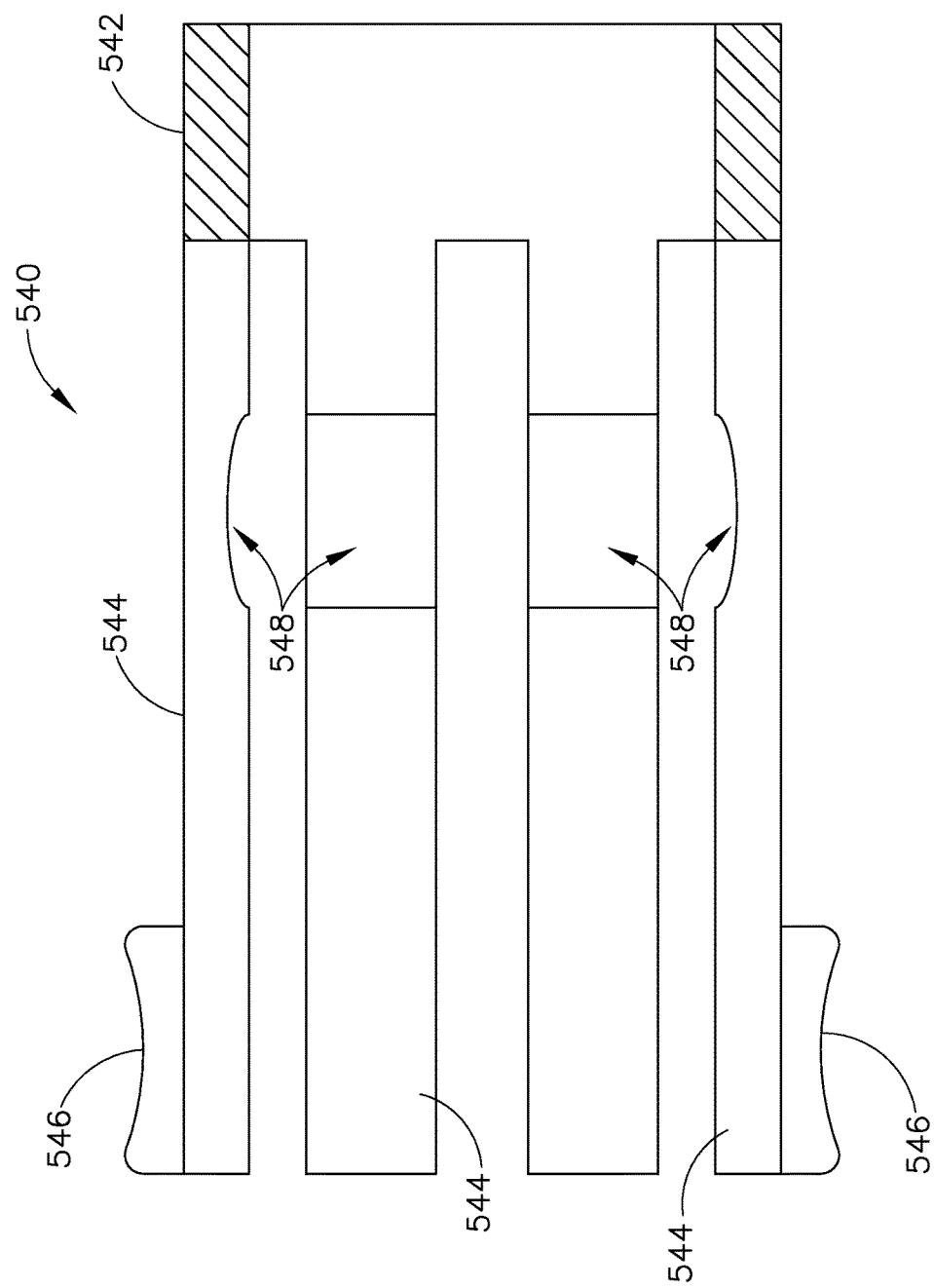
FIG. 34 depicts a side cross-sectional view of the button assembly of FIG. 33.

FIGS. 33-34 show a button assembly (540) operable for use with actuation assemblies (300, 400, 500) discussed above. In particular, although button assembly (540) is shown and described as having eight buttons, button assembly (540) may have any number of buttons as will be understood from the discussion below. Button assembly (540) comprises a cylindrical base (542) with a plurality of arms (544) extending distally therefrom and angularly separated by a plurality of longitudinal slots, providing button assembly (540) with a castellated configuration. A free end of each arm (544) provides a button (546). An arcuate recess (548) formed in a base portion of each arm (544) is configured to provide for flexibility, although it should be appreciated that arms (544) are biased to the positions shown in FIGS. 33-34. Thus, it should be appreciated that buttons (546) are configured to pivot radially inwardly and outwardly from an axial center of button assembly (540). In some alternative versions, buttons (not shown) are formed separately and are positioned outside of the end of each arm (544), such that arms (544) just provide a resilient bias to the separate buttons.

Figure 35:
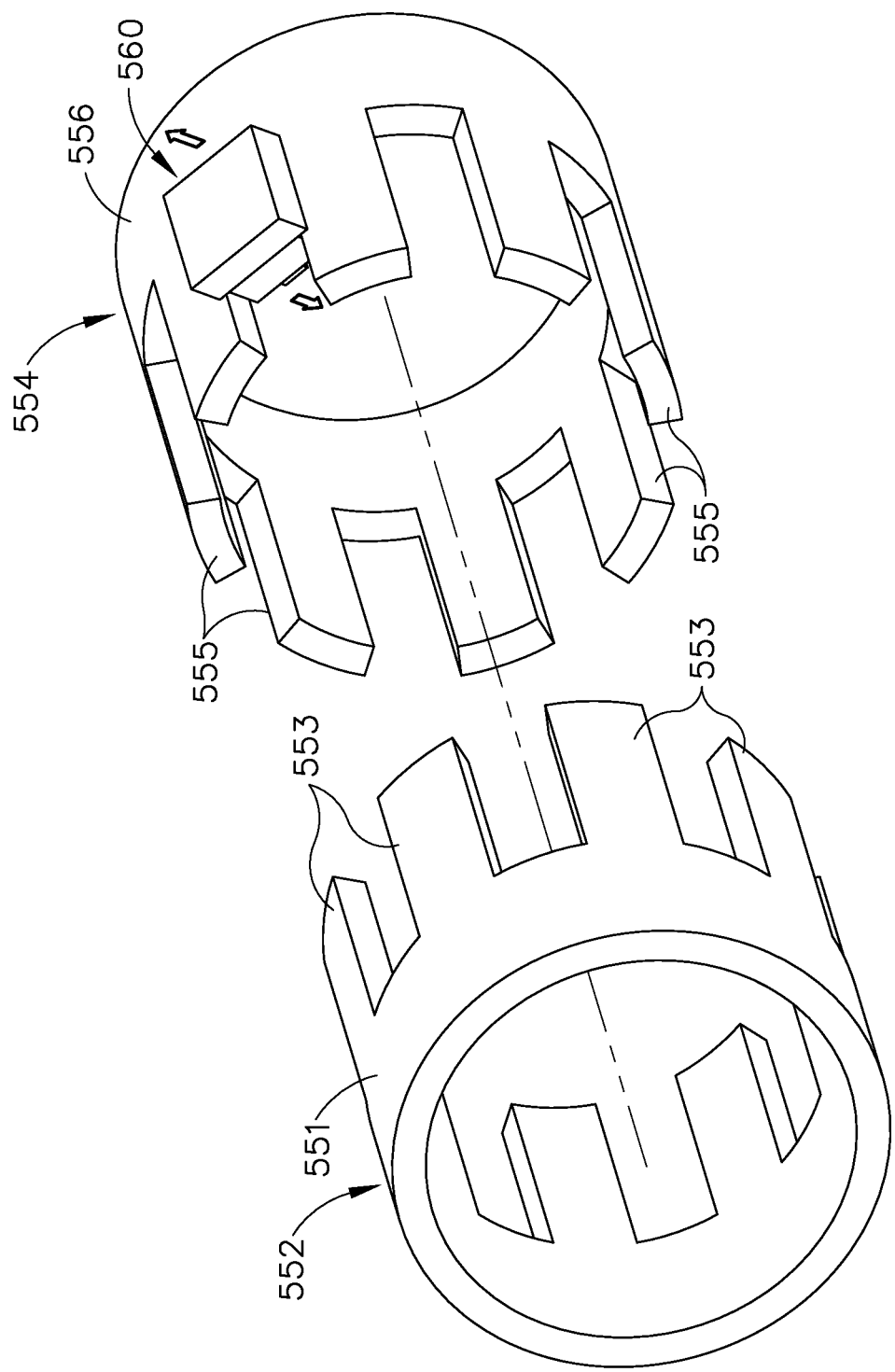
FIG. 35 depicts a partially exploded perspective view of an exemplary alternative trigger assembly that may be incorporated into the actuation assemblies of FIGS. 30, 31, and 32.
Figure 36:
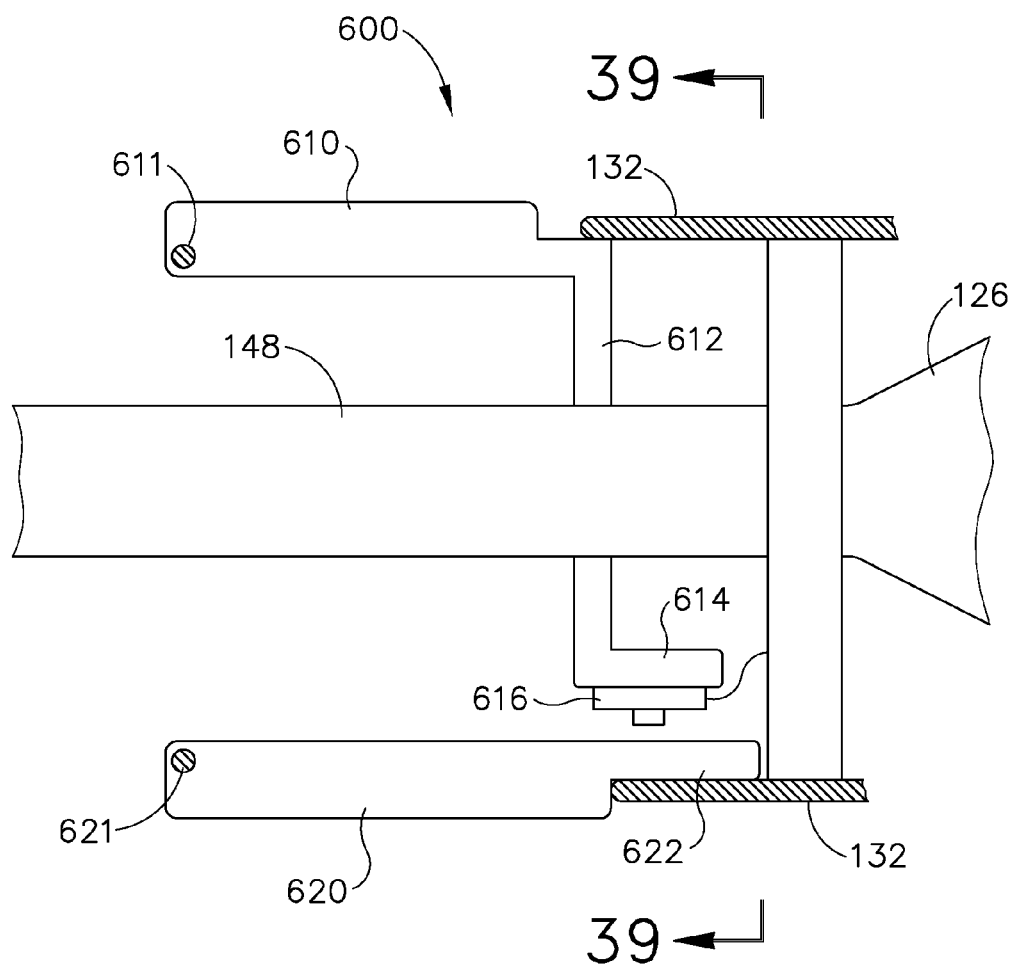
FIG. 36 depicts a side cross-sectional view of yet another exemplary alternative actuation assembly that may be incorporated into the instrument of FIG. 2, with a first trigger in a first pivotal position, and with a second trigger in a first pivotal position.

FIG. 35 show a button assembly (550) operable for use with actuation assemblies (300, 400, 500) discussed above. In particular, although button assembly (550) is shown and described as having eight buttons, button assembly (550) may have any number of buttons as will be understood from the discussion below. Button assembly (550) comprises a pair of keyed cylindrical members (552, 554). Each cylindrical member (552, 554) comprises a base (551, 556) with a plurality of teeth (553, 555) angularly separated by a plurality of longitudinal slots, providing each cylindrical member (552, 554) with a castellated configuration. Teeth (553) of cylindrical member (552) are configured to interlock with teeth (555) of cylindrical member (554) such that teeth (553) are disposed between teeth (555) and vice versa.

The depth of the slots between teeth (555) is sufficiently greater than the length of teeth (553) such that a plurality of gaps are formed between a proximal surface of teeth (553) and a proximal surface of the slots between teeth (555). A plurality of buttons (560) are disposed within these gaps. These gaps provide sufficient clearance such that buttons (560) are able to slide within these gaps radially inwardly and outwardly from a center of button assembly (550).

4. Exemplary Alternative Actuation Assembly with Directly Engaged Switch and Distal Pivot FIGS. 36-41 show another exemplary actuation assembly (600). Actuation assembly (600) of this example is configured to operate substantially similar to actuation assembly (200) discussed above except for the differences discussed below. Actuation assembly (600) may be readily incorporated into instrument (120) in place of actuation assembly (200). As shown, actuation assembly (600) comprises a pair of buttons (610, 620). Each button (610, 620) is pivotably coupled to body (132) via a respective pin (611, 621) such that each button (610, 620) is operable to pivot radially inwardly toward and outwardly away from a center of body (132). Buttons (610, 620) are resiliently biased toward the positions shown in FIGS. 36 and 39 and are held in place by contact with an interior surface of body (132). Various suitable ways in which buttons (610, 620) may be resiliently biased will be apparent to those of ordinary skill in the art in view of the teachings herein.

Figure 37:
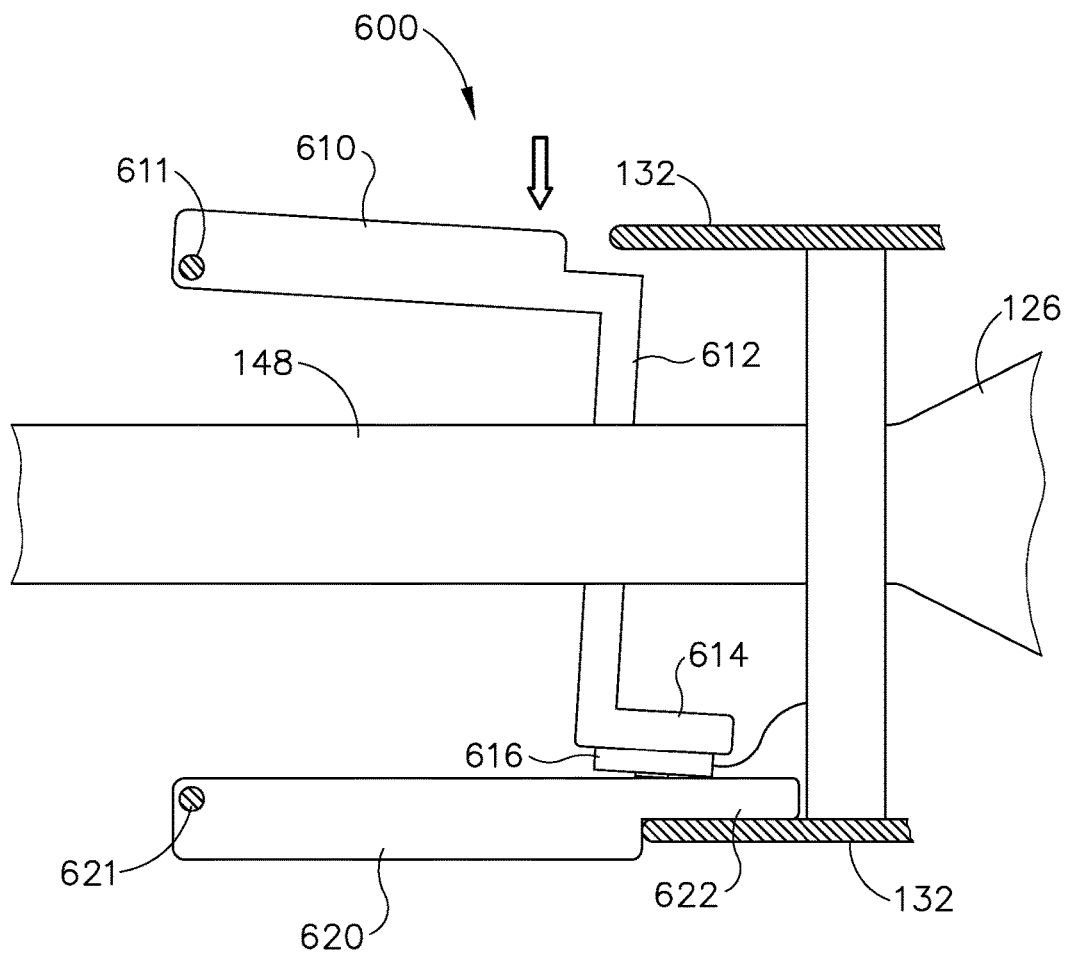
FIG. 37 depicts a cross-sectional side view of the actuation assembly of FIG. 36, with the first trigger moved into a second pivotal position, and with the second trigger in the first pivotal position.
Figure 38:
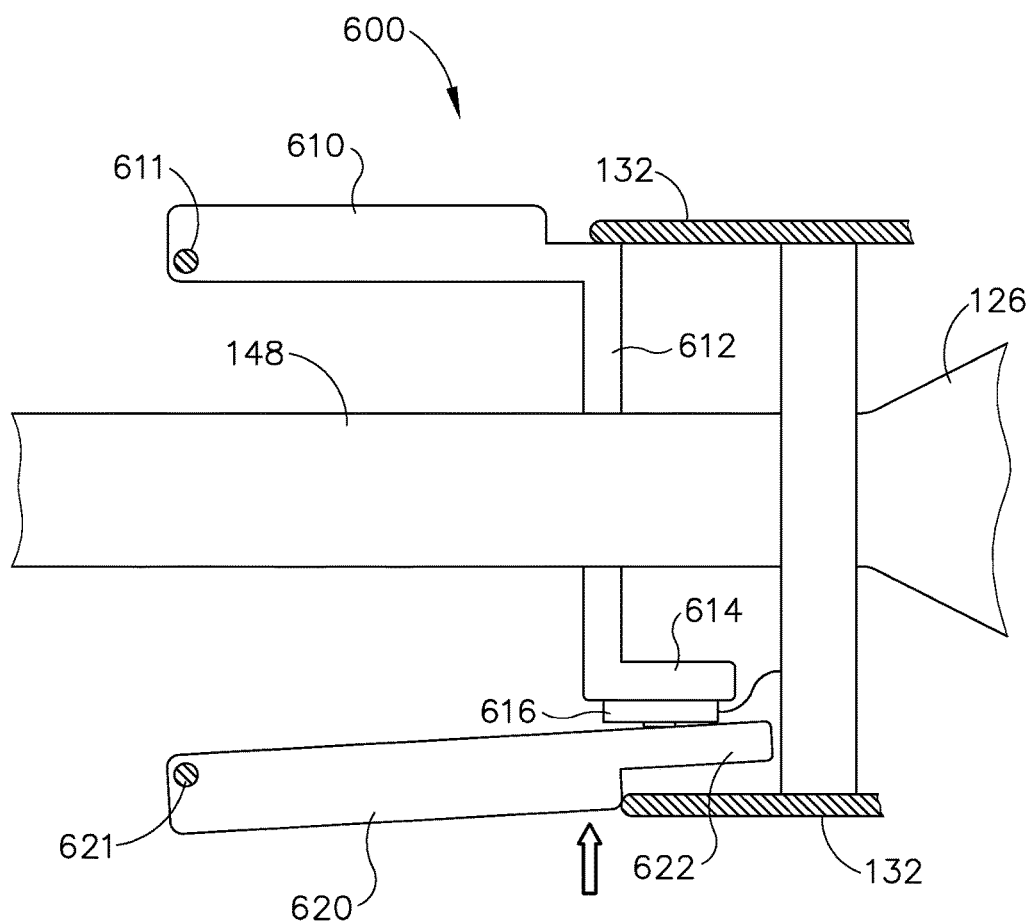
FIG. 38 depicts a cross-sectional side view of the actuation assembly of FIG. 36, with the second trigger moved into a second pivotal position, and with the first trigger in a first pivotal position.
Figure 39:
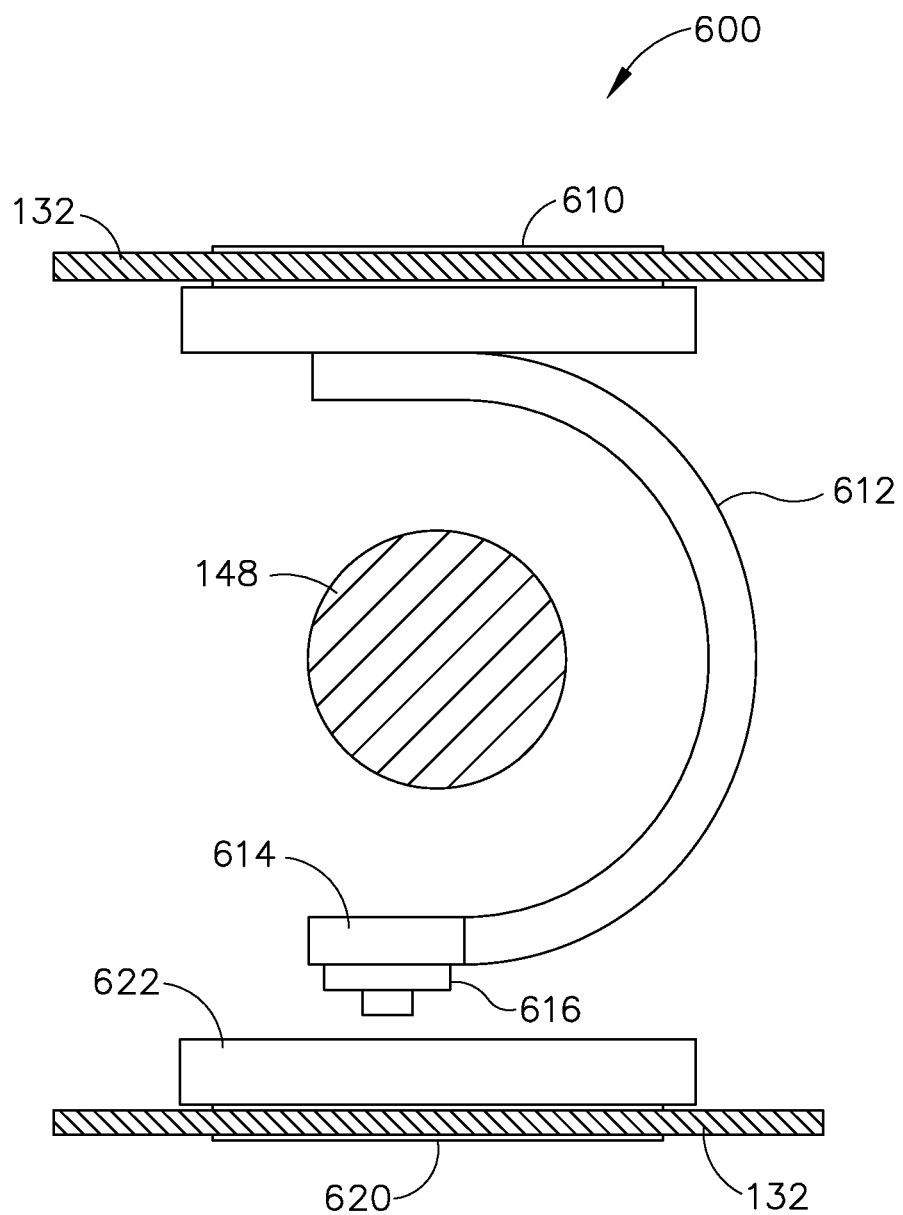
FIG. 39 depicts a front cross-sectional view of the actuation assembly of FIG. 36, taken along line 39-39 of FIG. 36, with the first trigger in the first pivotal position, and with the second trigger in the first pivotal position.
Figure 40:
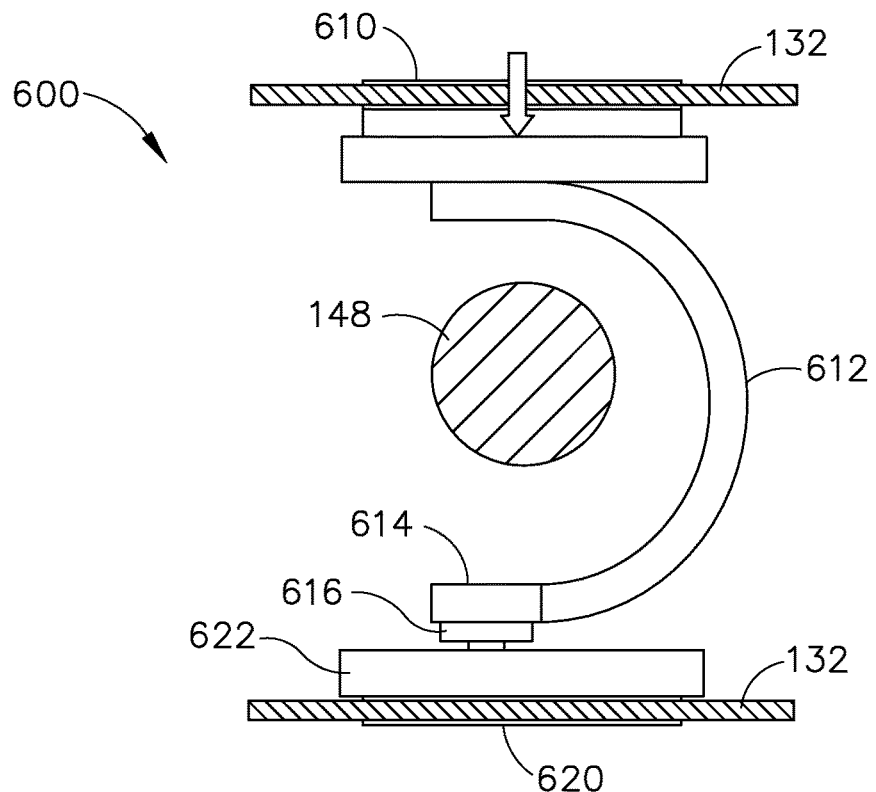
FIG. 40 depicts a front cross-sectional view of the actuation assembly of FIG. 36, taken along line 39-39 of FIG. 36, with the first trigger moved into the second pivotal position, and with the second trigger in the first pivotal position.
Figure 41:
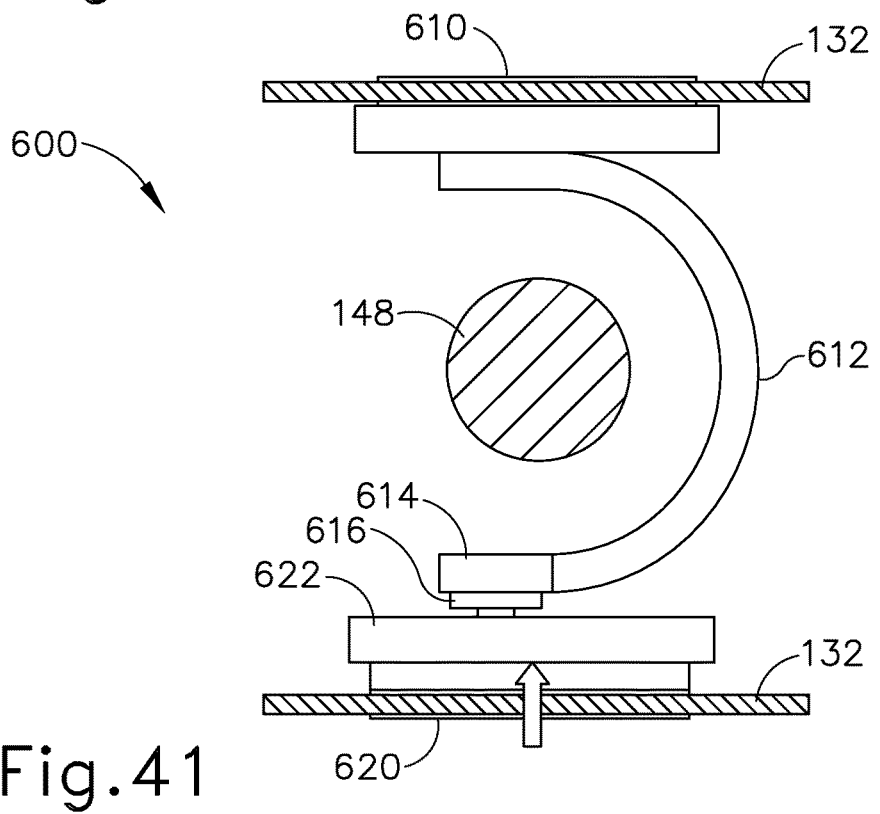
FIG. 41 depicts a front cross-sectional view of the actuation assembly of FIG. 36, taken along line 39-39 of FIG. 36, with the second trigger moved into the second pivotal position, and with the first trigger in the first pivotal position.
Figure 42:
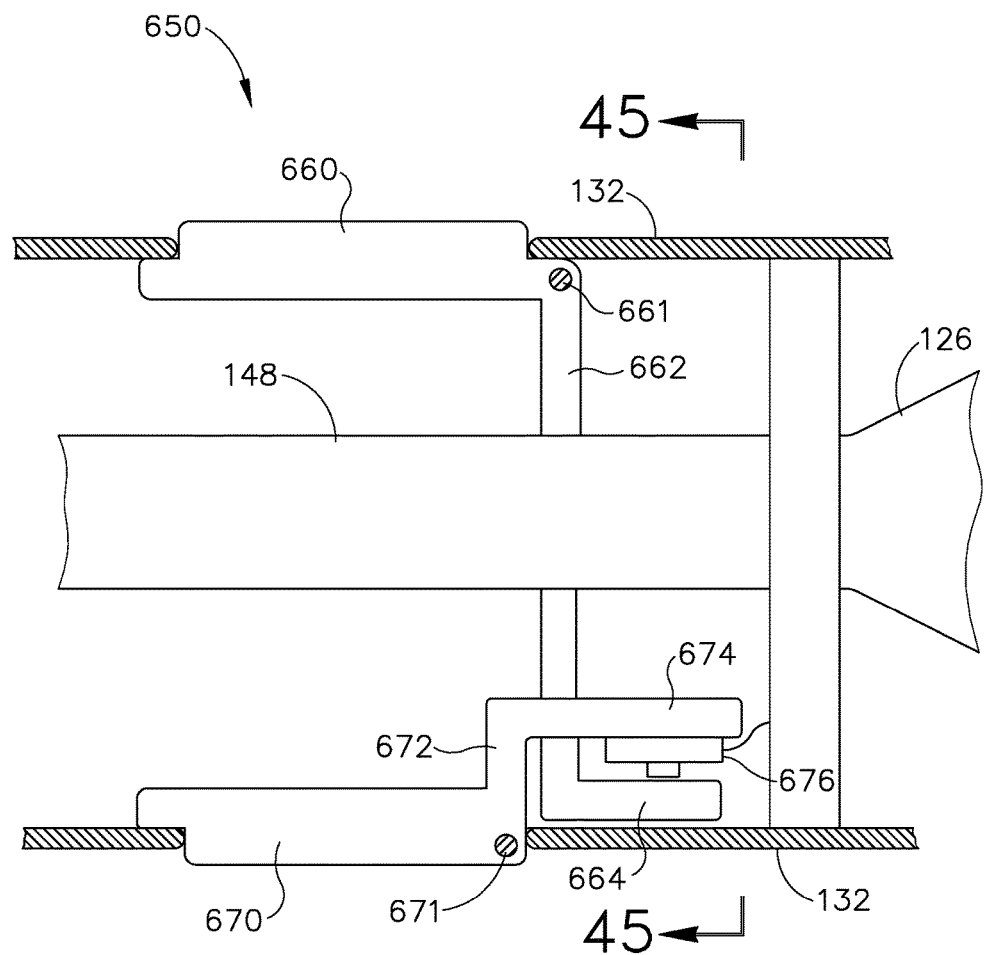
FIG. 42 depicts a side cross-sectional view of yet another exemplary alternative actuation assembly that may be incorporated into the instrument of FIG. 2, with a first trigger in a first pivotal position, and with a second trigger in a first pivotal position.

Button (610) comprises a semi-circular dog-leg portion (612) that passes around waveguide (148), spaced apart from waveguide (148) to a position on the other side of waveguide (148). A base portion (314) of dog-leg portion (612) includes a contact switch (616) extending outwardly away from base portion (614). Button (620) comprises an arm (622) extending laterally adjacent to and spaced apart from contact switch (616). In an initial position, a gap is defined between arm (622) and contact switch (616). FIGS. 37-38 and 40-41 show operation of actuation assembly (600). As shown in FIGS. 37 and 40, as an operator drives button (610) radially inwardly, button (610) pivots about pin (611) such that base portion (614) of dog-leg portion (612) is driven toward arm (622) of button (620) to thereby cause arm (622) to actuate contact switch (616). As shown in FIGS. 38 and 41, as the operator drives button (620) radially inwardly, button (620) pivots about pin (611) such that arm (622) is driven toward contact switch (616) to thereby cause arm (622) to actuate contact switch (616).

In the present example, buttons (610, 620) are configured and oriented such that pivot pins (611, 621) are located at the distal ends of buttons (610, 620); while contact switch (616) is located at the proximal ends of buttons (610, 620). The operator engages buttons (610, 620) at a position located between the proximal and distal ends of buttons (610, 620), such that the operator engages buttons (610, 620) at a position located between pivot pins (611, 621) and contact switch (616). In some other versions, buttons (610, 620) are configured and oriented such that pivot pins (611, 621) are located at the proximal ends of buttons (610, 620); while contact switch (616) is located at the distal ends of buttons (610, 620). In either case, it should be understood that the leverage provided by buttons (610, 620) and the range of angular travel required by buttons (610, 620) in order to actuate switch (616) may be varied based on the length of buttons (610, 620), the positioning of pivot pins (611, 621), and/or based on other variable characteristics.

5. Exemplary Alternative Actuation Assembly with Directly Engaged Switch and Intermediate Pivot FIGS. 42-47 show another exemplary actuation assembly (650). Actuation assembly (650) of this example is configured to operate substantially similar to actuation assembly (200) discussed above except for the differences discussed below. Actuation assembly (650) may be readily incorporated into instrument (120) in place of actuation assembly (200). As shown, actuation assembly (650) comprises a pair of buttons (660, 670). Each button (660, 670) is pivotably coupled to body (132) via a respective pin (661, 671) such that each button (660, 670) is operable to pivot inwardly toward and outwardly away from a center of body (132). Buttons (660, 670) are resiliently biased toward the positions shown in FIGS. 42 and 45 and are held in place by contact with an interior surface of body (132). Various suitable ways in which buttons (660, 670) may be resiliently biased will be apparent to those of ordinary skill in the art in view of the teachings herein.

Figure 43:
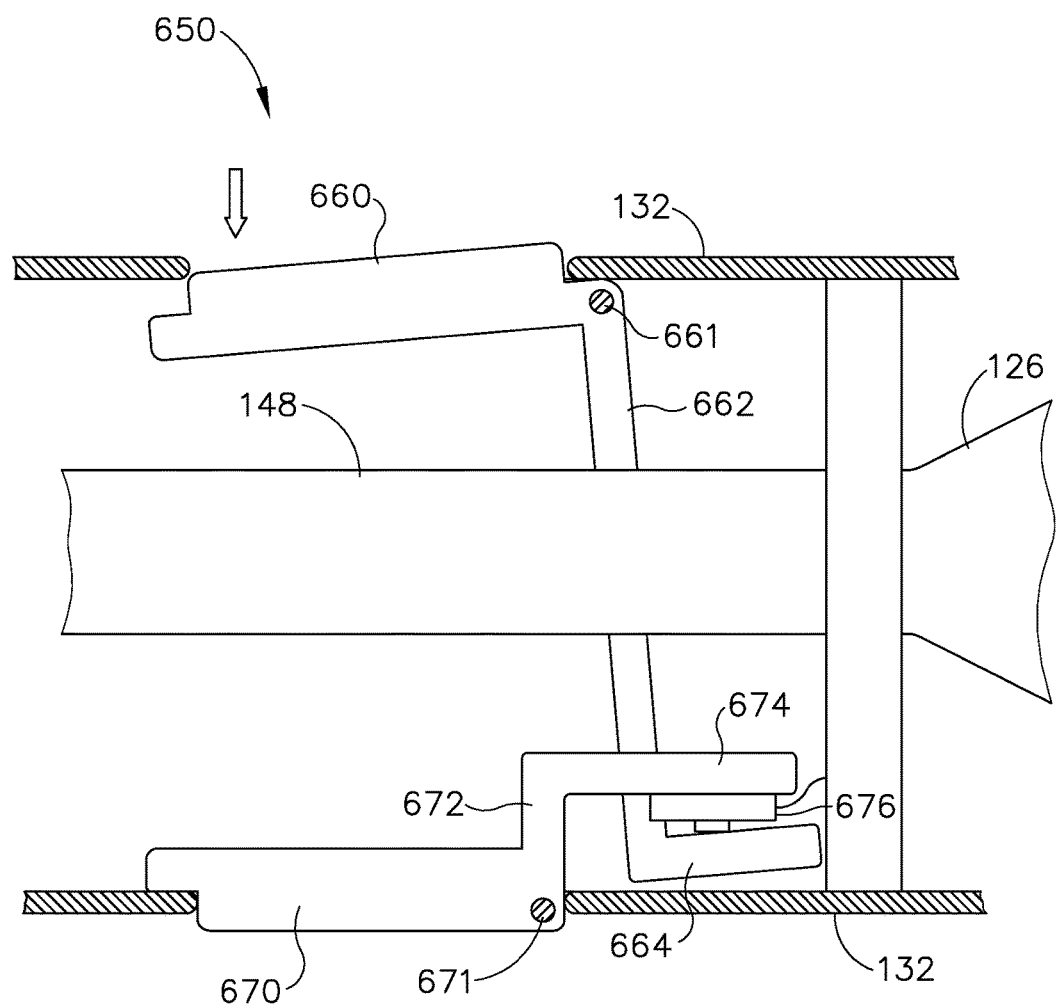
FIG. 43 depicts a side cross-sectional view of the actuation assembly of FIG. 42, with the first trigger moved into a second pivotal position, and with the second trigger in the first pivotal position.
Figure 44:
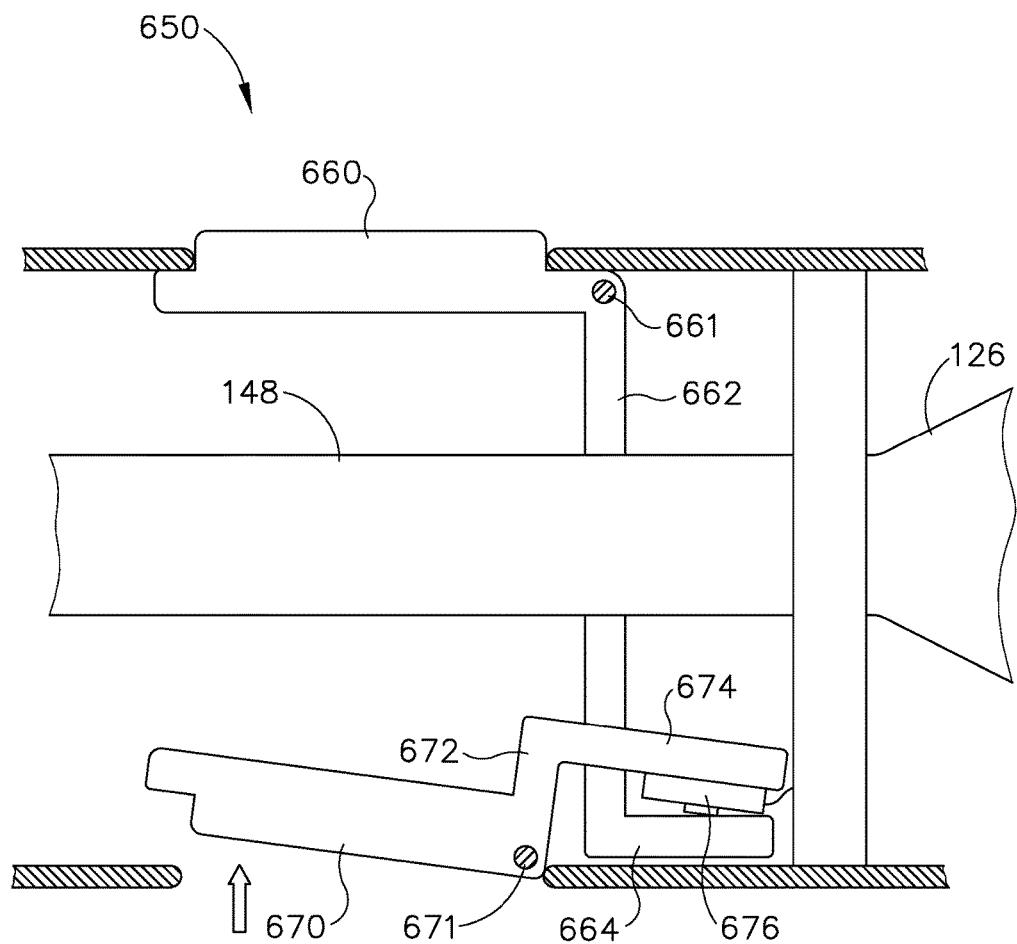
FIG. 44 depicts a side cross-sectional view of the actuation assembly of FIG. 42, with the second trigger moved into a second pivotal position, and with the first trigger in the first pivotal position.
Figure 45:
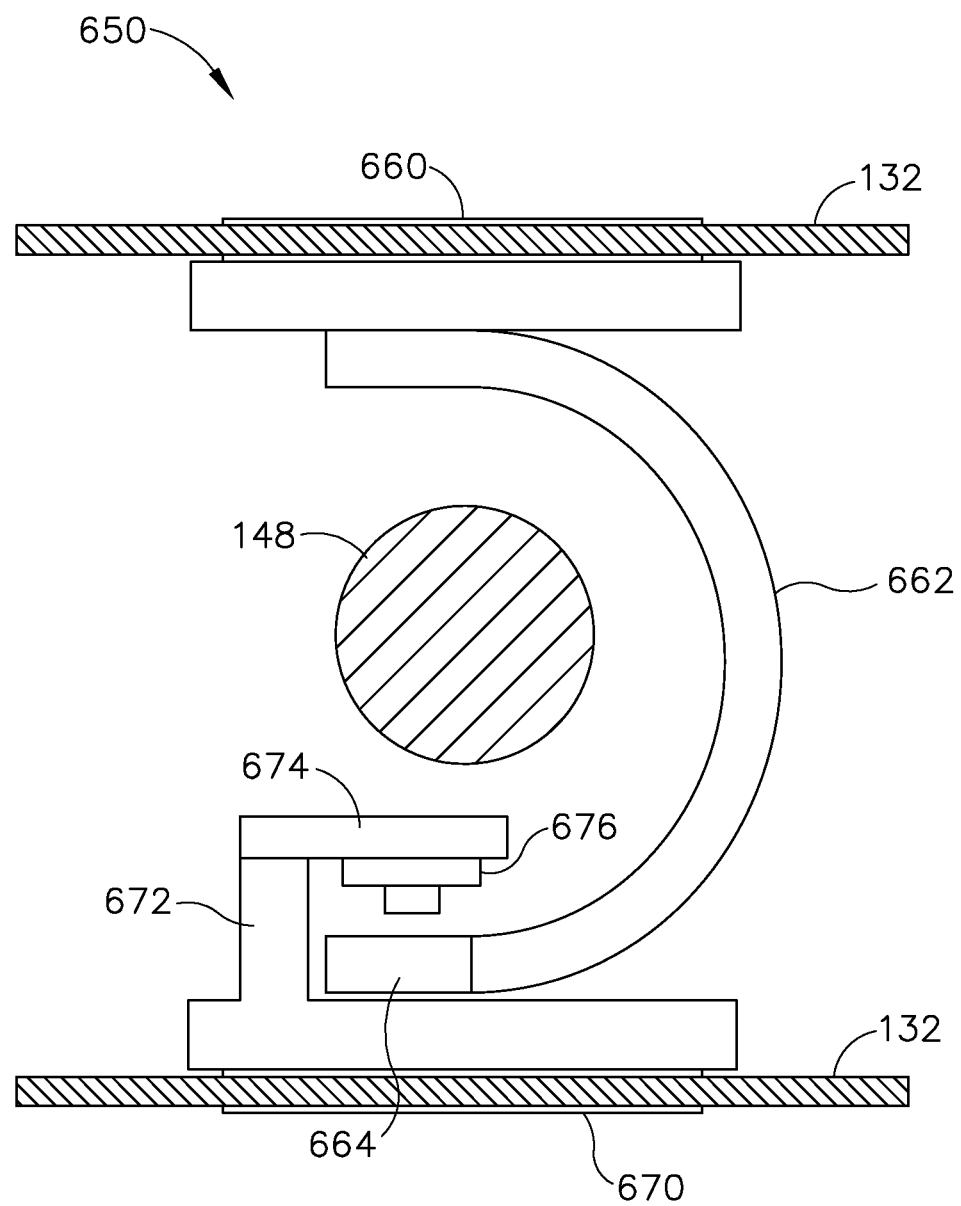
FIG. 45 depicts a front cross-sectional view of the actuation assembly of FIG. 42, taken along line 45-45 of FIG. 42, with the first trigger in the first pivotal position, and with the second trigger in the first pivotal position.
Figure 46:
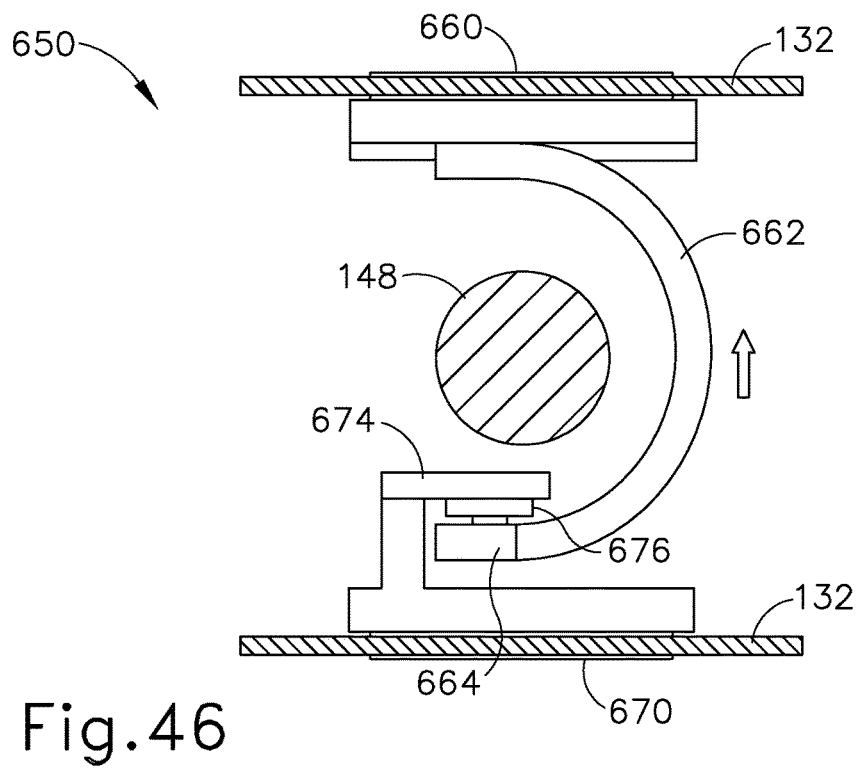
FIG. 46 depicts a front cross-sectional view of the actuation assembly of FIG. 42, taken along line 45-45 of FIG. 42, with the first trigger moved into the second pivotal position, and with the second trigger in the first pivotal position.
Figure 47:
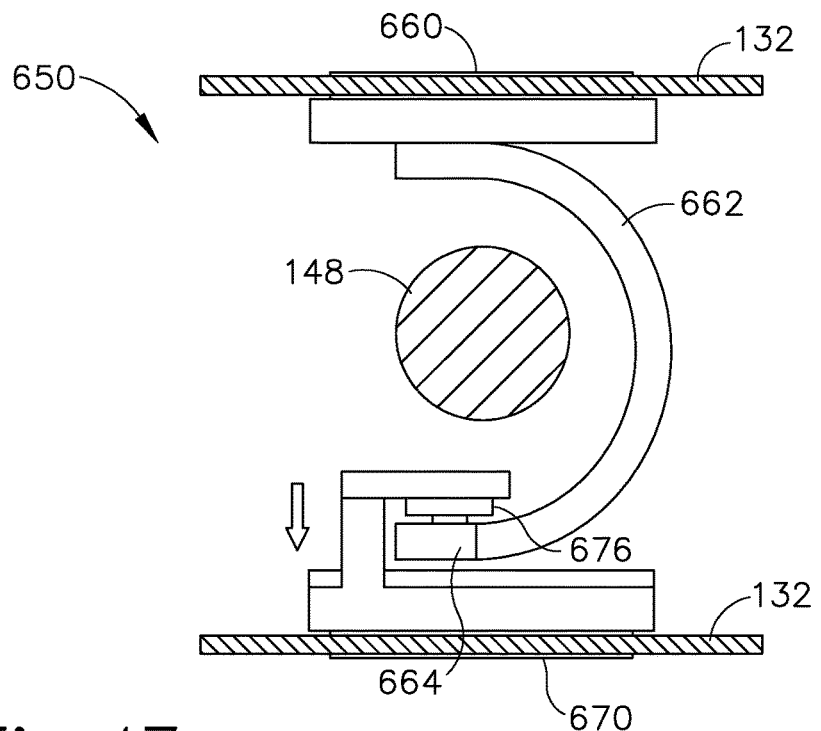
FIG. 47 depicts a front cross-sectional view of the actuation assembly of FIG. 42, taken along line 45-45 of FIG. 42, with the second trigger moved into the second pivotal position, and with the first trigger in the first pivotal position.

Button (660) comprises a semi-circular dog-leg portion (662) that passes around waveguide (148), spaced apart from waveguide (148) to a position on the other side of waveguide (148). Button (670) extends from a top surface of body (132). Button (670) also comprises a dog-leg portion (672). A base portion (674) of dog-leg portion (672) extends laterally adjacent waveguide (148), such that base portion (674) is interposed between waveguide (148) and a base portion (664) of dog-leg portion (662). Base portion (674) of dog-leg portion (672) includes a contact switch (676) extending outwardly from a bottom surface of base portion (674). Base portion (664) of dog-leg portion (662) of button (660) extends laterally adjacent to and spaced apart from contact switch (676). FIGS. 43-44 and 46-47 show operation of actuation assembly (650). As shown in FIGS. 43 and 46, as an operator drives button (660) radially inwardly, button (660) pivots about pin (661) such that base portion (664) of dog-leg portion (662) is driven toward base portion (674) of button (670) to thereby cause base portion (664) to actuate contact switch (676). As shown in FIGS. 44 and 47, as the operator drives button (670) radially inwardly, button (670) pivots about pin (671) such that base portion (674) is driven toward contact switch (676) to thereby cause base portion (664) of button (660) to actuate contact switch (676).

In the present example, buttons (660, 670) are configured and oriented such that pivot pins (661, 671) are located longitudinally intermediate regions of buttons (660, 670); while contact switch (676) is located at the proximal ends of buttons (660, 670). The operator engages buttons (660, 670) at a distal end of buttons (660, 670), such that the operator engages buttons (660, 670) at a position located distal to pivot pins (661, 671) and contact switch (676). In some other versions, buttons (660, 670) are configured and oriented such that the operator engages the proximal ends of buttons (610, 620); while contact switch (676) is located at the distal ends of buttons (660, 670). In either case, it should be understood that the leverage provided by buttons (660, 670) and the range of angular travel required by buttons (660, 6700) in order to actuate switch (676) may be varied based on the length of buttons (660, 670), the positioning of pivot pins (661, 671), and/or based on other variable characteristics.

III. Miscellaneous

While several of the examples described above include a contact switch (180, 312, 412, 512, 616, 676), it should be understood that any other suitable kind of switches may be used. Moreover, various other kinds of structures may be used to provide an electrical signal to generator (12), to close a circuit between generator (12) and transducer (126), and/or to otherwise selectively activate transducer (126) and/or waveguide (148). Various suitable alternatives will be apparent to those of ordinary skill in the art in view of the teachings herein. It is contemplated that all of these alternatives are included within the meaning of the broad term "switch."

It should be understood that any of the versions of instruments described herein may include various other features in addition to or in lieu of those described above. By way of example only, any of the instruments described herein may also include one or more of the various features disclosed in any of the various references that are incorporated by reference herein. It should also be understood that the teachings herein may be readily applied to any of the instruments described in any of the other references cited herein, such that the teachings herein may be readily combined with the teachings of any of the references cited herein in numerous ways. Other types of instruments into which the teachings herein may be incorporated will be apparent to those of ordinary skill in the art.

It should also be understood that any ranges of values referred to herein should be read to include the upper and lower boundaries of such ranges. For instance, a range expressed as ranging "between approximately 1.0 inches and approximately 1.5 inches" should be read to include approximately 1.0 inches and approximately 1.5 inches, in addition to including the values between those upper and lower boundaries.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. Similarly, those of ordinary skill in the art will recognize that various teachings herein may be readily combined with various teachings of U.S. Pat. No. 6,783,524, entitled "Robotic Surgical Tool with Ultrasound Cauterizing and Cutting Instrument," published Aug. 31, 2004, the disclosure of which is incorporated by reference herein.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by an operator immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An ultrasonic instrument comprising:
   (a) a body, wherein the body defines a longitudinal axis, wherein the body is configured to receive an ultrasonic transducer;
   (b) an actuation assembly, wherein the actuation assembly comprises:
      (i) a plurality of buttons, wherein the plurality of buttons are disposed angularly about the body, wherein each button of the plurality of buttons is configured to move toward and away from the longitudinal axis of the body, and wherein each of the plurality of buttons includes a button cam surface,
      (ii) an actuation body having at least one actuation cam surface that is selectively movable from a first position to a second position, wherein each of the button cam surfaces is configured to engage the at least one actuation cam surface via movement of each the respective buttons toward the longitudinal axis thereby directing the actuation body from the first position to the second position, and
      (iii) a switch, wherein the actuation body is configured to actuate the switch as the actuation body moves from the first position to the second position via at least one of the plurality of buttons;
   (c) an acoustic waveguide, wherein the switch is operable to trigger activation of the acoustic waveguide; and
   (d) an ultrasonic blade, wherein the ultrasonic blade is in acoustic communication with the acoustic waveguide.

2. The ultrasonic instrument of claim 1, wherein each button of the plurality of buttons is pivotable toward and away from the longitudinal axis of the body.

3. The ultrasonic instrument of claim 1, wherein each button of the plurality of buttons is translatable toward and away from the longitudinal axis of the body.

4. The ultrasonic instrument of claim 1, wherein the actuation body comprises a sled, wherein each button of the plurality of buttons is operable to actuate the sled.

5. The ultrasonic instrument of claim 4, wherein the sled is configured to translate longitudinally to thereby actuate the switch.

6. The ultrasonic instrument of claim 4, wherein each button cam surface of the plurality of buttons comprises an angled camming surface, wherein the at least one actuation cam surface of the sled comprises a plurality of angled camming surfaces, wherein an angled camming surface of each button of the plurality of buttons is aligned with a corresponding angled camming surface of the sled.

7. The ultrasonic instrument of claim 4, wherein each button of the plurality of buttons is configured to move toward and away from the longitudinal axis of the body to thereby cause longitudinal translation of the sled.

8. The ultrasonic instrument of claim 1, further comprising a torquing mechanism configured to provide a restricted amount of torque to couple the acoustic waveguide with an ultrasonic transducer received by the body.

9. The ultrasonic instrument of claim 8, wherein the torquing mechanism comprises:
   (i) a first rack, wherein the first rack comprises a first plurality of teeth, and
   (ii) a second rack, wherein the second rack comprises a second plurality of teeth,
   wherein the first plurality of teeth and the second plurality of teeth are configured to engage one another to thereby communicate rotation of the first rack to the second rack,
   wherein the first plurality of teeth and the second plurality of teeth are configured to disengage when a predetermined level of toque is experienced such that rotation of the first rack is not communicated to the second rack upon reaching the predetermined level of torque.

10. The ultrasonic instrument of claim 9, wherein the first rack is biased toward the second rack.

11. The ultrasonic instrument of claim 1, wherein the actuation assembly further comprises a band in communication with at least one button of the plurality of buttons.

12. The ultrasonic instrument of claim 11, wherein the band is configured to translate transversely or flex to thereby actuate the switch in response to actuation of a button of the plurality of buttons.

13. The ultrasonic instrument of claim 11, wherein the band is in contact with at least one button of the plurality of buttons, wherein each button of the plurality of buttons is configured to move toward and away from the longitudinal axis of the body to thereby cause transverse translation or flexing of the band.

14. The ultrasonic instrument of claim 1, wherein the switch is secured to a first button of the plurality of buttons.

15. The ultrasonic instrument of claim 14, wherein the first button is configured to move toward and away from the longitudinal axis of the body to thereby actuate the switch.

16. The ultrasonic instrument of claim 14, wherein a second button of the plurality of buttons is configured to move toward and away from the longitudinal axis of the body to thereby actuate the switch.

17. An ultrasonic instrument comprising:
   (a) a body, wherein the body defines a longitudinal axis, wherein the body is configured to receive an ultrasonic transducer;

(b) an actuation assembly, wherein the actuation assembly comprises:
  (i) a plurality of buttons, wherein the plurality of buttons are disposed angularly about the body, wherein each button of the plurality of buttons is operable to move toward and away from the longitudinal axis of the body,
  (ii) a switch, wherein the switch is secured to a first button of the plurality of buttons, and
  (iii) a band in communication with one or more of the buttons, wherein the band is configured to translate transversely or flex to thereby actuate the switch, wherein the band is in contact with at least a second button of the plurality of buttons, wherein at least the second button of the plurality of buttons is configured to move toward and away from the longitudinal axis of the body to thereby cause transverse translation or flexing of the band;
(c) an acoustic waveguide, wherein the switch is operable to trigger activation of the acoustic waveguide; and
(d) an ultrasonic blade, wherein the ultrasonic blade is in acoustic communication with the acoustic waveguide.

18. The ultrasonic instrument of claim 17, wherein the actuation assembly further comprises an elastomeric member, wherein the elastomeric member is configured to resiliently bias the plurality of buttons outwardly relative to the longitudinal axis of the body.

19. The ultrasonic instrument of claim 17, wherein the first button of the plurality of buttons comprises at least one pin, wherein the at least one pin is configured to engage the band to thereby support and align the band.

20. An ultrasonic instrument comprising:
(a) a body, wherein the body defines a longitudinal axis, wherein the body is configured to receive an ultrasonic transducer;
(b) an actuation assembly, wherein the actuation assembly comprises:
  (i) a plurality of buttons, wherein the plurality of buttons comprises a first button and a second button,
  (ii) an actuation body, wherein the first button is configured to move toward the longitudinal axis of the body to thereby actuate the actuation body from a first position to a second position, wherein the second button is configured to move toward the longitudinal axis of the body to thereby actuate the actuation body from the first position to the second position, and
  (iii) a switch, wherein the actuation body is configured to actuate the switch as the actuation body moves from the first position to the second position via at least one of the first and second buttons;
(c) an acoustic waveguide, wherein the switch is operable to trigger activation of the acoustic waveguide; and
(d) an ultrasonic blade, wherein the ultrasonic blade is in acoustic communication with the acoustic waveguide.

* * * * *